(12) United States Patent
Narayan et al.

(10) Patent No.: US 11,786,174 B2
(45) Date of Patent: Oct. 17, 2023

(54) SYSTEM AND METHOD TO MAINTAIN HEALTH USING PERSONAL DIGITAL PHENOTYPES

(71) Applicant: The Board of Trustees of the Leland Stanford Junior University, Palo Alto, CA (US)

(72) Inventors: Sanjiv M. Narayan, Palo Alto, CA (US); Mahmood Alhusseini, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 138 days.

(21) Appl. No.: 17/051,749

(22) PCT Filed: Apr. 24, 2019

(86) PCT No.: PCT/US2019/029004
§ 371 (c)(1),
(2) Date: Oct. 29, 2020

(87) PCT Pub. No.: WO2019/212833
PCT Pub. Date: Nov. 7, 2019

(65) Prior Publication Data
US 2021/0236053 A1     Aug. 5, 2021

Related U.S. Application Data

(60) Provisional application No. 62/664,833, filed on Apr. 30, 2018.

(51) Int. Cl.
*A61B 5/00*      (2006.01)
*A61B 5/361*     (2021.01)
(Continued)

(52) U.S. Cl.
CPC .......... *A61B 5/4836* (2013.01); *A61B 5/0004* (2013.01); *A61B 5/024* (2013.01);
(Continued)

(58) Field of Classification Search
None
See application file for complete search history.

(56) References Cited

U.S. PATENT DOCUMENTS

| 6,231,570 B1 | 5/2001 | Tu et al. |
| 7,171,269 B1 | 1/2007 | Addison et al. |

(Continued)

FOREIGN PATENT DOCUMENTS

| CN | 106066933 A | 11/2016 |
| EP | 2603138 B1 | 1/2017 |

(Continued)

OTHER PUBLICATIONS

PCT/US2019/029004 International Search Report & Written Opinion of the International Searching Authority, dated Sep. 10, 2019, 7 pages.
(Continued)

*Primary Examiner* — Catherine M Voorhees
*Assistant Examiner* — Elizabeth K So
(74) *Attorney, Agent, or Firm* — Eleanor Musick; Torrey Pines Law Group PC

(57) ABSTRACT

A system and method for identifying and treating a disease in a patient collects one or more data streams from sensors configured to detect biological signals generated within a patient's tissue over time. Patient data elements including one or more of demographic, clinical, laboratory, pathology, chemical, image, historical, genetic, and activity data for the patient is collected and processed with the data streams to generate a personalized digital phenotype (PDP). The PDP is compared to a digital taxonomy comprising prior data to
(Continued)

classify the patient into one or more quantitative disease classifications to guide personalized intervention for treating the patient.

31 Claims, 24 Drawing Sheets

(51) Int. Cl.
- *A61B 5/363* (2021.01)
- *A61B 5/024* (2006.01)
- *A61B 5/08* (2006.01)

(52) U.S. Cl.
CPC ............ *A61B 5/0816* (2013.01); *A61B 5/361* (2021.01); *A61B 5/363* (2021.01); *A61B 5/7246* (2013.01); *A61B 5/7264* (2013.01); *A61B 2562/0204* (2013.01); *A61B 2562/0219* (2013.01); *A61B 2562/0238* (2013.01); *A61B 2562/0271* (2013.01)

(56) References Cited

U.S. PATENT DOCUMENTS

| | | | |
|---|---|---|---|
| 8,287,526 B2 | 10/2012 | Arless et al. | |
| 8,538,774 B2 | 9/2013 | Michelson et al. | |
| 8,700,140 B2 * | 4/2014 | Narayan | A61B 5/6852 600/518 |
| 8,868,169 B2 * | 10/2014 | Narayan | A61B 5/349 600/512 |
| 8,876,817 B2 | 11/2014 | Avitall et al. | |
| 8,954,339 B2 | 2/2015 | Schaffer | |
| 9,730,603 B2 | 8/2017 | Laughner et al. | |
| 9,757,191 B2 | 9/2017 | Avitall et al. | |
| 11,540,879 B2 | 1/2023 | Bort et al. | |
| 11,564,591 B1 | 1/2023 | Narayan et al. | |
| 11,583,346 B2 | 2/2023 | Bort et al. | |
| 2004/0122709 A1 | 6/2004 | Avinash et al. | |
| 2006/0167529 A1 | 7/2006 | Schecter | |
| 2010/0042438 A1 | 2/2010 | Moore et al. | |
| 2012/0100134 A1 | 4/2012 | Lenz | |
| 2012/0123232 A1 | 5/2012 | Najarian et al. | |
| 2013/0267875 A1 | 10/2013 | Thapliyal et al. | |
| 2014/0164784 A1 | 6/2014 | Sinderbrand et al. | |
| 2015/0042646 A1 | 2/2015 | Comaniciu et al. | |
| 2015/0223759 A1 | 8/2015 | Ong et al. | |
| 2017/0164893 A1 | 6/2017 | Narayan et al. | |
| 2017/0202515 A1 | 7/2017 | Zrihem et al. | |
| 2017/0332971 A1 | 11/2017 | MacNeil et al. | |
| 2017/0354339 A1 | 12/2017 | Zeidan et al. | |
| 2018/0214202 A1 | 8/2018 | Howard et al. | |
| 2020/0085311 A1 | 3/2020 | Tzvieli et al. | |
| 2020/0367957 A1 | 11/2020 | Altmann et al. | |
| 2021/0022794 A1 | 1/2021 | Viswanathan | |
| 2021/0045805 A1 | 2/2021 | Govari et al. | |
| 2021/0059737 A1 | 3/2021 | Babkin et al. | |
| 2021/0077180 A1 | 3/2021 | Govari et al. | |
| 2021/0106249 A1 | 4/2021 | Schmidt et al. | |
| 2021/0220047 A1 | 7/2021 | Curran et al. | |
| 2022/0338923 A1 | 10/2022 | Bort et al. | |
| 2022/0338936 A1 | 10/2022 | Bort et al. | |
| 2022/0344025 A1 | 10/2022 | Bort et al. | |
| 2023/0049942 A1 | 2/2023 | Narayan et al. | |

FOREIGN PATENT DOCUMENTS

| | | | |
|---|---|---|---|
| EP | 2339961 B1 | 3/2018 | |
| EP | 3777743 A1 | 2/2021 | |
| EP | 3791816 A2 | 3/2021 | |
| WO | 2006039694 A2 | 4/2006 | |
| WO | 2010042826 A | 4/2010 | |
| WO | WO-2013036677 A1 * | 3/2013 | ......... G06F 19/3418 |
| WO | 2013106557 A1 | 7/2013 | |
| WO | 2016033609 A1 | 3/2016 | |
| WO | 2019212833 A1 | 7/2019 | |
| WO | 2023018741 A | 2/2023 | |
| WO | 2023096666 A1 | 6/2023 | |

OTHER PUBLICATIONS

LeCun, e al., Gradient-Based Learning Applied to Document Recognition, Proc. of the IEEE, 1998, pp. 1-46.

Rajpurkar, et al., Cardiologist-Level Arrhythmia Detection with Convolutional Neural Networks, Jul. 6, 2017, pp. 1-9.

Esteva, et al., Dermatologist-level classification of skin cancer with deep neural networks, Nature, Feb. 2, 2017, pp. 115-125, vol. 542.

Alhusseini, M. et al., Machine Learning to Classify Intracardiac Electrical Patems During Atrial Fibrillation, Arrhythm Electrophysiol., Aug. 2020, pp. 719-729.

Baykaner, T., et al., Machine Learning of Adipose Tissue in Atrial Fibrillation, Heart Rhythm, Dec. 2022, pp. 2042-2043, vol. 19.

Ganesan, P., et al., Quantifying a spectrum of clinical response in atrial tachyarrhythmias using spatiotemporal synchronization of electrograms, European Society of Cardiology, Europace 2023, pp. 1-9, vol. 25.

Nussinovitch, U., et al., Ambient Circulation Surrounding an Ablation Catheter Tip Affects Ablation Lesion Characteristics, J. Cardiovasc Electrophysiol., Apr. 2023, pp. 1-18, vol. 34(4).

Rodrigo, M., et al., Atrial Fibrillation signatures on intracardiac electrograms identified by deep learning, Computers in Biology and Medicine, 2022, pp. 1-9.

Roney, C. et al., Predicting Atrial Fibrillation Recurrence by Combining Population Data and Virtual Cohorts of Patient-Specific left Atrial Models, Circ Arrhythm Electrophysiol., Feb. 2022, pp. 94-102.

Tang, S., et al., Machine Learning-Enabled Multimodal Fusion of Intra-Atrial and Body Surface Signals in Prediction of Atrial Fibrillation Ablation Outcomes, Circ. Arrhythm Electrophysiol., Aug. 2022, pp. 500-509.

International Search Report and Written Opinion of the ISA, PCT/US2021/018940, dated May 4, 2021, 10 pages.

International Search Report and Written Opinion of the ISA, PCT/US2022/039873, dated Jan. 30, 2023, 11 pages.

International Search Report and Written Opinion of the ISA, PCT/SU2022/029630, dated Oct. 26, 2022, 23 pages.

\* cited by examiner

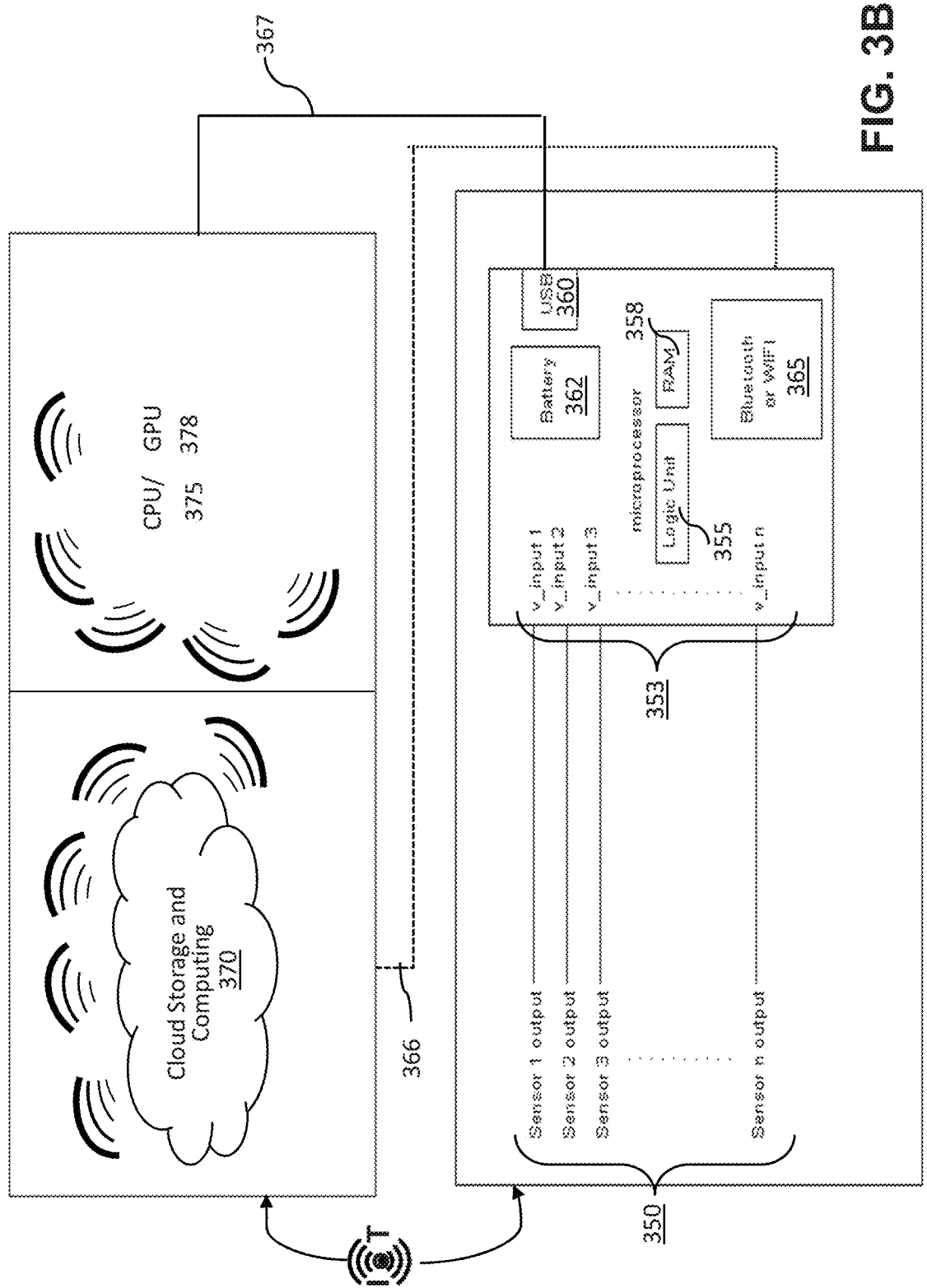

2. Destabilization of Locus

SYSTEM AND METHOD TO MAINTAIN HEALTH USING PERSONAL DIGITAL PHENOTYPES

RELATED APPLICATIONS

This application is a 371 national stage filing of International Application No. PCT/US2019/029004, filed Apr. 24, 2019, which claims the benefit of the priority of U.S. Provisional Application No. 62/664,833, filed Apr. 30, 2018, each of which is incorporated herein by reference in its entirety.

GOVERNMENT RIGHTS

This invention was made with government support under Grants HL83359 and HL103800 awarded by the National Institutes of Health (NIH). The government has certain rights in the invention.

FIELD OF THE INVENTION

The present invention relates generally to personalized therapy for disease and maintenance of health, and more specifically to a system and method for defining digital phenotypes for a disease based on data collected for a specific person that can be referenced to a digital taxonomy for the disease based on data from a population, providing identification of critical abnormalities for personalized therapy.

BACKGROUND OF THE INVENTION

It is increasingly appreciated that medical therapy is often too generic and may be improved by personalization. Many accepted therapies work respectably well across populations yet poorly or not at all in a significant minority of cases. Even in those in whom a therapy works, there is typically a gradation of response across individuals. There are often few a priori clues that a particular therapy may not work in a given patient. A priori "predictors" of response or failure are actually typically based on observed post-hoc success and failure, and attempts to use them to improve therapy often produce incremental, rather than substantial, benefits.

Current medical practice for a stated condition explicitly prioritizes applicability for the majority of individuals over the statistical minority because only therapies that work in the majority are promoted. An important but overlooked issue is the fate of the minority of individuals with the stated condition who may respond to a therapy that differs from that used on the majority. This minority may comprise a substantial number of individuals, but the therapy is often abandoned even for these individuals, except for instances when they are readily identified (phenotyped) from others with the stated condition. Such "sub"-phenotyping is often difficult, because otherwise such individuals would have been separated from others with the stated condition beforehand, into a different subcategory.

There is an urgent need to personalize therapy: to identify a priori those patients in whom a therapy is likely to work, those in whom that therapy is less likely to work, and, ideally, to optimize therapy for the individual. To meet these objectives, personalized medicine is increasingly studied using strategies to identify genetic cause(s) for a condition, phenotype individuals accordingly, and tailor therapies based on this phenotype.

Personalized medicine is applied most often for conditions resulting from a genetic abnormality ("mechanism"), and applied less frequently for conditions for which clear genetic traits are not demonstrable. Unfortunately, this includes many of the most prevalent diseases of all organ systems. In the heart, while genetic cases can be identified for conditions such as coronary disease or heart rhythm disturbances including atrial fibrillation (AF), for example, patients with inherited familial hypercholesterolemia or lone AF, such cases are the minority. Most cases do not have a clearly demonstrable genetic cause and are considered to be due to multiple factors (multifactorial). Some recent studies failed to show genetic abnormalities even in conditions considered genetic, including inherited sudden cardiac arrest in the young, i.e., Sudden Arrhythmic Death Syndrome ("SAD S").

Other conditions may appear partially heritable, or may have genetic causes with "incomplete penetrance." The causes for such variability in disease expression or response to therapy are unknown and occur, for example, with many therapies for atrial fibrillation. Such variability is often ascribed to "environment," and may be represented as the variations in the cellular "proteome" or "metabolome," but may be difficult to identify, is often unproven, and is rarely used to guide therapy.

Heart rhythm disorders are common and significant causes of morbidity and death throughout the world. In normal conditions, the sinus node keeps the heart in sinus rhythm. Under certain conditions, rapid activation of the normal sinus node can cause inappropriate sinus tachycardia or sinus node reentry, both of which also represent heart rhythm disorders.

Malfunction of the electrical system in the heart is a proximate cause of heart rhythm disorders. Heart rhythm disorders may be classified as simple or complex. To some extent, this is arbitrary based upon whether or not the rhythm is currently well understood and treatable. However, simple rhythms may be considered to have a well-defined circuit that is stable over time, with agreement by most methods of analysis (mapping). Examples include sinus rhythm (SR), atrial tachycardia (AT) or flutter (AFL), atrio-ventricular nodal reentry tachycardia (AVNRT) and atrio-ventricular reciprocating tachycardia (AVRT). Conversely, complex rhythm disorders include atrial fibrillation (AF), ventricular fibrillation (VF) and other forms of rhythm where the circuit changes over time such as polymorphic ventricular tachycardia (PMVT), multiple premature atrial complexes (PACs), multiple premature ventricular complexes (PVCs), and inter-related atrial macro-reentry circuits.

Treatment of heart rhythm disorders, particularly complex rhythm disorders of AF, VF and VT, can be difficult. Pharmacologic therapy for complex rhythm disorder is not optimal. Ablation has been used increasingly for heart rhythm disorders by maneuvering a sensor/probe to the heart through the blood vessels, or directly at surgery, and delivering energy to a location of the heart to mitigate and, in some cases, eliminate the heart rhythm disorder. However, in complex rhythm disorders, ablation is often difficult and ineffectual because tools that identify and locate a cause (source) of the heart rhythm disorder are deficient, hindering attempts to deliver energy to the appropriate region of the heart to eliminate the disorder. Despite best efforts, drug therapy for complex arrhythmias has only 30-60% success in the medium to long term. Ablation is increasingly used but is suboptimal for complex conditions. For instance, success of a single ablation procedure for "paroxysmal" AF, considered the simplest form, is 65% at one year dropping to 50% over time in a recent multicenter trial. For patients with more complex, persistent AF, the single procedure success by the "gold standard" technique is about 40-50% at year one off medications in a recent multicenter trial by Verma, et al., ("Approaches to catheter ablation for persistent atrial fibrillation," *N Engl J Med.* 2015; 372:1812-22.) Each of these studies agrees with the results of many other multicenter prospective investigations.

Several unmet needs exist which, if addressed by new scientific breakthroughs or inventions, may help to improve these success rates of therapy. Many unanswered questions remain: Why does the same ablation approach work in some patients yet not others, despite multiple attempts? What mechanisms for rhythm disorders are similar or differ between individuals, and can we identify phenotypes for them? Current disease classifications are not ideal for this purpose, since pulmonary vein isolation fails in 35-50% of cases of "simple" paroxysmal AF at 1-2 years yet works in 40-50% of cases of "advanced" persistent AF at 1-2 years. Why do some patients do well after ablation of proposed AF sources, while others do not? In AF driven by sources, why do some individuals have only one source, even for complex AF, while others have several? Why do sources or driver regions relate to structural abnormalities such as fibrosis on magnetic resonance imaging or voltage analysis in some individuals but not in others (Narayan et al., *Circulation Arrhythmia/Electrophysiology* 2013; 6(1): 58-67)? Why do heart rhythm conditions such as AF relate to processes such as neural stimuli or metabolic diseases such as diabetes mellitus in some individuals but not others?

Heart rhythm disorders are classified by their electrical patterns within the heart. Detailed mapping led to definition of conditions such as AVRT, their separation from other conditions which may otherwise have similar symptoms or ECG appearance, and then identification of causes to develop curative therapy. Prior art strategies to classify electrical causes for heart rhythm disorders used several methods. In a simple heart rhythm disorder such as atrial tachycardia, the source of the disorder can be identified by tracing activation back to the earliest location, which can be cauterized (ablated) to mitigate and, in some cases, to eliminate the disorder. However, even in simple heart rhythm disorders, ablating the cause of a heart rhythm disorder is challenging and experienced practitioners often require hours to ablate simple rhythm disorders that exhibit consistent beat-to-beat activation patterns such as atrial tachycardia.

In a complex rhythm disorder, diagnosis and treatment often involves the introduction of a catheter having a plurality of sensors/probes into the heart through blood vessels of a patient. The sensors detect electric activity of the heart at sensor locations in the heart. The electric activity is generally processed into electrogram signals that represent the activation of the heart at the sensor locations. In a complex disorder, signals at each sensor location may transition from beat-to-beat between one, several, and multiple deflections of various shapes. For instance, when a signal for a sensor location in AF includes 5, 7, 11 or more deflections, it is difficult to identify which deflections in the signal are local to the sensor location in the heart (i.e., local activation onset) versus a nearby sensor location in the heart (i.e., far-field activation onset) or simply noise from another part of the patient's heart, other anatomic structures or external electronic systems. Such irregular deflections make it difficult, if not impossible, to identify activation onset times of the beats in a signal at a sensor location although recent attempts have been made (Sahli et al., *Ann Biomed Eng* 2018; 46(2): 257-269; Zaman et al., *Circ Arrhythm Electrophysiol* 2018; 11: e005258).

Several attempts have been made to identify causes for a heart rhythm disorder. One method treats regularity in signals at sensor locations as a surrogate for the source of the complex rhythm disorder, in which a source is considered more organized than adjacent sensor locations. For example, U.S. Pat. No. 7,117,030 to Berenfeld et al., U.S. Pat. No. 5,792,189 to Gray et al., Sahadevan et al. (*Circulation* 2004) and Sanders et al. (*Circulation* 2005) describe approaches for identifying source(s) for variable atrial fibrillation (AF) as highly regular and rapid areas often using high spectral dominant frequency with a high regularity index. Other studies such as by Nademanee et al. (*J Am Coll Cardiol* 2004) suggest that complex fractionated atrial electrograms (CFAE) may be critical regions for AF. Other studies such as Cuculich et al. (*Circulation* 2010) used body surface imaging to show predominantly disorganized transient activation patterns and, rarely, a source region. In clinical use, such methods have produced disappointing results in guiding ablation in many studies (for instance, Verma et al., 2015; Wong, 2015, and others).

The prior art has recently described methods and systems to identify discrete sources for complex rhythm disorders including atrial fibrillation and/or ventricular fibrillation. See, e.g., U.S. Pat. Nos. 8,676,303 and 8,521,266 to Narayan et al., Narayan et al. (*J Am Coll Cardiol* 2012), Haissaguerre (*Circulation* 2014), and Krummen, et al. (*J Am Coll Cardiol* 2014). These systems show localized organized sources despite surrounding complex colliding waves and disorganization, with disorder reflecting additional competing sources, noise or other factors. Online systems are also now available to identify sources or drivers for complex rhythms (Al-Husseini, et al., *J. Cardiovasc. Electrophysiol.* 2017, 28:615-622). These studies found that using the same electrographic data, some analytic systems show stable sources while other systems show greater variability in sources (Alhusseini, et al. *J. Cardiovasc. Electrophysiol.* 2017; Zaman and Narayan, *Circ Arrhythm Electrophysiol* 2017; 10(12): e006022). However, it is unclear which patterns apply in some patients versus other patients, and hence how to optimize therapy to these different patient subtypes.

The prior art has described tools to mine biological data using machine learning technology. For example, Guyon, et al. (U.S. Pat. No. 7,542,947) teaches the incorporation of kernel-based learning machines such as support vector machines (SVMs) in a decision system that integrates data from heterogeneous, pre-existing data sources with genetic/proteomic and clinical data to facilitate identification and ranking of molecular markers for testing and treatment of disease. In Guyon, heterogeneous data sets may include gene or protein expression data, mass spectrometric data, antibody levels, clinical observations and history, drug, hormone, immunological testing, genetic and familial history, physical or chemical measurements, on-line journals, on-line genetic databases, and other sources. The method disclosed by Guyon is not specifically directed to guiding therapy, but rather to identification of molecular markers for diagnosis of disease.

U.S. Pat. No. 8,954,339 to Schaffer discloses a clinical decision support system (CDSS) with an inference engine that applies predetermined diagnostic and treatment rules to measured physiological parameters and patient tests to make recommendations for diagnosis and/or treatment based on expert knowledge and published studies. Added functions include identification of outliers in datasets that flag potential flaws in the inference engine that can lead to erroneous recommendations. Such decision support systems provide general decisions for known disorders, and do not teach or suggest solutions to problems that are not currently identified by experts. For instance, questions on whether a rhythm disorder will or will not respond to ablation, approaches to separate forms of atrial fibrillation, or forms of ventricular fibrillation that may be ablated rather than requiring a defibrillator, are currently unclear to experts, and therefore would not be available in a prior art CDSS. In addition, the prior art CDSS's may fail to recognize the clinical importance of symptoms or signs in individual patients, or the presence or absence of specific features of electrical data, specific features of structural data from computed tomography or magnetic resonance imaging, specific features of blood tests, genetic tests, or any other datasets.

A few prior art methods applied machine learning and neural networks to rhythm disorders, yet do not expand upon what is already known by experts, nor do they address questions critical for treatment. For instance, U.S. Pat. No. 5,819,007 to Elghazzawi and Chinese Patent Publication CN107203692A each disclose methods to detect AF using electrical data processed via neural networks that may provide high accuracy. As described in Chinese Patent Publication CN106066933A, this approach is expanded, disclosing a method for adding a weighted value matrix to an artificial neural network (ANN) to identify AF from a stored database (MIT-BIH database). In other studies, trained learning machines have been used to diagnose the presence of a disease, for example, malignant skin lesions, with accuracy comparable to dermatologists. See, for example, Esteva, et al. (*Nature* 2017), which uses deep convolutional neural networks (CNNs), or U.S. Pat. No. 8,543,519 to Guyon et al., which describes the use of SVMs to classify images of skin lesions as malignant or benign. Hannun, Rajpurkar, et al. *Nature Medicine* 2019 disclose the use of CNNs for detecting arrhythmias from the ECG with accuracy comparable to cardiologists. However, this prior art is less relevant to patients with already diagnosed AF because it does not improve upon knowledge known to experts, and hence does not advance treatment from the current suboptimal level. U.S. Pat. No. 7,171,269 B1 to Addison et al. describes the use of neural networks to adjust the timing of electrical shock therapy for fibrillation, but did not address ablation or drug therapy, or why they do not work in many patients. U.S. Patent Publication 2015/0042646 A1 to Comaniciu et al. discloses a computational model for arrhythmia in an individual, incorporating electrical and structural data to plan interventions. However, this model does not take into account relatively ineffective therapy such as the 40-60% success rate of pulmonary vein isolation for AF, or the 60-70% success rate of cardiac resynchronization therapy.

Many experts describe the need to integrate multiple approaches to diagnose, track or treat arrhythmia, such as combining invasive with non-invasive therapies, but this approach is rarely applied objectively or titrated using quantitative tools. For example, while weight loss can improve and reduce AF, it is not clear in which patients this is best applied, or if such individuals can be identified as a distinct group—since some obese individuals do not develop AF while many non-obese individuals do. This is also applicable to other lifestyle changes such as exercise, which can cause AF in cases of extreme exertion, while other patients with very sedentary lifestyles also experience AF. Inflammation may be a cause of many diseases including AF, but it is unclear how to integrate detection and/or therapy into overall management.

It would be of great benefit to society to develop an approach to personalize therapies that may work in an individual, even if they do not work in all patients, ideally covering a broad population. This may include individuals without and with identified genetic causes for their disease or response to therapy. This includes personal diagnosis to guide multiple forms of therapy quantitatively and, in some cases, to identify the precise cause of multifactorial disease in an individual person for therapy. One exemplary embodiment is for complex heart rhythms. Currently, there are few, if any, systems in the prior art to achieve these goals.

SUMMARY OF THE INVENTION

In an exemplary embodiment, the inventive method and system create personal digital phenotypes ("PDPs") of health and disease using one or more of a mathematic network using algorithmic, machine learning and probabilistic analyses, near-real-time data sensed from sensors, and previously-stored (historical) data, to guide personalized strategies to treat the disease and/or maintain health in an individual. Exemplary implementations include cardiac applications in heart rhythm disorders, in coronary artery disease and in heart failure.

The inventive technique is designed to automatically create personal phenotypes of biological and clinical significance that are currently unclear to experts, and thus represents a substantial advance over prior art CDSSs that approximate the performance of experts or may be based on approaches or rules by experts.

In application to heart rhythm disorders, complex rhythm disorders may produce patterns of heart activation that are difficult to understand by experts yet are clarified and treated by generating personal phenotypes from electrical, structural, and clinical data inputs to find the precise cause for therapy. This blended approach extends beyond traditional causes of rotational or focal drivers, or "random" wavelets, to comprise different electrical patterns of activation, or combinations of electrical patterns and structural or clinical data elements.

The inventive approaches described herein are well suited for complex diseases, including heart rhythm diseases, coronary disease, and heart failure, each of which is a heterogeneous syndrome rather than a single disease. In AF, for example, various electrical, structural, and metabolic mechanisms may contribute to its development and progression, each of which may differ between individuals. In principle, individualizing therapy ("personalized medicine") using a network constructed from a large set of sensed and archived input data (data elements), often from the electronic health record, in patients with diverse demographics and "traditional" phenotypes, trained by response or non-response to diverse AF therapies (each with defined mechanisms of action), may identify therapy-focused phenotypes and mechanisms of AF in each individual.

The inventive approach is further motivated by the lack of availability of detailed mechanism-based management for many complex organ functions due to several factors. First, conceptual knowledge of physiological contributions to heart rhythm disturbances, heart failure or even ischemia is limited. Second, there is inter-individual variability in said physiological contributions—for example, the impact of structural abnormalities may alter atrial fibrillation or heart failure in one individual versus another. Third, physiological interactions are often dynamic, and may respond to environmental changes. Dynamic changes may occur over years, months or even weeks to reflect normal or abnormal age-related change, or disease onset or regression, and may explain why management that initially works can become ineffective. Fourth, modulating this pathophysiology, even if defined, is often non-trivial. These limitations apply to multiple organ systems. It is, thus, a major challenge to modulate functioning of the heart or rest of the body a priori from known associations or physiological patterns.

Several innovations separate the current inventive approach from the prior art. First, it creates a quantitative personal digital phenotype (PDP), a digital bedside implementation of "personalized medicine" or "precision medicine," which does not require cellular or genetic data that may be absent in many diseases. Second, PDPs represent the combination of multiple data inputs, including readily available signals. These signals are not merely aggregated but are referenced against signals during adjudicated normal states in that individual, to partition health or disease. This may not require complex data inputs. Third, the approach creates novel digital taxonomy for a given disease or health state, using sensed data streams and/or input data elements (including from the electronic health record) in populations. Mathematical, statistical, and machine learning techniques are used to classify or partition these datasets to define quantitative forms of a disease process. The more detailed and broad, i.e., the "richer," the population data elements, the more comprehensive can be the computed digital taxonomy. In one embodiment, different hospitals contribute towards a de-identified large digital prospective registry of data, which will contribute different patient groups, practice patterns and data on outcomes from diverse therapies. Fourth, the inventive approach can adapt PDPs and taxonomies over time using updated data and computed fluctuations. Fifth, the inventive system utilizes novel sensors as well as existing healthcare machines which may operate separately or in combination (e.g., networked). Sixth, complex inputs can also be incorporated, including data from specialized medical equipment such as imaging systems, data streams from many sensors, in the individual or even from other individuals to enable crowd-sourced analyses. Seventh, phenotypes generated using the inventive approach enable tailoring of "personalized medicine." Finally, the system and method described herein provide a quantitative means to provide therapy via one or a combination of lifestyle changes, medications, electrical or mechanical therapy, surgical or minimally invasive ablation, genetic or stem cell therapy.

In the specific application to heart rhythm disorders, arrhythmias may be targeted using anti-inflammatory therapy, including immunosuppression using agents such as tacrolimus, a hitherto unrecognized form of therapy for complex arrhythmias such as atrial fibrillation. The inventive approach may therefore improve outcomes by eliminating repeat interventions—strategies with the highest predicted initial success can be designed and applied for a given individual at the outset, thus reducing cost and delays in treatment.

In one embodiment, PDPs are defined using multiple streams of sensed data and data elements from the individual. This is analogous to a mathematical representation of similar data in a population, which constitutes a novel disease taxonomy, enabling personalized management including therapy for the individual. The inventive approach utilizes directly sensed data and clinical data from diverse sources, digitally representing these data as a quantitative phenotype of cardiac state in that individual using deterministic and probabilistic methods including machine learning, and guide therapy using integrated or external devices. The inventive system has the ability to update the personal phenotype using repeated measurements over time, to tailor therapy in changing conditions, or to predict worsening or improvement in cardiac state. The inventive approach has broad applications that increase with the extent of data and number of updates over time, forming a rich digital portrait of health in the patient, individually and compared to a reference population. Personalized digital networks can also track homeostasis in a given organ system, to identify perturbations in disease, and normalization upon successful therapy. Data streams may be derived invasively or non-invasively from readily measured systems, including invasive recordings of electrical activity (electrograms), blood flow and pressure (hemodynamics), wall tension (cardiac contractility and relaxation), and related indices. Non-invasively, sensors may record from the electrocardiogram, cutaneous measures of nerve activity, and skin reflectance. Other types of sensed signals that may be used will be apparent to one of skill in the art.

Data types used within the inventive methods may be selected and sorted to represent different facets of a biological organ or process. In the heart, data streams comprise one or more of electrical signals, three-dimensional anatomical and structural abnormalities, clinical data extracted from history and physical examination, indices of pathophysiological comorbidities, blood and tissue biomarkers, and genetic and cellular makeup of an individual.

Candidate personal digital phenotypes are objectivized representations of pathophysiologic networks, representing indices derived from signal processing, associative algorithms, data clusters including those from unsupervised machine learning, and supervised networks trained by labeled events in similar and dissimilar individuals. Digital objects provide a comprehensive portrait of pathophysiology, using introspective analyses to pinpoint deficiencies within the network in disease and correction in health.

In one embodiment, the inventive method and system use machine learning to develop and learn classifications linking complex physiological and clinical inputs to outcome at a patient-level. This is then used prospectively to predict optimal therapy based on specific characteristics of the individual. The technique thus creates a novel patient-specific taxonomy for the disease, composed of digital phenotypes that may be used quantitatively to personalize therapy.

Applications of the inventive approach broaden with the richness of data inputs. Time-invariant and time-varying data streams are important inputs that may represent normal variations or disease states. Machine learning and deep neural networks in particular are considered most useful when the size of the networks is large, which is a desirable feature of this invention, and when the data repository is large, which is integral to creation of the digital taxonomy in this invention.

Data streams are multiple, designed to address limitations in the prior art that normal ranges, nomograms and clinical studies are often performed in individuals, ethnic groups, populations, or less well-defined disease states that may not reflect disease in the individual being treated. Multiple data streams are designed to help personalize the management and therapy. This may include familial tendency for disease (Mendelian or non-Mendelian), identifiable genetic loci, variations in weight, or susceptibility to toxins such as tobacco or alcohol. Other phenotypes may be clinically identifiable yet not tracked by a biomarker, or may have loose statistical definitions such as race or ethnic susceptibility.

Signals may be sensed without physical contact with a sensor. Examples include sensing a heartbeat from emitted electromagnetic fields from the magnetocardiogram (MCG), or from infrared signatures of cardiac motion.

Signals may also be sensed via physical contact with a sensor. Examples include motion sensing of chest wall movement from a breath or heartbeat, chest wall vibrations from certain types of breath (e.g., a loud obstructive breathing sound) or heart sound (e.g., a so-called "thrill" in the medical literature). Electromagnetic sensors can sense electromagnetic signals relating to the electromyogram (EMG), electroencephalogram (EEG), electrocardiogram (ECG) or other emitter. Breath sensors can detect movement of the chest wall, abdomen or other body parts associated with ventilation, or acoustic data (sound) associated with breaths, or oxygenation associated with breathing. Chemical sensors can detect chemical signals on the skin or other membranes that reflect body chemistry such as oxygenation and deoxygenation, metabolic acidosis, stress or other states that will be familiar to those skilled in the biochemistry arts. Sensors can also detect images using a camera or lens requiring contact from the fingerprint or other body part, or sense movement from specific muscles, or sense iris dilation or oscillations from photosensors in a contact lens. Positional sensors can identify position of body parts and changes over time (including gait) or contact sensing of the position of certain body parts at one point in time or over time (e.g., a facial droop, a facial tick or other idiosyncratic movement).

Less commonly used sensors include those used to detect inflammation. In prior art, the significance of inflammatory findings is often unclear in any given person at one point or over time, and between people. The "inflammosome" may measure the impact of inflammation from various pathological insults at the cellular or tissue level, yet is not commonly done, may not assess diurnal fluctuations, may have an unclear relationship to inflammatory state for the whole body, and may have unclear difference between individuals i.e., it is unclear how to establish "nomograms", or normal or abnormal states. This is another area for disease tracking and treatment well suited to personalized digital phenotypes.

In the current invention, a personalized state of inflammation may be detected by the presence of inflammatory cells in the primarily-inflamed organ system, or in body fluids such as the blood, urine or cerebrospinal fluid. The byproducts of inflammation can also be detected by elevated concentrations of biomarkers and cytokines such as interleukin-6, nerve growth factor, matrix metalloproteinases. On the other hand, a wide variety of physiological markers are abnormal in the context of inflammation (so called "acute phase reactants"). Inflammation causes, in addition to elevated white cell counts, abnormalities in red cell count, in hemoglobin concentration, and in a myriad of acute phase reactants such as C-reactive protein, erythrocyte sedimentation rate or white cell counts. In the heart, it is well known that serum troponin, a marker of cardiac cell destruction, is an acute phase reactant whose levels fall with inflammation ('inverse acute phase reactant').

For a preferred embodiment of heart rhythm disorders such as atrial fibrillation, immunosuppression therapy (as used for transplantation), steroids or non-steroidal agents, or cell therapy may be effective. The rationale for this embodiment is that patients after heart transplant who receive immunosuppressive agents rarely develop AF. This benefit is attributed to isolation of the pulmonary veins by surgical scar, yet for other populations isolation of the pulmonary veins provides at best 50-70% freedom from AF. In support of this inventive notion, inflammation has been implicated as a cause of AF for lone AF and AF related to obesity, pericardial fat, or oxidative stress from reactive oxygen species. However, the use of immunosuppression for complex rhythm disorders including AF has rarely if ever been implemented. Using the inventive approach, digital taxonomies and PDPs will identify individuals with likely inflammatory mediated arrhythmias in whom anti-inflammatory therapy including immunosuppression may be useful.

The inventive system may sense data signals from body systems using novel sensors. The sensed data streams may be combined with other data elements, sensed or detected by other systems in that individual, to create a digital network representation. The sensed signals from measurable body systems may include the central and peripheral nervous system, cardiovascular system, respiratory system, skeletal muscles and skin, and any other body system. Other input data elements may come from imaging, nuclear, genetic, laboratory, or other sources, and may also be sensed as a stream (i.e., transmitted to the system), or input as values at specific points in time.

In one aspect of the invention, a disease in a patient is identified and treated by collecting at least one data stream generated by at least one sensor configured to detect biological signals generated within a patient's tissue over time; acquiring patient data elements comprising one or more of demographic, clinical, laboratory, pathology, chemical, image, historical, genetic, and activity data for the patient; processing the at least one data stream and the acquired patient data elements by a processing module configured to execute a partitioning algorithm to generate a personalized digital phenotype (PDP); comparing the PDP to a digital taxonomy constructed from prior data to classify the patient into one or more quantitative disease classifications; and personalizing treatment for the patient based on the one or more quantitative disease classifications. In some embodiments, the at least one sensor is in physical contact with the patient's body and the data stream is transmitted by one of wired or wireless communication. The sensor may be one or more of an electrode, an optical sensor, a piezoelectric sensor, an acoustic sensor, an electrical resistance sensor, a thermal sensor, an accelerometer, a pressure sensor, a flow sensor, and an electrochemical sensor. The biological signals may include one or more of electrical heart signals, mechanical heart signals, heart rate, heart sounds, breathing sounds, breathing rate, breathing volume, nerve activity, and immunological signals. The patient data elements may include one or more indexes of electrical signals, hemodynamic data, cardiac structure from imaging, clinical factors associated with heart or lung conductions, nerve signals, genetic profile, biomarkers of metabolic status, and patient movement.

The inventive method may further include, prior to processing, applying a time stamp to each of the at least one data stream and the patient data elements. The partitioning algorithm may be one or more of supervised machine learning, neural networks, correlation analyses, logistic regression analyses, decision trees, time domain analyses, frequency domain analyses, trigonometric transformations, logarithmic transformations cluster analysis, and unsupervised machine learning. The digital taxonomy may include prior data of the patient. The one or more quantitative disease classifications may be one or more of rotational or focal activation patterns, intermittent rotational or focal activation patterns, incomplete activation patterns, and sites of specific heart structure or specific anatomical sites in said individual. The patient's tissue may be a heart, nerves that supply regions of the heart, regions of the brain that control the nerves, blood vessels that supply regions of the heart, and tissues adjacent to the heart. In some embodiments, the disease may be a heart rhythm disorder comprising one or more of atrial fibrillation, ventricular fibrillation, atrial tachycardia, atrial flutter, polymorphic or monomorphic ventricular tachycardia, ventricular flutter, or other electrical disturbance within the heart. In such embodiments, the method may further include, prior to processing, generating a map using the at least one data stream, where the map is an image representative of activations at locations within the heart, and where processing includes identifying locations of relatively higher activation. In other embodiments, the data stream is clinical electrograms including false deflections, and processing further includes generating a reconstructed electrogram using a machine learning algorithm trained on one or more reference signals associated with different heart rhythms.

In some embodiments, the personalized intervention may include modifying at least a portion of the patient's tissue by one or more of ablation by energy delivery via contact devices, energy delivery by noncontact devices, electrical therapy, thermal therapy, mechanical therapy, delivery of drug therapy, delivery of immunosuppression, delivery of stem cell therapy, and delivery of gene therapy. The method may further include generating updated personal historical data for the PDP, the classified one or more quantitative disease classifications, the personalized intervention, and an intervention outcome.

In another aspect of the invention, a system for identifying and treating a disease in a patient includes at least one sensor configured to detect biological signals generated within a patient's tissue over time and generate at least one data stream; and a computing device configured to: collect the at least one data stream; collect patient data elements comprising one or more of demographic, clinical, laboratory, pathology, chemical, image, historical, genetic, and activity data for the patient; process the at least one data stream and the patient data elements in a processing module configured to execute a partitioning algorithm to generate a personalized digital phenotype (PDP); compare the PDP to a digital taxonomy comprising stored prior data to classify the patient into one or more quantitative disease classifications; and determine a personalized intervention for treating the patient based on the classified one or more quantitative disease classifications.

In some embodiments, the at least one sensor is in physical contact with the patient's body and the data stream is transmitted by one of wired or wireless communication. The sensor may be one or more of an electrode, an optical sensor, a piezoelectric sensor, an acoustic sensor, an electrical resistance sensor, a thermal sensor, an accelerometer, a pressure sensor, a flow sensor, and an electrochemical sensor. The biological signals may include one or more of electrical heart signals, mechanical heart signals, heart rate, heart sounds, breathing sounds, breathing rate, breathing volume, nerve activity, and immunological signals. The patient data elements may include one or more of electrical signals, hemodynamics, cardiac structure from imaging, clinical factors associated with heart or lung conductions, nerve signals, genetic profile, biomarkers of metabolic status, and patient movement.

The inventive system further includes the computing device, prior to processing, applying a time stamp to each of the at least one data stream and the patient data elements.

The partitioning algorithm may be one or more of supervised machine learning, neural networks, correlation analyses, logistic regression analyses, decision trees, time domain analyses, frequency domain analyses, trigonometric transformations, logarithmic transformations, cluster analysis, and unsupervised machine learning. The digital taxonomy may include prior data of the patient. The one or more quanlitative disease classifications may be one or more of rotational or focal activation patterns, intermittent rotational or focal activation patterns, incomplete activation patterns, and sites of specific heart structure or specific anatomical sites in said individual. The patient's tissue may be a heart, nerves that supply regions of the heart, regions of the brain that control the nerves, blood vessels that supply regions of the heart, and tissues adjacent to the heart. In some embodiments, the disease may be a heart rhythm disorder comprising one or more of atrial fibrillation, ventricular fibrillation, atrial tachycardia, atrial flutter, polymorphic or monomorphic ventricular tachycardia, ventricular flutter, or other electrical disturbance within the heart. In such embodiments, the method may further include, prior to processing, generating a map using the at least one data stream, where the map is an image representative of activations at locations within the heart, and where processing includes identifying locations of relatively higher activation. In other embodiments, the data stream is clinical electrograms including false deflections, and processing further includes generating a reconstructed electrogram using a machine learning algorithm trained on one or more reference signals associated with different heart rhythms.

In some embodiments, the personalized intervention may include modifying at least a portion of the patient's tissue by one or more of ablation by energy delivery via contact devices, energy delivery by noncontact devices, electrical therapy, thermal therapy, mechanical therapy, delivery of drug therapy, delivery of immunosuppression, delivery of stem cell therapy, and delivery of gene therapy. The computing device may be further configured to generate updated personal historical data with the PDP, the classified one or more quantitative disease classifications, the personalized intervention, and an intervention outcome.

A significant advantage of the inventive approach is its ability to analyze streams from other individuals, with similar or dissimilar profiles to the current patients, to enable a digital taxonomy to be created and updated via crowdsourcing.

In one aspect, the inventive system includes a processor and a memory storing instructions that, when executed by the processor, performs operations including detecting bodily signals associated with one or more bodily functions at one or more sensors associated with the human body, processing the bodily signals to create one or more sensed signatures, processing the signatures using the digital object to determine an effector response, delivering one or more effector responses to control a bodily task and monitoring said response.

A preferred embodiment relates to heart rhythm disorders. Using electrical signals, the inventive system can identify causes for a rhythm disturbance personalized by statistical measured and inferred data on said individual, to provide accurate targets for therapy that extend the prior art. Combining electrical signals with anatomical, clinical or other data, the network identifies deficiencies in the cardiacphysiological network enabling personalized therapies to treat heart rhythm disorders in an individual. In this embodiment, the onset of heart rhythm disorders can be predicted and, once initiated, their sources can be identified to guide invasive or non-invasive therapy.

In summary, the present invention uses multiple sensed and input data to create personalized digital phenotypes, which are compared to digital taxonomies from similar and dissimilar individuals, including those with known outcomes, and applied as a digital personalized medicine strategy to maintain health, or therapy to correct disease. Preferred embodiments, which are not intended to be limiting, include cardiac applications in heart rhythm disorders, in coronary artery disease and in heart failure.

BRIEF DESCRIPTION OF THE DRAWINGS

Some embodiments are illustrated by way of example and not limitation in the figures of the accompanying drawings in which:

FIGS. 3A and 3B provides circuit schematics for an exemplary device that senses signals for analytic processing of personal digital phenotypes (PDPs).

FIG. 12C illustrates reconstructions according to an embodiment of the inventive method, FIG. 12D diagrammatically illustrates application of the inventive approach to different clinical signals, and FIG. 12E illustrates application of the inventive scheme to reconstruct signals.

FIG. 14A shows AF maps segmented into rotational and non-rotational regions and a plot of neural net accuracy on a testing set arrhythmia maps of AF; FIG. 14B shows a sample embodiment of interpreting machine learning for AF maps; FIG. 14C shows accuracy of the interpretability analysis for locating causes of a heart rhythm disorder; and FIG. 14D shows possible displayed content for user interfaces/mobile devices.

DETAILED DESCRIPTION OF EXEMPLARY EMBODIMENTS

Figure 1:
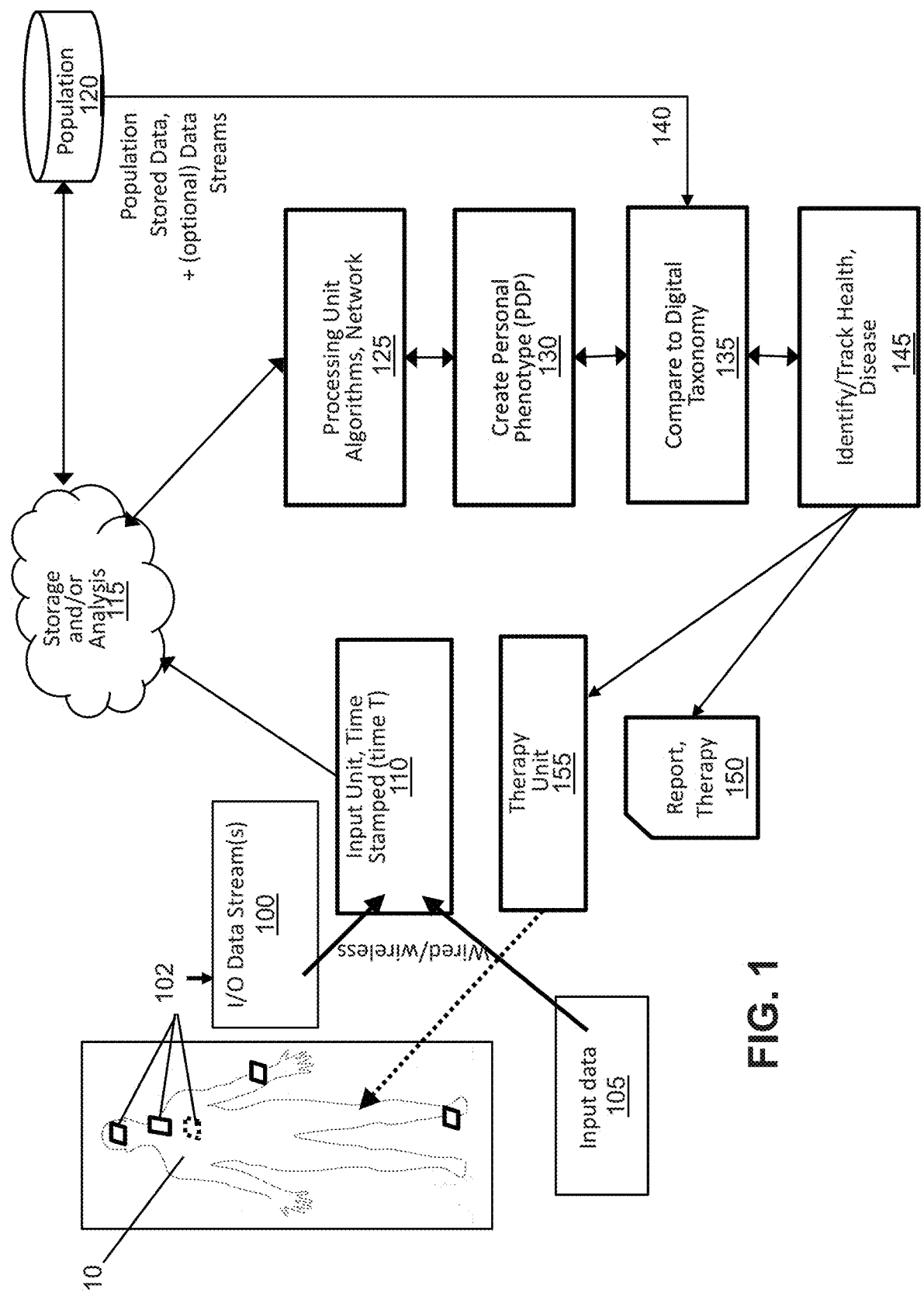
FIG. 1 is a block diagram with an overview of an embodiment of the invention for digital taxonomy and phenotype-specific therapy

For the purposes of this disclosure, the following definitions apply:

"Associative learning" means the process of linking input data with a measurable physiology or clinical outcome. Associative learning may be iterative, enabling associations to be modified ("learned") based upon patterns of change between input and measured output (physiological or clinical endpoints).

"Biological signal" means a signal is produced by the body, and can reflect one or more bodily systems. For instance, the heart rate reflects cardiac function, autonomic tone and other factors. See also non-biological signal.

"Biometric signals" mean signals that provide metrics of human characteristics. Biometric identifiers can be physiological or behavioral. Physiological biometrics include, but are not limited to DNA, fingerprints or palm prints, mouth swabs, tissue or urine samples, retinal images, facial recognition, geometry of the hand or foot, recognition of the iris or odor/scent of an individual. It can also be applied to signals such as vital signs, the ECG, the EEG, EMG, and so on. Behavioral biometrics include patterns such as gait during walking or typing rhythm. Embodiments of the invention use dynamic patterns of combined physiological and behavioral biometrics over time, which adapt to changes in the individual and are thus robust to forgery from prior "versions" of a person's signature.

"Body" means the physical structure of a single-celled organism, a multi-celled organism, viruses, and prions. Organisms include animals (such as, but not limited to, humans and other mammals), plants, bacteria, etc.

"Consumer device" means a device that is available directly to a consumer without a medical prescription. Historically, such devices typically were not regulated by a medical regulatory agency or body, such as the U.S. Food and Drug Administration or similar regulatory bodies in other countries, however, more recently, some devices are FDA cleared. A Consumer device may include hardware, software, or a combination thereof. It is typically not a medical device, the latter being defined as an instrument, apparatus, implement, machine, contrivance, implant, in vitro reagent, or other similar or related article, including a component part, or accessory, which is intended for use in the diagnosis of disease or other conditions, or in the cure, mitigation, treatment, or prevention of disease, in man or other animals. The definition of a medical device excludes medical decision support software.

"Effector" is a means of performing a bodily task, and may include a physical appliance, prosthesis, mechanical or electronic device. A physical appliance may enhance a bodily function, such as a device to move a limb or move the diaphragm to enhance breathing during sleep or a splint to keep the airway open during sleep, or one or more signals to stimulate a bodily function, such as electrical stimulation of the phrenic nerve to enhance breathing during sleep, or an artificial prosthesis such as a cybernetic limb or implanted circuit for the peripheral or central nervous system.

"Data streams" or "streams(s) of data" mean biological data sensed by one or more sensors that can provide real-time or near-real-time information on the biological process being sensed. Sensors in the heart may provide streams comprising the electrocardiogram (ECG), pulse rate, pulse waveform and hence cardiac hemodynamics. Other data streams may include cardiac acoustics, including analysis of heart sounds, murmurs and sophisticated analyses of hemodynamics related to the heart. Lung function may be sensed as chest movement, auscultatory sounds and nerve firing associated with breathing. Gastrointestinal disease may be sensed as sounds (borborygmi), movement on the abdominal wall, and electrical signals related to smooth muscle activity of the gut. Central and peripheral nervous system activity may be sensed as nerve activity on the scalp (electroencephalogram, EEG), remote from the scalp but still reflecting the EEG, and from peripheral nerve firing.

"Demographics", as used herein, means clinically relevant personal information, which may include, but is not limited to, age, gender, family history of disease, and presence of comorbidities.

"Digital taxonomy" means a partition of different states of disease or health based on quantitative indices. Traditional disease classifications may state "atrial fibrillation is more common in the older individuals, those with heart comorbidities such as valvular lesions or heart failure, those with metabolic syndrome". Conversely, digital taxonomy is designed to be quantitative, describing an individual's health for a particular disease in terms of quantifiable primary and secondary data elements (i.e., data vector). The likelihood that a disease entity $D_n$ is present in a specific individual is approximated by the probability $p(D_n)$:

$$p(D_n) = \sum_{i=1}^{m} \frac{(k_n p(V_{n,i}))}{k_n}$$

Where m is the number of available data input types, n is the disease being considered, and $p(V_{n,i})$ is the probability that data vector $V_{n,i}$ contributes to disease n for input i, and $k_n$ is a weighting constant for disease n. These elements are estimated by the digital taxonomy, which computes specific probabilities that a certain data input contributes to that disease. Probabilities can be obtained from population data, in which the specific person is matched to the closest individual from that population to estimate this probability. The probability can also be obtained from this specific individual alone, at likely or adjudicated times of health and, ideally, at likely or adjudicated times of disease. These calculations can be performed by traditional estimating equations but may also be formed by machine learning. In this way, the digital taxonomy represents a disease entity probabilistically from the aggregate of abnormalities in multiple related data inputs. This process is thus dynamic, since the taxonomic equation for any given disease will change as more data inputs are available, and as data streams change, particularly if the adjudicated disease state is updated accordingly. Thus, this digital taxonomy is well suited to analyzing massive amounts of data from wearable devices in an individual, or massive amounts of data from several individual as a crowd-sourced paradigm.

"Historical data" means stored data, which may include reports from medical imaging, e.g., magnetic resonance imaging (MRI), computed tomography (CT), radiological, or other scans of an organ, data from genetic testing analyses (e.g., presence of one or more genomic variants), previously-obtained ECG reports, pathology, cytology, and other laboratory reports, as well as clinical demographics such as age, gender, family history of disease, and presence of comorbidities. Historical data may further include additional personal historical details that could be relevant to generating the PDP, for example, mental illness, employment in a high-stress profession, number of pregnancies (in women), engaging in high-risk behaviors such as smoking, drug or alcohol abuse, etc.

"Input data" or "data input(s)" means data not directly sensed by a physical component of the system, but data that is utilized by the processing unit in conjunction with sensed data to generate the PDP and digital taxonomy. Input data from a data source may include streams of data detected using other systems, for example, an external ECG or EEG system, clinical, laboratory, pathology, chemical, or other data, or data from a medical imaging device, which data is transmitted to the processing unit.

"Machine learning" means a series of analytic methods and algorithms that can learn from and make predictions on data by building a model rather than following static programming instructions. Machine learning is often classified as a branch of artificial intelligence and focuses on the development of computer programs that can change when exposed to new data. In the current invention, machine learning is one tool that can be used to create the digital network linking sensed signatures with bodily tasks in each individual, i.e., for a personalized solution to maintain health and diagnose disease. Machine learning techniques include supervised learning, transfer learning, unsupervised learning, or reinforcement learning. Several other classifications may exist, but mostly embody the following concepts:

"Unsupervised Machine learning" includes methods such as cluster analysis that may be used to identify internal links between data, potentially such as the link between clinical data (diagnosis of atrial fibrillation), family history, data from physical examination (irregularly irregular pulse), data from sensors, electrical data (irregular atrial signals on the ECG), structural imaging data (enlarged left atria), biomarkers, genetic and tissue data as available.

"Supervised Machine Learning" includes methods that can classify a series of related or seemingly unrelated inputs into one or more output classes without explicitly modeling inputs, i.e., without assuming a potentially incorrect ("biased") mechanistic hypothesis.

"Reinforcement learning" is a form of machine learning related to psychology, which focuses on how software agents take actions in a specific environment to maximize cumulative reward. Reinforcement learning is often used in game theory, operations research, swarm intelligence and genetic algorithms and has other names such as approximate dynamic programming. One implementation in machine learning is via formulation as a Markov Decision Process (MDP). Reinforcement learning differs from supervised machine learning in that it does not require matched inputs and labeled outputs, and actions that result in sub-optimal rewards are not explicitly corrected (unlike supervised learning which may correct suboptimal rewards via e.g., back propagation algorithms in a perceptron).

"Medical device" means an instrument, apparatus, implement, machine, contrivance, implant, in vitro reagent, or other similar or related article, including a component part, or accessory, which is intended for use in the diagnosis of disease or other conditions, or in the cure, mitigation, treatment, or prevention of disease, in man or other animals. The definition of a medical device excludes medical decision support software.

"Neural networks" means self-learning networks of interconnected nodes modeled loosely after the human brain that can be used to recognize patterns. Artificial neural networks can be combined with heuristics, deterministic rules and detailed databases.

"Personal digital phenotype" ("PDP") means a digital combination of multiple data inputs and streams that represent a disease entity or facet of health in an individual. Data elements may represent the individual's health state directly or indirectly, weighted by their likelihood of contribution to disease or health of that individual of a certain age, gender and morbidities. Digital combinations and weightings are performed by algorithmic analyses that parameterize different elements into functional groups, by the calculated and documented probability of impact on health and disease. Combinations may comprise deterministic algorithms and forms of machine learning. For example, a heart rhythm phenotype will primarily consider heart rate and electrographic signals (surface ECG and intracardiac). Higher mathematical weighting will be given to these data elements. Data streams from other (indirect) organ systems may include changes in breathing rate with heart rate (i.e., lung sensors), changes in nerve firing with heart rate (i.e., nerve function). Other important data elements include abnormal cardiac ejection fraction, location and presence of structural abnormalities of the heart. Historical data including age, gender and family history may also impact the overall digital personal phenotype.

"Index individual" means a patient or target of a study or evaluation for whom a personal digital phenotype may be generated.

"Population data" as used herein is a key determinant of the accuracy of the inventive approach. If the reference population is very different from the index individual then the digital taxonomy may not include individuals of this phenotype—and may or may not represent him or her. In this case, the population data and digital taxonomy is primarily derived from prior adjudicated data in the individual—i.e., data points when the individual was well, and when he or she was not well. If the reference population is broad and inclusive but not well phenotyped or well-labeled for data elements contributing to this disease, then again the taxonomy will not be useful. Thus, the ideal data set is not 'large-scale' or 'big-data' collections using ubiquitous sensors which are not well labeled nor in well-defined populations. Instead, the ideal data set comprises parallel data streams that can be self-organized via clustering to partition different classes within the digital taxonomy.

"Sensors" include devices that can detect biological signals from the body of an individual. A sensor may be in direct contact with the body or may be remote. When applied to a group of individuals, sensors may represent all or part of a defined population. Sensors can detect electrical information, such as voltage or current representing the ECG, EEG, EMG, or nerve firing. The term "sensor", especially when describing certain cardiac applications of the invention in which electrical information is detected, may be used interchangeably with "electrode", "electrode catheter", or "catheter." Electrical sensors can also detect bioimpedance, such as conductance across the skin that decreases when the person perspires, which may occur during times of sympathetic nervous system predominance. Sensors can also detect other chemical changes via current flows. Sensors also include devices that detect temperature, such as a thermistor or other thermal detector. Sensors can detect light such as changes in the color of reflected light form pulsatile heart activity (photoplesthysmography), changes in peripheral oxygenation (e.g., cyanosis, anemia, vasodilation on the skin). Sensors can detect sound via a microphone. Sensors can detect other vibrations or movement via piezoelectric elements. Sensors can detect chemicals directly, using specialized sensors for hormones, drugs, bacteria and other elements which are typically transduced on the device to an electrical signal. In exemplary embodiments of the inventive system, multiple sensors may be used in communication with a central computing device or which may form a network linked via BLUETOOTH®, WiFi™, or other protocol to form an internet of things (IoT) of biological sensors.

"Signals" include electronic, electromagnetic, digital or other information that can be sensed or acquired. Sensed signals are detected unaltered from their natural form (i.e., recorded) with no transformation. Sensed signals are typically biological signals. Sensed signals can be detected by humans (e.g., sound, visual, temperature) but also machines such as microphones, auditory recorders, cameras, thermometers). Acquired signals are detected in a transformed state, such as an ECG recording. Such signals may be biological, since cardiac bioelectricity generates the ECG, or non-biological signals, e.g., vibration sensed after application of sonic or ultrasonic energy, or a haptic signal transduced from a sensed electrical, sonic or other signal.

"Smart data" means application-specific information acquired from sources that can be used to identify and/or act upon normal or abnormal function in an application. Smart data is thus different from the term "big data". "Smart data" is tailored to the individual, and tailored to address the specific task or application—such as to maintain health and alertness or detect and treat disease such as sleep disordered breathing. Tailoring is based on knowledge of what systems may impact the task in question. Such knowledge may be based on physiology, engineering, or other principles. Conversely, "big data" is often focused on extremely large datasets for the goal of identifying statistical patterns or trends without an individually tailored link. In machine learning parlance, smart data may result from supervised learning of datasets to a known output, while big data simply speaks to the volume of data without necessarily implying any knowledge of significance of specific datasets.

Other biological terms take their standard definitions, such as heart failure, tidal volume, sleep apnea, obesity and so on.

The following description and accompanying figures provide examples of applications of the inventive system and method for creating personal digital phenotypes (PDP) of health and disease, compared to digital taxonomies to enable personalized strategies to treat disease and/or maintain health in an individual are disclosed herein. The examples described herein are intended to be illustrative only. As will be evident to those of skill in the art, additional variations and combinations may be formed employing the inventive principles disclosed herein.

FIG. 1 illustrates the flow within an exemplary system to define personal digital phenotypes, compare them to a digital taxonomy, and design personalized therapy. The personal I/O data stream 100 takes time-varying (dynamic)

data from the index individual 10 (the patient), via signals sensed at one or more sensors 102, which may be external devices (solid lines) or internal (implanted) devices (dashed lines). Implanted devices may be inserted expressly for the purpose of developing/maintaining the PDP, or implanted for a different purpose. Such devices may communicate using an Internet of Things (IoT), with time-stamped data being sent to the input unit 110. Such data may be sent via connected or wireless means, and may be continuous, near-continuous, real-time, near-real-time or some other format of time-acquired signals.

Deviations from normal can be quantified in the index individual compared to his/her own data, beyond pre-specified "tolerance limits", and compared to different populations. In a preferred embodiment, this is accomplished by sensing data streams 100 or acquiring data on a repeated basis. The data streams may be acquired using novel, consumer, or medical grade sensors. Data may be input from several sources during periods of adjudicated "health" for that organ system in that person, and similarly during periods of adjudicated reduced health/"disease". The accumulated data assists future supervised learning to validate digital phenotypes. Different states may be detected for altering conditions or grades of health or disease (for instance, exercise versus rest) for and between individuals. This approach differs from current medical practice, in which a "population" range for "normal" and "disease" is applied across multiple patients with little scope to tailor them to the individual. This aspect of the invention enables "personalized medicine" or "precision medicine".

Input data 105 may include demographics, laboratory, chemistry, and image data. For example, important data inputs for a person may include "static" stored data, such as date-of-birth (age), gender and race. Input data 105 may also include near-real-time data such as patient movement from a separate device (e.g., a treadmill, motion sensor in a building), patient ECG or cardiac information from separate device (e.g., hospital telemetry, ICU bed monitors), breath sensors, time-lapse or time-series data from a separate device (e.g., periodic counts of blood sugar from a glucometer), or other data input. The input data 105 are also sent via wired or wireless connection to input unit 110, with time-stamp s.

Conventional cloud-based computing/storage 115 may optionally be used to store data in addition, or as back-up, to that stored on devices in 100 or 105, and/or to perform processing of the data. Raw data and analysis results saved or generated in cloud-based computing/storage may be separately communicated to external servers connected via the Internet (connection not shown). For example, independent recipients may include a research facility, clinical trial administrator, or other recipient authorized by the patient.

Population database 120 provides a mathematical reference for the personal data and may include population stored data, and optional data streams. The data in this database may take the form of time-varying streamed data, but may also include accumulated and stored data from a database.

The processing unit 125 is programmed to execute algorithms that include deterministic formulae as well as neural networks (or other learning machines) and other distributed representations to create a personal digital phenotype (PDP) in step 130 and compare the PDP to a digital taxonomy in step 135, which comprises data from prior adjudicated timepoints for the index individual 10 as well as data from population database 120. In one embodiment, machine learning is used to process input data, develop and learn classifications linking complex physiological and clinical inputs to outcome at a patient-level (i.e., develop PDPs), compare these to quantitative traits in a relevant population (a digital taxonomy of health or disease), and prospectively design "optimal" or "personalized" therapy based on specific characteristics of an individual relative to prior observations in the individual, prior observations in the comparator population, or mathematically inferred predictions.

The comparison performed in step 135 is used in step 145 to identify and/or track the patient's status, i.e., health or disease. The status information is communicated in step 150 to a unit for display, e.g., a smartphone app, a dedicated device, or existing medical device. The health/disease information can be used to guide therapy via a therapy unit 155. The therapy unit 155 in an embodiment for use with heart rhythm disorders comprises delivering electrical intervention (pacing) or destructive energy (ablation) to tissue that subtends an electrical and/or structural target for the arrhythmia determined via personalized digital phenotypes. Other therapy units may deliver anti-arrhythmic drugs using an infusion pump, delivering anti-inflammatory therapy since inflammation may be a proximate cause of heart rhythm abnormalities such as fibrillation, or delivery of gene or stem cell therapy. In another embodiment, therapy to deliver mechanical constraint can be delivered, to ameliorate stretch which can trigger arrhythmias.

Figure 2:
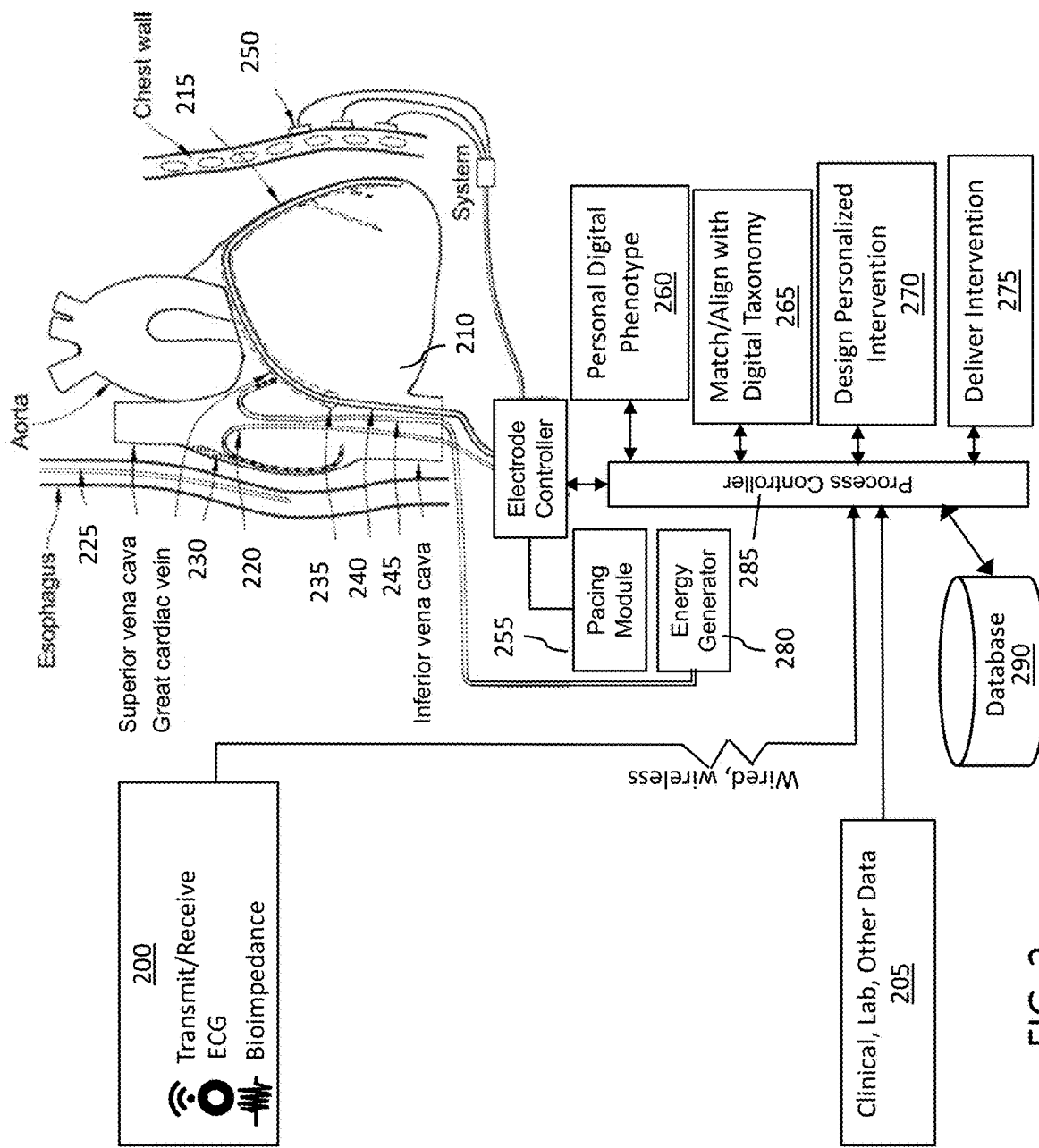
FIG. 2 is a diagram of an embodiment of the inventive system with cardiac application integrating data streamed from the heart or related organs with input data from many clinical sources.

FIG. 2 illustrates an exemplary system for defining personal digital phenotypes in the heart, specifically for heart rhythm, using sensors 200 or input streams 205 including clinical, laboratory, genetic or other data, compare them to a digital taxonomy, and deliver personalized arrhythmia therapy.

The heart 210 can be measured in many ways including electrical or electromagnetic signal sensors such as electrode catheters 225 in the esophagus, electrodes 230 in the right atrium 230, electrodes 220 in the septum or left atrium, or via the great cardiac vein to various locations in the coronary sinus (electrodes 235, 240, 245), to the anterior cardiac vein (electrode 215) that accesses the left or right ventricle, or directly to any of these chambers. ECG electrodes can be applied to the body surface 250. Electrodes can also reside in other blood vessels or at other locations in proximity to the heart 210. These electrodes are configured to detect cardiac activation information in the heart and to transmit the detected cardiac activation information via the electrode controller to the process controller 285. Data may be transmitted by wired or wireless means.

In some embodiments, one or more of the sensors may be external to the patient's heart. For example, sensors 250 detect cardiac activation via the patient's surface (e.g., electrocardiogram—ECG). Other sensors (not shown) may detect cardiac activation remotely without contact with the patient (e.g., magnetocardiogram). As another example, some sensors may also derive cardiac activation information from cardiac motion of a non-electrical sensing device (e.g., echocardiogram, Doppler signals of blood flow, red cell tagged scans). Such sensors can generally be classified as "external sensors" to distinguish them from catheters and electrodes that are inserted into the patient's body, into or near the heart (or other organ), i.e., "internal sensors." In various embodiments, a variety of external sensors may be used separately or in different combinations, and further these separate or different combinations of external sensors can also be used in combination with one or more internal sensors.

Additional sensors may be provided to detect abnormal inflammatory or immunological states of the body, enabling modulation of such states to maintain, enhance or correct biological rhythms. In an embodiment for cardiac applications, sensors are provided for detecting abnormal immunological state and modulating it to prevent or treat the complex heart rhythm disturbances of atrial fibrillation or ventricular fibrillation.

Inventive steps may include but are not limited to sensing direct and indirect measures of "immunological state," sensing these metrics iteratively, comparing metrics in an individual to normal and abnormal values in that individual rather than a population-based metric, and directing interventions and therapy to maintain normal immunological equilibrium or correct impaired equilibrium. In this context, "sensing" of metrics goes beyond a traditional interpretation of collecting raw signals and data from a detection device, and may include data generated from other test procedures, e.g., clinical, laboratory, chemical, etc., and inputting the test data into the process controller 285. As shown in FIG. 2, information may be generated by devices 200 that sense electrical signals, for example, ECG or bioimpedance sensors, combined with a transmitter for communicating the detected signals to process controller 285, either through wired or wireless transmission. Other sources of streamed or input data 205 obtained from clinical systems, hospital databases, hospital devices, or laboratory equipment may also provide input to process controller 285, either through wired or wireless transmission.

Direct measures of inflammatory/immunological equilibrium include, but are not limited to, counts of inflammatory cells or concentrations of cytokines in body fluids or in an affected organ. Indirect measures of inflammatory/immunological equilibrium represent the protean impact of inflammation on various organ systems abnormalities in static and diurnal measures of body temperature, body fluid composition, heart rhythm, nerve firing rates, and the encephalogram.

Sensors 215-245, positioned at sensor locations in the heart of the index individual, can further detect cardiac activation information at their respective locations and can further deliver energy to ablate the heart at the sensor locations. It is noted that sensors 215-245 can also detect cardiac activation information from overlapping regions of the heart (e.g., right atrium and left atrium 220).

The process controller 285 may include a digital signal processor to interface with output elements configured to stimulate different parts/nerves of the body, or cause mechanical action in an external machine. Such elements could include traditional computing machines with integrated circuits in isolation or networked (e.g., cloud computing), biological computing, integrated biological/artificial devices (cybernetic) or utilizing unused biological capacity to perform specific, directed tasks. Therapy devices may include direct electrical outputs, piezoelectrical devices, visual/infrared or other stimulatory systems, nerve stimulating electrodes or even virtualized data such as avatars in a virtual world interface or elements in a large database that can be queried, as well as other effector elements evident to those skilled in the art.

The process controller 285 is configured to process (e.g., clarify and amplify) cardiac activation information generated by the various input sources (sensors 200, input data source(s) 205, sensors 215-245) into cardiac signals of electrical, mechanical or other function, and to provide the processed signals to the process controller 285 for analysis in accordance with methods disclosed herein. Referring briefly to FIG. 1, the functions corresponding to input unit 110 and processing unit 125 would be among the computing operations executed within process controller 285. In processing the cardiac activation information from sensors 200, 215-245 and input data source 205, the processing controller 285 can subtract cardiac information from overlapping regions of the heart to provide processed signals for analysis. In some embodiments, the process controller 285 is configured to analyze unipolar signals; in other embodiments, the process controller 285 analyzes bipolar signals, and in other embodiments motion, optical, other electromagnetic signals are analyzed.

The process controller 285 is programmed to implement functional modules to generate personalized digital phenotypes of cardiac (rhythm) in the individual (PDP module 260, which corresponds to step 130 in FIG. 1), match or align the PDP with digital taxonomy (taxonomy module 265, corresponding to step 135 in FIG. 1) using data from population database 290, to design personalized interventions (design module 270) and guide delivery of intervention through intervention module 275.

In some embodiments, the process controller 285 analyzes signals in accordance with readily available methods or those disclosed herein such that it is possible to generate a map(s) (representation(s)) of indices of cardiac activation which can be used to locate a source(s) of the heart rhythm disorder and to eliminate the source(s). The map(s) can then be displayed on an output device and saved in a database with the PDP.

Population data 290 is configured to support or aid in the analysis of signals by the process controller 285. In some embodiments, the database 290 can store maps of potential AF source locations for other individuals of known de-identified personal digital phenotypes, which can be used to guide therapy in this individual (if phenotype is similar) or guide therapy away from this region (as suggested by phenotypes and taxonomy.) The population database 290 can also be used to store intermediate data.

Once the appropriate therapy has been designed in design module 270, it can be delivered. For example, using the personalized intervention, instructions will be generated by the intervention module 275 causing the process controller 285 to deliver pacing from a pacing module 255. In another example, the existing internal electrodes (e.g., sensors 215, 230-245, can be used to deliver ablation energy from energy generator 280 as controlled by process controller 285 and intervention module 275. Other forms of energy may also be delivered, e.g., heating, cooling, ultrasound, laser with the use of appropriate therapy devices controlled by the process controller and intervention module 275. Therapy is delivered to tissue that subtends an electrical and/or structural target for arrhythmia determined via personalized digital phenotypes. Other therapy units may deliver anti-arrhythmic drugs using an infusion pump, delivering anti-inflammatory therapy since inflammation may be a proximate cause of heart rhythm abnormalities such as fibrillation, or delivery of gene or stem cell therapy. In another embodiment, therapy to deliver mechanical constraint can be delivered, to ameliorate stretch which can trigger arrhythmias. Therapy may also include external radiation, enabling a fully non-invasive therapy in which energy is focused at critical targets for arrhythmia inside the heart using high energy electromagnetic radiation.

One category of sensed signals is from the heart. This is a preferred embodiment of the invention, and may comprise several heart signal types. Electrical activity can be sensed from the heart directly using sensors that may be placed on the heart and either in contact or not, sensors near other body regions (e.g., esophagus, bronchi and airways, mediastinum), on the body surface, or not touching the body such as magnetocardiography that senses magnetic fields generated by heart electrical activity. Sensors may measure cardiac function, motion, electrical activation patterns or presence of ischemic regions by detecting cardiac motion or the movement of blood through it. Cardiac motion can be sensed using non-electrical devices e.g., echocardiogram or ultrasound, from movement on regions of the body from cardiac motion (ballistic cardiography), from electrical impedance change due to alterations in heart chamber volumes. Blood flow can be detected from e.g., Doppler echocardiography, 4D-flow MiII, imaging methods that tag a carrier such as red cells. In various embodiments, these sensors can be used separately or in different combinations, and further these separate or different combinations can also be used in combination with sensors inserted into the patient's heart.

Nerve activity is an example of another sensed signal that may be used in an embodiment of the invention, with indices such as rate and periodicity of firing, periodicity during the day and between days, types and patterns of nerve firing, and spatial distribution of these measures. In one embodiment, non-invasive recordings are made from skin patches, but other embodiments could use the electroneurogram (ENG) where an electrode is plunged into the skin to record from nearby neural tissue. Invasive approaches may be suitable for inpatient care but less suited for continuous recordings or consumer applications. Sensors can record from different regional nerves if placed in different regions, e.g., electrodes on the chest may measure nerve activity related to the heart or its nerves, electrodes on the neck or head may measure neural signals including those controlling the heart, or other locations familiar to one skilled in the art.

Lung (pulmonary) function activity is an example of another type of sensed signal, and may vary independently of the heart, or as a result of alterations in the heart. This can be measured by sensors of breath sound, chest wall movement, oxygenation, electrical activity of the phrenic nerve or other sensors.

Figure 3A:
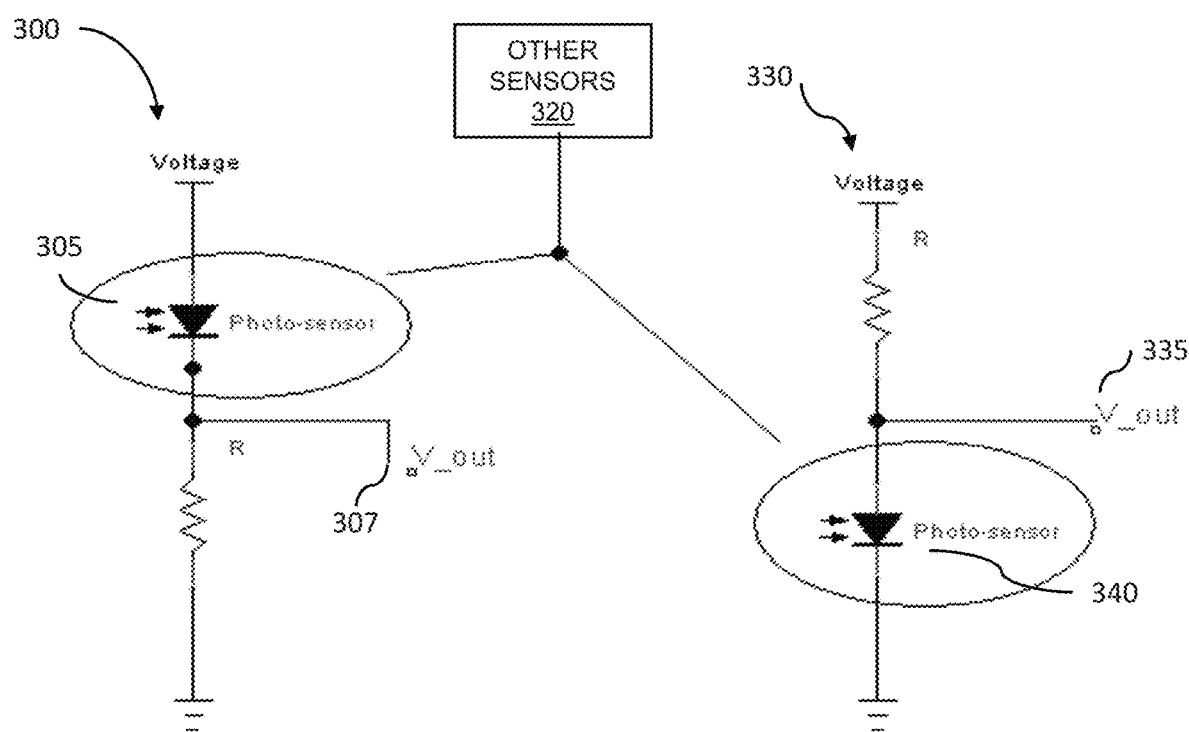

FIGS. 3A and 3B provide examples of devices that may be used in conjunction with analytic elements and personal digital phenotypes in embodiments of the invention. FIG. 3A provides simple circuit diagrams for exemplary sourcing 300 and sinking 330 circuits. For the sourcing circuit 300, the power supply is preferably low power for a wearable or portable device. In the illustrated example, an integrated photo-sensor 305 is included to detect optically-detectable signals, however, as will be apparent to those of skill in the art, other sensor types 320, e.g., piezoelectric, acoustic, electrical resistance, thermal, accelerometers, pressure, flow, electrochemical, or other sensor types may be used to measure chemical, light, skin activity/moisture levels, pressure, movement, and other parameters relevant to development of the PDP. Sensors can be interchangeable or fixed in each hardware embodiment. Selection of appropriate component values (resistors, capacitors, etc.) and circuit performance characteristics, as well as addition of supporting components/circuitry (filters, amplifiers, etc.), will be within the level of skill in the art and are not described herein. Voltage output 307 provides a signal to the input channels for streaming data, e.g., to I/O data stream 100 in FIG. 1. For the sinking circuit 330, a photosensor 340 is illustrated, with output voltage 335 being transmitted to the I/O data stream.

FIG. 3B provides further detail for a preferred embodiment of the device. This embodiment connects sensors to logic circuits, which process the signal(s) combinations for optimal use for personal digital phenotypes, and transmit raw or processed signals to another computing device. Sensor outputs 350 include output from sensors 1 . . . n (e.g., outputs 307 and 335 in FIG. 3A). These outputs form the inputs (v_input 1 . . . n) 353 to the logic unit 355 (e.g., a microprocessor), RAM 358, battery/power supply 362 and other components including a bus and I/O ports such as for USB port 360 for wired connection via USB cable 367. The USB link may be used for power and/or data transfer. The device preferably includes a wireless communication module 365, for example, BLUETOOTH® or WiFi, for wireless transmission. Data and control signals are sent to another Central processing unit (CPU) 375 which may comprise fast processors, parallel processors including graphical processing units (GPU) 378 that can be used to perform more demanding computations.

Computations by the device may comprise reading, compressing or storing voltage output from the sensors, filtering signals or more advanced computations to create the personal digital phenotype or processing signals based on the PDP. The device can then transmit raw or processed signals, or control signals (e.g., logical decisions based on the sensed signals) to another device using a USB or wireless method (Bluetooth or WIFI). An Internet of Things (IoT) 366 may be used to link group(s) of sensors and/or computing devices. Alternately, data can be transferred directly to the secure cloud 370 for cloud storage and cloud computing services (via wired or wireless communication). The cloud engine 370 will be able to run mathematical operations and computations at optimal speeds, and allow communication from any internet connection.

Figure 4:
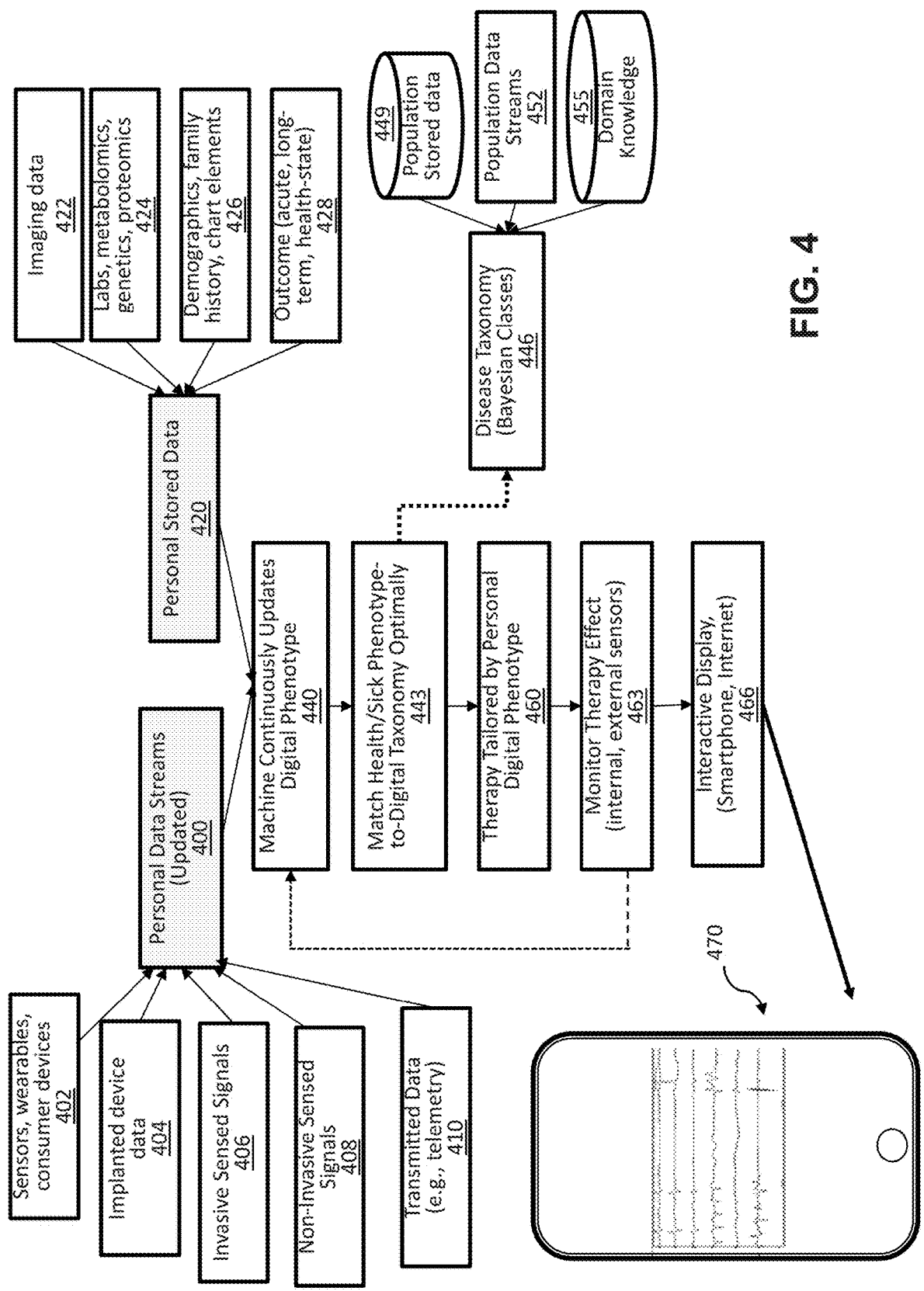
FIG. 4 is a diagram of a sample work flow using the personal digital phenotype and digital taxonomies.

FIG. 4 summarizes work flows for use of the personal digital phenotype to guide personalized therapy and monitor the effects of therapy. Two forms of personal input are taken, data streams 400, which can be updated over time, and personal stored data 420. Data streams 400 may include sensed data from novel or existing sensors 402, such as from wearable devices or consumer products, implanted devices 404, invasive sensed signals 406 from existing or dedicated devices including minimally invasive products such as a skin, nasal, corneal, buccal, anal or auditory probe, from non-invasive sensors 408, which may provide data including motion, and temperature from infrared probes, and from transmitted data 410, such as telemetry from existing medical equipment.

Stored data 420 may include static data such as imaging data 422, ideally including detailed coordinates of regions of scar, fibrosis, ischemia, reduced contractile function and potential border zone tissue, laboratory values 424 including biochemistry levels but also including genetic, proteomic, and metabolomics data (when available); demographic data 426 and elements from the patient history such as presence of diabetes mellitus or hypertension, left atrial size from echocardiography; Outcome data 428, which can include subjective symptoms of whether a patient feels well or not, e.g., "healthy" or "less healthy". Outcome data 428 also ideally includes objective evidence such as acute endpoints of a therapy such as resolution of fever by an antibiotic or, in a preferred embodiment, termination of atrial fibrillation by ablation. Objective evidence may also include chronic endpoints such as absence of infection or lack of atrial fibrillation recurrence on long-term follow-up. As described below, the inventive approach uses combinations of population data including population stored data 449, population data streams 452, and domain knowledge 455 to define disease taxonomy 446 to identify health and illness, to partition data classes based on health-state, and to compare population classes with the individual.

Step 440 shows continuous updating by the machine of personal digital phenotypes. This can be done periodically at pre-determined timepoints or continuously. Step 443 performs a comparison of the personal digital phenotype to the externally determined digital disease taxonomy 446, generated from one or more of population stored data 449, population data streams 452, and domain knowledge 455. These steps are detailed further in FIG. 5.

In step 460, the therapy is tailored to the personal digital phenotype, and in step 463 the effect of therapy is monitored iteratively using data streams in the context of already stored data back in step 440. Finally, an interactive interface to report data is provided in step 466. Display 470 provides one example of the many types of data that can be displayed via an application on a computer or mobile device. (In the illustrated example, a smart phone is shown.) An implementation of the application ("app") has been created for an APPLE® iPhone® written in Swift via Xcode. In the illustrated display screens, sample maps of complex arrhythmia with targets for ablation, a 3-D image of the heart, numerical coordinates, text descriptions, and quantitative scores are shown. The inventive approach creates personal phenotypes from personal data and population data which are able to provide management and treatment decisions, without guidance by expert rules.

According to the invention, phenotypes are based on the ground truth of whether a patient is ill or not, how ill they are, and how best to treat them to maintain health or treat illness. These clinically and biologically relevant operations are included at steps 428, 446-455. The invention acquires novel data in steps 402-410 to create personalized phenotypes, using data types that may not always correspond to data types in stored data in that individual (420-428) or in a comparator population 446-455. Such data types are actively acquired by the system so that personal phenotypes may better guide therapy, and include data types including electrical information or heart structure.

Figure 5:
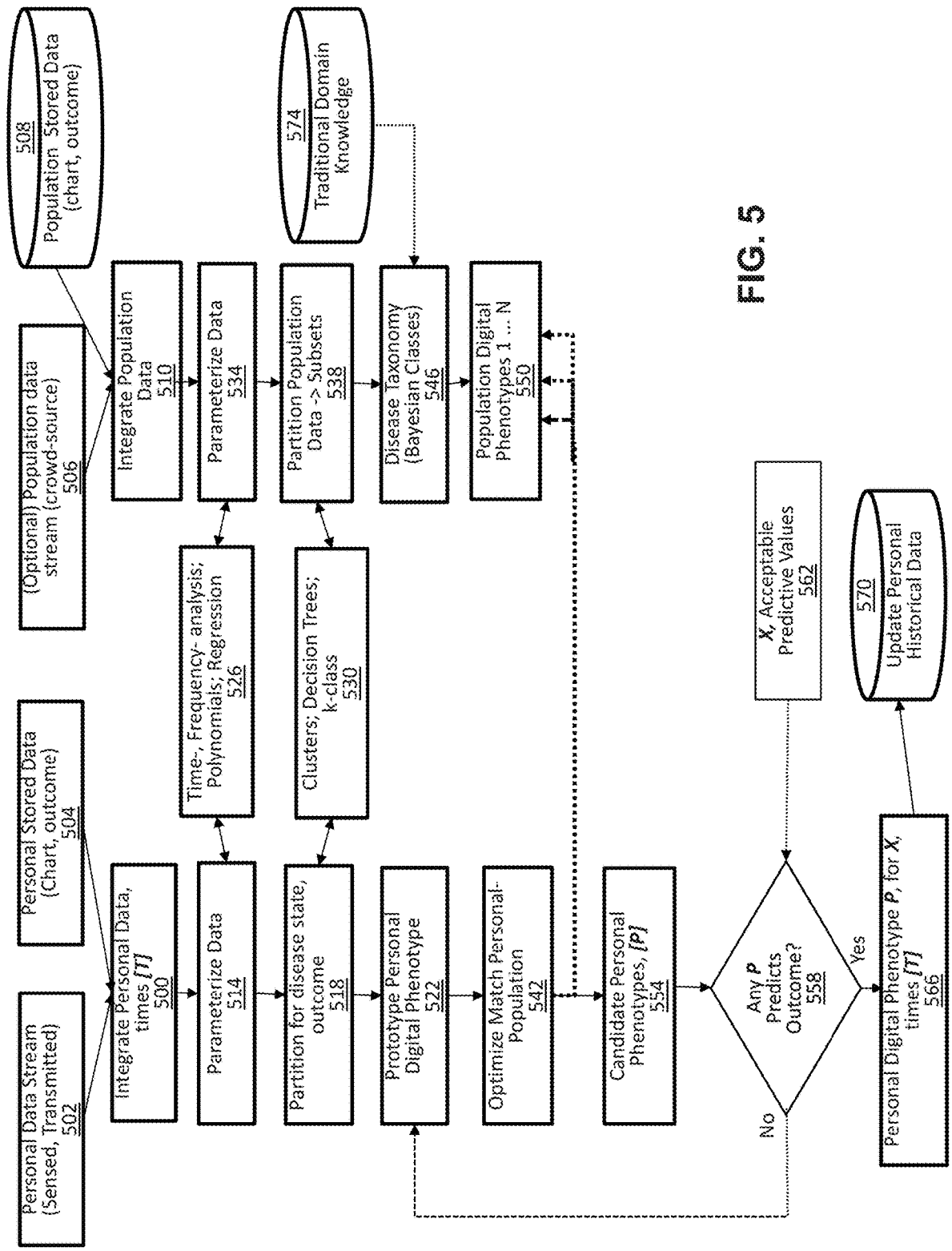
FIG. 5 is a flow diagram illustrating an exemplary process for creating personal digital phenotypes (PDPs).

FIG. 5 is a detailed flow description for creating PDPs. Step 500 takes personal data at time vectors [T] comprising one or more timepoints. This includes data streams 502 (corresponding to step 400 in FIG. 4) and personal stored data from a chart 504 similar to personal stored data 420 in FIG. 4, which includes measures of biological or clinical significance such as acute or chronic outcomes.

Population data streams 506 (block 452 in FIG. 4) are increasingly available. Such data streams may include data from persons with the same—or different—sensed data to the index individual. To provide a few examples, this data may include telemetry data from patients in an ICU ward, individuals using a similar wearable device, or soldiers in the field being monitored for various vital signs.

Data from population stored database 508 (database 449 in FIG. 4) are incorporated using statistical associations that tend to be weak. For example, AF is significantly associated with obesity when assessing populations statistically, but there are also thin individuals who develop AF and many obese individuals who do not. Similarly, there is an association between atrial scar density or atrial scar burden and AF, but many individuals with AF have minimal scar while some without AF have considerable scar. Nevertheless, actuarial associations are obtained from the literature, and mathematical weighting used to adjust for individual demographics using multivariate estimations.

Population data from database 508 are integrated in step 510 (similar to step 446 in FIG. 4), including indices of biological or clinical significance such as acute or chronic outcomes which serve as a reference for diagnostic or treatment utility. The first step is to featurize the data in step 514. This step is designed as a feature (variable) reduction step in general, and to address the curse of dimensionality in machine learning. Feature reduction and feature extraction techniques are well known in the art. Possible operations that may be used for this feature reduction step 526 include time domain analyses such as averaging, integration, area analysis, correlations, principal component analyses. Frequency domain analyses include Fourier analyses, wavelet transforms, time-frequency analyses. Frequency analysis can be performed using a selected parameter associated with the plurality of coordinate pairs (or loops) to generate a frequency spectrum. The selected parameter can be amplitude (e.g., voltage), angle, vector, area and derivative. In some embodiments, the peak can include a fundamental frequency; in other embodiments, the peak can include the fundamental frequency and one or more harmonics of the fundamental frequency. In other embodiments, the peak can include only one or more of harmonics of the fundamental frequency. Polynomial fitting can also summarize datasets as the polynomial coefficients. Other generic featurization steps can be used, using widely available libraries such as TSFresh (Time Series FeatuRe Extraction). In parallel, population data are parameterized in step 534 using similar or different operations.

Step 518 partitions data into classes that represent a digital 'disease phenotype' in an individual, or a digital 'disease taxonomy' in a population. The goal is to better segregate data—clinical data, but also granular invasive data points and lab tests—to into partitions of individuals who may appear similar but have different outcomes from a given therapy (successful versus unsuccessful). Mathematically, this is done by constructing 'hyperplanes' in k-parameter space that separate patients who have one outcome from those who do not. For the preferred embodiment of arrhythmias, for instance, it remains unclear why 'paroxysmal' AF in two patients with similar profiles may response completely differently to medications or pulmonary vein ablation. Personal phenotypes code observations from multiple patients to crowd-sourced partitions ('digital taxonomy') of why AF in some patients but not others reflects sources/driver regions, structural abnormalities, neural components and metabolic comorbidities including obesity. These factors are not predicted by the traditional taxonomy of 'paroxysmal' or 'persistent' AF. Using personal digital phenotypes, inferential methods including statistics and machine learning are used to compare data to reference populations to infer best management.

Step 530 partitions the data as a classification approach. Partitioning can be performed by many techniques known in the art including, but not limited to, cluster analysis and other types of unsupervised learning, or supervised learning methods including support vector machines (SVM), logistic regression, naïve Bayes, decision trees, or other approaches. This partitioning is done for personal data (step 518) and in parallel population data (step 538). It should be noted that the partitioning techniques used may differ for each step.

Cluster analysis, a known unsupervised learning technique, may be used in step 530 to group unlabeled data (e.g., data streams from multiple sensors, input data, other) into a collection of items that are "similar" to one cluster but dissimilar from others. This can occur even without obvious natural groupings, which is often true in these applications since typical phenotypes rarely include clinical data, imaging and continuous data streams. Clustering is a powerful tool in this invention, but since the final duster pattern depends on the initial cluster, any ambiguity in identifying the initial cluster patterns could lead to bias. The result of the clustering is validated later in step 558.

Step 546 creates a disease taxonomy from population data using mathematical models to integrate data streams and stored data from the population (database 508), data reduction schemes (step 534) and data partitions (step 538). Data from domain knowledge database 574 is incorporated to filter mathematical relationships. For example, mathematical weighting may be minimized for breast cancer in men, which is rare, or for AF in young children, which is rare, while raising mathematical weighting for aging in men with coronary disease, which are common. Such traditional domain knowledge is available from epidemiological data and population statistics, may also be available from stored population data, and is easily translated to mathematical weightings.

Step 550 creates population digital phenotypes from the disease taxonomy. In other words, the population digital phenotypes correspond to partitions of data that form self-consistent disease classes from quantitative data. These may be clinically obvious, or clinically obscure—for instance, the link between low magnesium levels and atrial fibrillation in some studies. These partitions are each expressed statistically with confidence intervals, and will be used for comparisons against personal digital phenotypes.

Step 522 creates a prototype personal digital phenotypes using personal disease partitions from step 518 as a base. Step 542 compares the personal digital phenotype (PDP) to find a best match population digital phenotype. Candidate personal phenotypes are given by the matrix of vectors [P] in step 554. This comprises multiple data elements, data types, some ordinal, some vectorial, and some time dependent.

In a preferred embodiment, supervised learning is used to refine digital phenotypes to predict defined outcomes. This involves feature selection, choice of network architecture and appropriate data for training and testing.

Features will be identified and "tuned" for machine learning to avoid overfitting (i.e., poor generalization to future unseen inputs) by deliberately creating sparse input "vectors." The invention eliminates redundant features and maximize diversity of input features to comprehensively span the underlying input data.

In one embodiment, features are grouped into three types: (a) traditional clinical variables (demographics, comorbidities, biomarkers); (b) electrical signals (12-lead ECG and intracardiac signals, of which signal processed parameters can separate AF phenotypes; and (c) imaging data including but not limited to 2-D echocardiogram images (atrial geometry), 3-D CT data (geometry), 3-D MRI data (fibrotic areas, geometry), and 3-D electroanatomic shells of voltage and complex electrogram distribution generated at EP study. Clusters (unsupervised learning) will help for data reduction and be used as additional input features. To understand the significance of features, filtering and regularization are used. The invention eliminates variables not associated with response classes in training. One approach uses the least absolute shrinkage and selection operator (LASSO) that combines advantages of filter and wrapper methods to minimize prediction errors and includes variables that contribute to regression analyses in the final model.

Missing data in each feature group will be treated by inserting (inputting) the: a) median value; b) predicted value using multiple imputation (a technique from statistics); c) expected value of that data-type from the literature; and d) constant signifying missing data. Each approach will be compared during training of various network models.

Formatting of input images and signals. The invention will format each 3-D MRI, CT or pseudocolored atrial electroanatomic image (denoting anatomy, distribution of specific types of electrogram, e.g., voltage) as 3-D matrices. Time-series data (12-lead ECG, bipolar coronary sinus electrograms, unipolar intracardiac electrograms) will be processed prior to entering the final network, using feature extraction, cluster analysis and pre-processing networks.

The outcomes used to train the phenotype will vary with each application. For the preferred embodiment of heart rhythm disorders, several outcomes may be used to train phenotype. One outcome may be high voltage versus low voltage (such as <0.1 mV) electrogram signals; phenotypes associated with high voltage signals may have higher treatment outcomes. Another potential outcome is the presence of clean spatial maps of AF, showing consistent rotor or focal sources/drivers; these sites may be effective treatment targets. Another desirable outcome is AF termination by drug therapy or ablation, or long-term success from drug therapy or ablation. Both can be determined retrospectively in the reference population to form the digital taxonomy, and then used to identify personal phenotypes that match.

In one embodiment, supervised learning, typically implemented as an artificial neural network ("ANN"), is used to represent the diverse input data and data streams for the individual person and population. ANNs typically comprise three elements. First, a connection pattern between different layers of nodes (artificial neurons), forming networks of variable number of layers each containing multiple nodes per layer. Implementations can be as simple as the perceptron, adaptive linear networks, or many other designs including deep learning networks. The actual network design can be adaptive to the specific task and complexity of the data partitions Second, connection weights between nodes can be varied and updated according to multiple learning rules. Third, the activation function: determining how each weighted input is converted to its outputs. Typically, the activation function $f(x)$ is a composite of other functions $g(x)$, which can, in turn, be expressed as a composite of other functions. A non-linear weighted sum may be used, i.e., $f(x)=K(\Sigma_i w_i g_i(x))$, where K (the activation function) may be sigmoidal, hyperbolic or other function.

A variety of connection patterns, weight and mathematical activation functions can be selected, and a variety of updating functions are possible for any embodiment. Specific forms are optimal for different disease states and tasks. For example, the machine for detecting abnormal heart rate during known atrial fibrillation would be less complex than the machine for identifying the site for ablation in atrial fibrillation, for predicting the onset of atrial fibrillation, for predicting an exacerbation of heart failure or for predicting the onset of coronary ischemia.

Alternative forms of learning include supervised and unsupervised methods including linear logistic regression, support vector machines, decision trees in "if-then-else" statements, random forests and k-nearest neighbor analyses. Such formulations can be applied independently, or as part of machine learning to augment or create boundaries between desired decisions such as the presence or absence of sources for atrial fibrillation or other associations linking input data with clinical or physiological outcome for an individual. Several other forms of machine learning can be applied, and will be apparent to an individual skilled in the art.

Various connection patterns, weighting, node activation function and updating schemes can be selected, and specific forms are optimal for different applications depending on the data inputs. For instance, imaging inputs and continuous data series (e.g., electrogram signals) may be represented by different networks, optimized in the preferred embodiment with substantial training data, to each dataset in a given reference population. Thus, depending on the application, the invention can be tailored to best represent EEG data, cardiac and respiratory signatures, weight, skin impedance, respiratory rate and cardiac output. Recurrent neural networks are a data structure which enable analysis of how the network achieves its trained conclusions. Manually engineered scalar features (e.g., clinical data elements) can be incorporated using fully connected layers. Featurized time series (i.e., 12-lead ECGs or so-called 'electrograms' from inside the heart) are processed via convolutional neural networks. Standard techniques of dropout, batch normalization, and hyperparameter tuning are used to avoid overfitting.

An important feature of machine learning approaches is that they do not need a priori knowledge of the specifics of human pathophysiology, but instead learn patterns of sensed signals and input data in health and deviations in disease. Thus, they are well suited to enhance current disease classifications based on current mechanistic hypotheses that may be suboptimal.

Step 558 determines which candidate phenotype(s) can be validated, i.e., which predicts any hard outcome measure. For AF, this may be sites where ablation terminated AF. For coronary disease, this may be clinical constellations that predict critical stenosis of epicardial coronary vessels, i.e., an advanced coronary risk score. By extension, such candidates can be defined for non-heart diseases. If a match is not achieved, then the process is repeated 522 or the acceptable tolerances X (block 562) are widened. If a match is achieved within acceptable tolerances (vector X), the candidate becomes the Personal Digital Phenotype P within tolerances X at times T in step 566. The phenotype is then used to update the personal historical data for that individual in database 570, against labeled outcomes used to validate the phenotype. This step is used to validate clusters defined in preceding steps as well as for supervised training.

Figure 6:
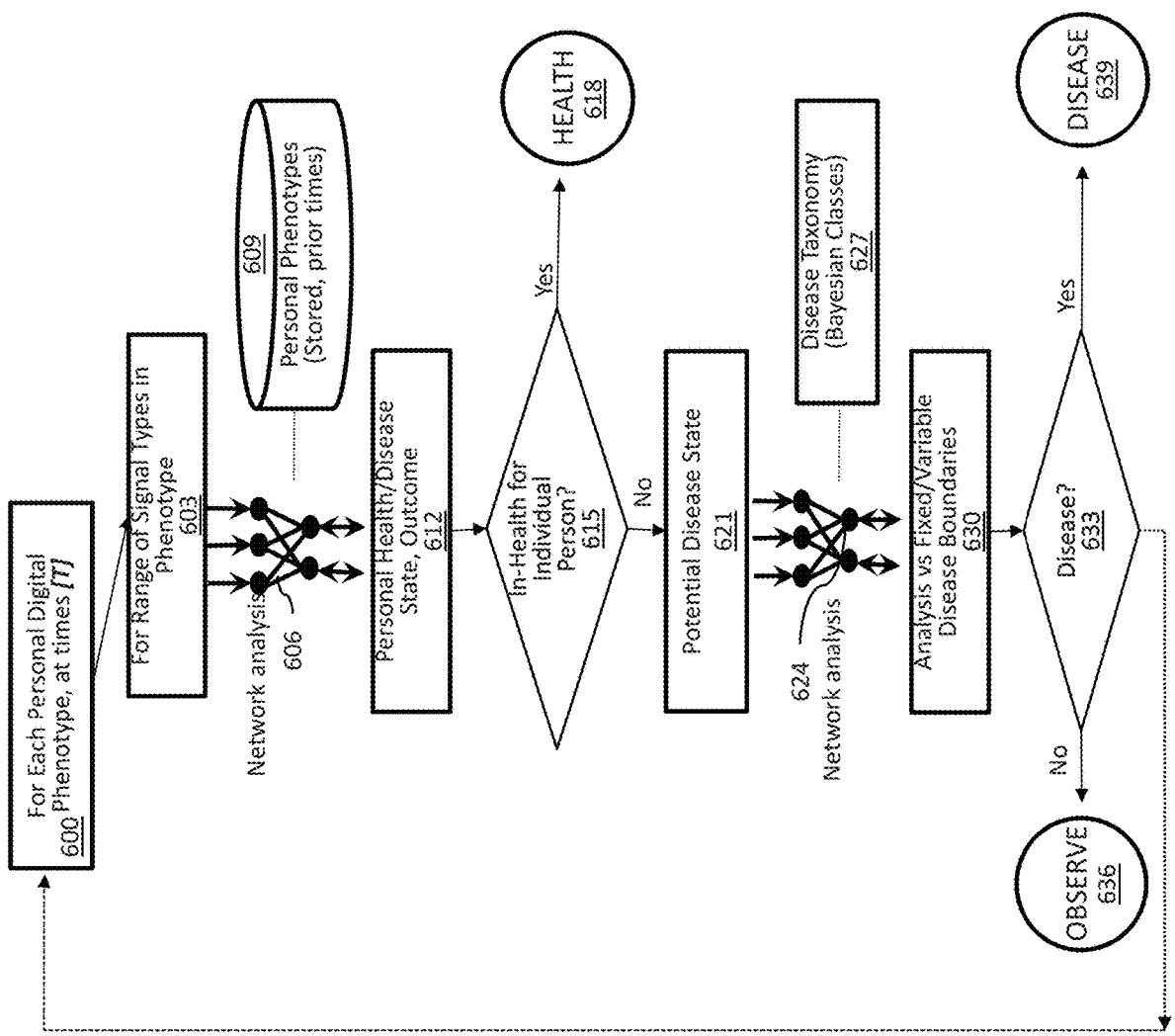
FIG. 6 is a flow diagram showing how personal phenotypes and the digital taxonomies can be used to define health, disease or justify continuing surveillance.

FIG. 6 defines health and disease using the personal digital phenotypes. Step 600 takes each personal digital phenotype at various times T in step 600, and for each examines the signal types in the phenotype 603. Mathematical and network analysis 606 are used to identify abnormalities, compared first to stored personal phenotypes in database 609 (i.e., data from prior times adjudicated to outcomes, including when the individual was feeling well or unwell (symptoms), or had objective evidence for disease presence e.g., an AF episode or not, or disease worsening (e.g., progression from paroxysmal to persistent AF). Step 612 generates a portrait of personal health or disease based on this analysis.

Step 615 now determines if this represents health 618 or not, for the individual, within accepted tolerances. If this is "out-of-range" for healthfulness in that individual, then the individual may have entered a potential disease state 621.

Mathematical and network analysis 624 is performed, compared to population disease taxonomy 627 to determine if the abnormality for the individual falls into "out-of-healthful range" for the population as well. On comparison against population fixed and variable definitions of abnormal, defined statistically (step 630), the invention now asks if disease is present in step 633. If "yes," then disease 639 is declared; If not, in observe step 636, the patient continues under careful surveillance. In either case, the process repeats for continued monitoring.

Figure 7:
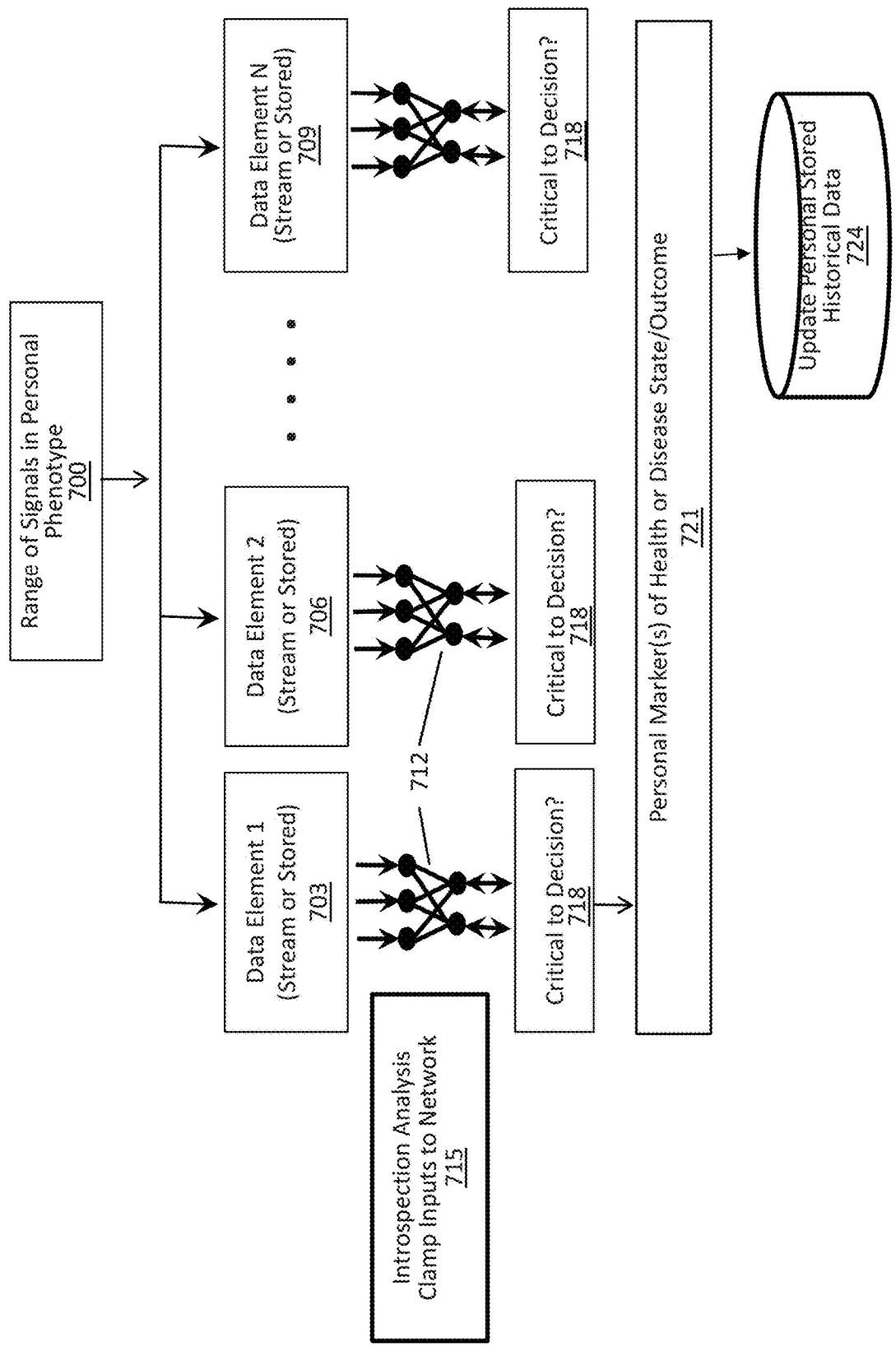
FIG. 7 summarizes a process flow for identifying specific deranged elements of the personal digital phenotype.

FIG. 7 outlines novel interpretability analysis of supervised networks, i.e., identifying which signal type and input type at which point in time contribute most to the abnormal personal digital phenotype. Interpretability is a major novel feature of the inventive approach, addressing a major traditional criticism that machine learning is a "black box". Expert knowledge can be used to featurize massive data (i.e., enhance by adding important data without overwhelming the network with "dimensionality"). We also use domain knowledge for secondary manual interpretation. Step 700 analyzes all signals that are part of the personal phenotype in turn. Data elements 703, 706 . . . 709 consider each data element in turn (whether input data or data streams). Several approaches are used in step 715 to explain the classification by the neural network 712, i.e., which component(s) caused the 'disease' versus 'health' classification.

Several interpretation techniques can be used, and will be familiar to one skilled in the art. The first approach includes the use of attention layers in recurrent neural networks. Alternatively, the invention can use Local Interpretable Model-agnostic Explanations (LIME), to explain predictions by approximating an interpretable model. LIME can be used for 1-dimensional data such as the ECG or electrical signals from within the heart (electrograms), numeric features or images. A third approach is Gradient-weighted Class Activation Mapping (Grad-CAM), which identifies the most critical nodes as the largest weight multiplied by backpropagated pooled gradient downstream to the final convolutional layer. Another embodiment specifies features that should or should not be part of the model including spatial domains in images (e.g., size of an atrial driver region, or ventricular conduction velocity, or spatial extent of fibrosis in the human heart) enabling tailored interpretation to domain electrophysiological "concepts" to ensure that models do not converge on irrelevant concepts. An example of this is the Testing with Concept Activation Vectors (TCAV) approach. This can examine specific features that should or should not be part of the model (e.g., size of AF driver regions), enabling the inventive technique to tailor interpretability to accepted "concepts". As another example, prediction of an AF outcome (e.g., success or failure of ablation) can be tested by an interpretable model, e.g., presence of fibrosis near the right atrium. This approach attempts to ensure that numerical models are relevant to predictions, and models do not converge on irrelevant concepts. Explainable features predicting outcome will thus be identified quantitatively. Clinical rationale can subsequently be added 574 via domain knowledge, e.g., the determination that obesity predicts negative outcome from ablation or drug therapy, while hair color predicting positive outcome may not. Data on populations in whom class IC anti-arrhythmic drug (AAD) may be used can also be included.

A key feature of the digital taxonomy is to code discordant cases, i.e., where the neural network fails to predict actual outcome. For instance, in a patient with failed ablation therapy whose profile includes atrial scar on MRI, the invention will be trained to link the locations of scar, with locations of ablation lesions, with outcome. One potential output from the trained network may be that ablation that misses regions of scar may produce poor outcome. Domain knowledge (physiological interpretation) is used to provide plausibility for any trained network, to ensure mathematically that implausible (or impossible) links are not constructed, and hence revise the network. This combined mechanistic/machine learning approach is a novel strength of the invention that is often omitted from machine learning systems that do not check data representations against known domain knowledge. Famous errors in existing networks include adversarial examples; in image recognition, applications in which changing one pixel can alter the classification from 'cat' to 'dog'. The present invention prevents such trained networks from being developed in this medical space where errors must be minimized.

Accordingly, the invention is focused on developing, testing and revising increasingly interpretable data structures. Models will combine statistical analyses with expert interpretation of case failures/successes. Simple statistical tests and linear models may help to identify correlations between different variables in a system, but may not be able to capture underlying complexity and nonlinearity of these studied complex clinical problems. Decision trees (CART) may allow greater interpretability of the importance of each extracted feature from layers of the network. Inputs to decision trees will be extracted features from the images and time series signals.

Another approach in this invention is termed "network clamping." In step 715, from a trained baseline "health" version of the network, inputs are deranged singly or in batches and the network 712 is rerun to identify which abnormal input combination causes the network to most closely recapitulate the "disease state."

These steps are evaluated in steps 718 to identify the constellation of inputs that characterize the state of health, disease and outcome in step 721. This result is then used to update the personal historical data in database 724.

Figure 8:
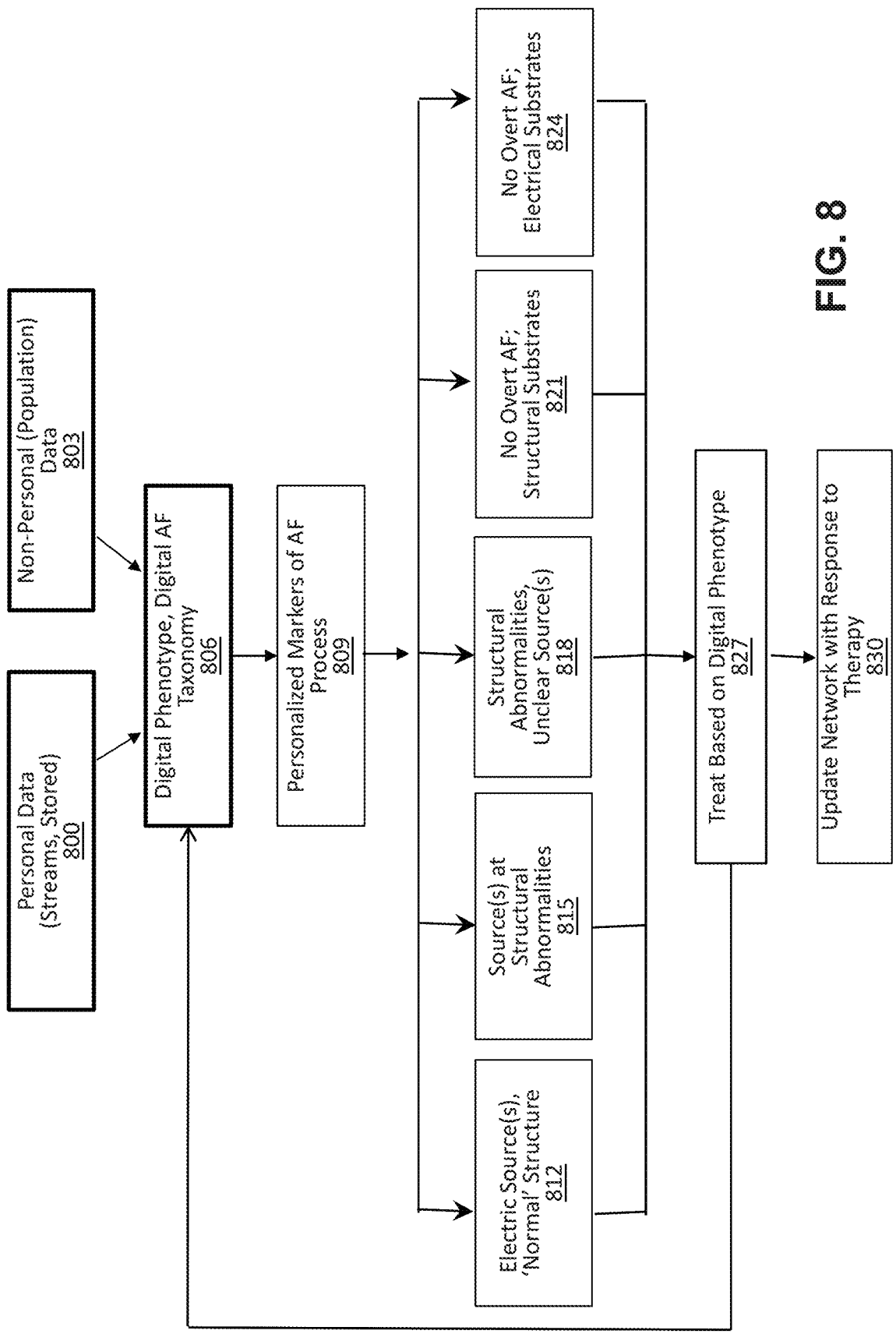
FIG. 8 illustrates an exemplary treatment sequence based on PDPs for atrial fibrillation.

FIG. 8 provides examples on treating AF using abnormal personal digital phenotypes. Step 800 comprises personal data and step 803 comprises population data as described before. Step 806 finds the best match between the personal AF phenotype and the digital taxonomy. Step 809 uses the critical element analysis from FIG. 7 (steps 718) to identify markers of the AF process in that individual. Steps 812-824 identify different features of AF that may be identified by mapping. These steps are further elaborated with reference to FIGS. 9-11. Step 830 updated the personal historical data in the database 724.

Step 812 identifies patient phenotypes who manifest the electrical pattern of complete rotations (rotors) or focal sources, without structural abnormalities. Treatment 827 in this case may include ablation to the driving source.

Step 815 identifies patient phenotypes who manifest electrical complete rotations (rotors) or focal sources, associated near structural abnormalities marked by low voltage or potentially by abnormalities on delayed enhanced magnetic resonance imaging. Treatment 827 in this case may include ablation to the driving source(s) with extension of ablation to regions of nonconducting scar or fibrosis.

Step 818 identifies patient phenotypes with manifest structural abnormalities marked by low voltage or potential abnormalities on delayed enhanced magnetic resonance imaging, but may not show classical electrical rotations (rotors) or focal sources. In this case, the representative networks will find other electrical patterns such as partial rotations or repetitive activations in patients which are targets for therapy. Such atypical patterns may be useful in patients with specific comorbidities, e.g. consistent with advanced disease. Treatment 827 in this case may include ablation at these atypical electrical source(s) with extension of lesions to regions of nonconducting scar or fibrosis.

Step 821 provides an option for disease prediction. In this step, the inventive technique identifies patient phenotypes who do not manifest AF but who may be at risk due to specific patterns of structural abnormality marked by low voltage or potentially abnormal on delayed enhanced magnetic resonance imaging. In this case, the invention provides for AF prediction. Ideal input data in this case may comprise granular imaging data showing MRI abnormalities, or granular data on regions of low voltage to enable non-invasive detection of structural risk profiles by the network to provide prognosis, or potentially targets for therapy. Treatment 827 may include ablation to connect these regions of scar or fibrosis.

Step 824 is another option for prediction. The invention identifies patient phenotypes who do not manifest AF but who may be at risk due to specific electrical patterns marked by altering electrical propagation at changing rate, indicating rate-dependent block, or oscillations in conduction to specific areas suggesting alternans of refractoriness or conduction. Ideal input data in this case may comprise body surface potential signals to enable non-invasive detection of electrical risk profiles by the network. Treatment 827 in this case may include ablation to eliminate these regions of electrical vulnerability.

Figure 9:
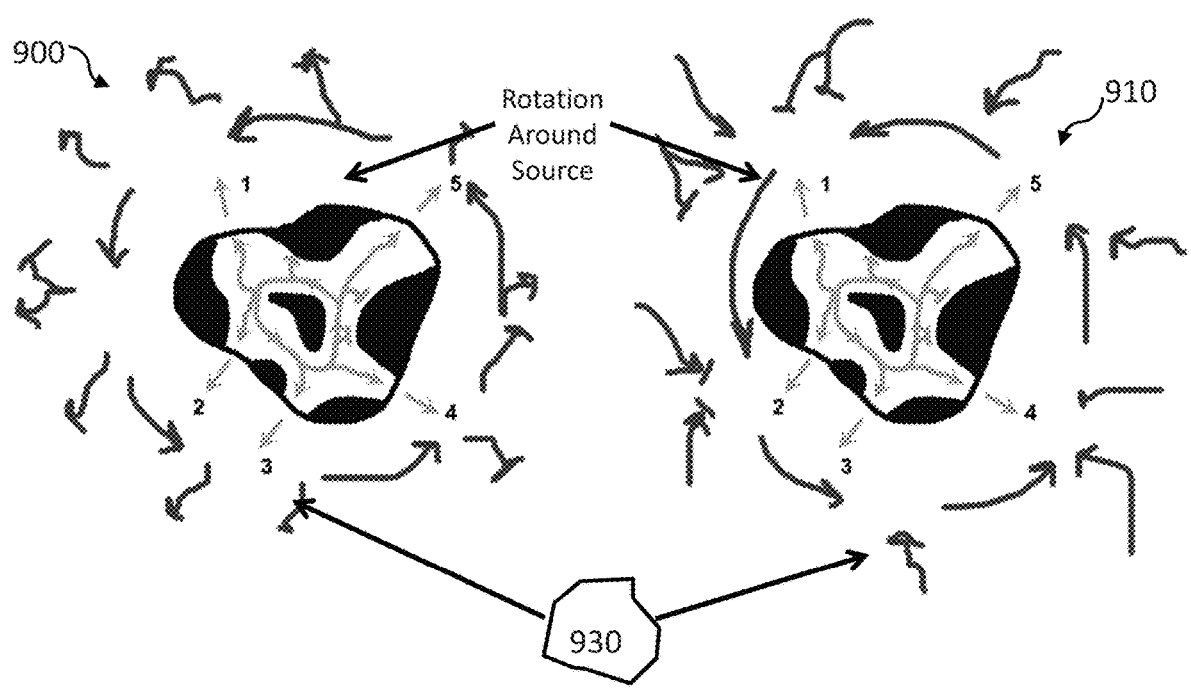
FIG. 9 shows sample phenotypes of complex arrhythmias, including (A) Fibrillatory conduction away from a source/driver, (B) Disorganized activity that does not perturb the source/driver; (C) Arrhythmia based on structural abnormalities.

FIG. 9 illustrates examples of complex arrhythmias, describing how sample personalized phenotypes can be used to tailor therapy to each of heart rhythm disorder. Disorganized activation can have numerous effects on a source. In the left side of the figure, diagram 900 shows disorganized activation emanating from the source. This behavior is often termed "fibrillatory conduction" from the rotor, focal source or other driving mechanism. In this case, the invention may use one of several mapping systems (including those that freely available) to determine that patterns of mostly rotational or focal activation drive AF (i.e., within the core indicated by the sequence 1,2,3,4,5. Alternatively, in diagram 910 on the right, disorganized activation may surround the source ("outside disorganization") yet be directed inwardly, such as from a second source. If this outside disorganization does not perturb the driver, the invention is able to show that rotational or focal activation (again, sequence 1,2,3,4,5) may continue to drive AF even if periodically interrupted by said surrounding disorder (as shown by human optical mapping by Lin, Fedorov et al. *Circulation* 2016, and clinically by Kowalewski et al., *Circulation Arrhythmia/Electrophysiology* 2018). The second source may be a rotor or focal source of a complex rhythm, with disorganization at the interface known as "collision" or "fusion". Third, disorganized activation may be clustered near sites of anatomic abnormality 930 without clear rotational or focal activity. Here, the structural obstacle(s) 930 may maintain the rhythm disturbance. The inventive approach may determine that activation showing specific elements of partial rotational or partial focal activation, structural elements, or their interaction, may be drivers. Further, the inventive scheme may determine that regions of interest that control a greater area of the atrium are fertile areas for therapy. This determination is made for each individual using machine learning and other processing elements involving the personalized digital phenotypes based on detailed cardiac mapping.

Figure 10A:
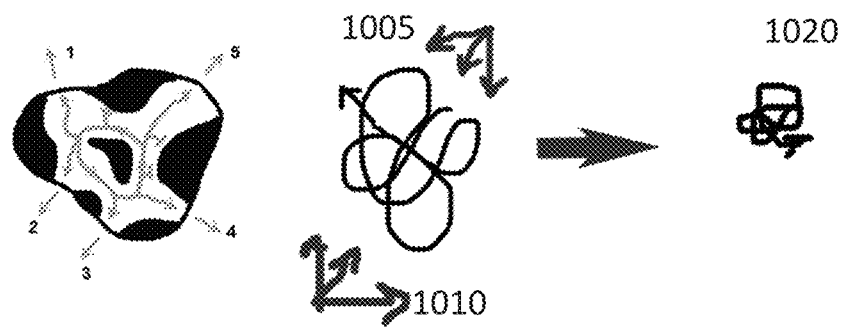
FIGS. 10A-10C illustrate interventions designed based on the personal digital phenotype of arrhythmia, including constraining or perturbing the spatial localization of a source for an arrhythmia or terminating the source for an arrhythmia.
Figure 10B:
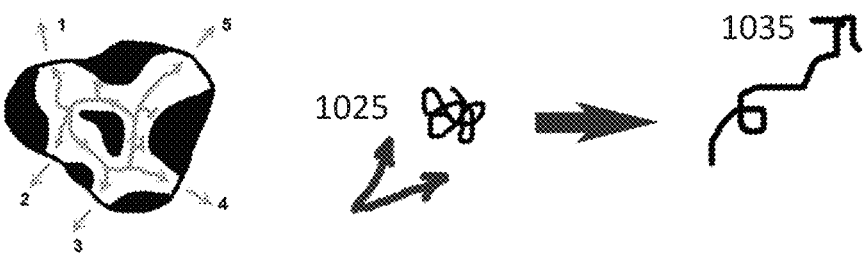
Figure 10C:
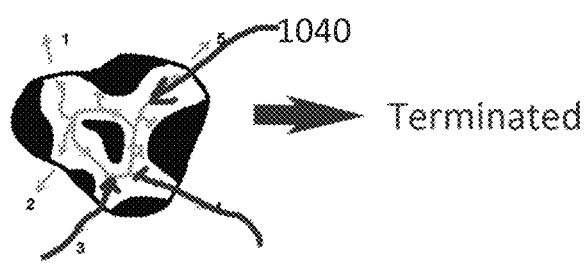

FIGS. 10A-10C are examples of how therapy can be tailored to personalized digital phenotypes for a rhythm disturbance, each illustrating a personalized phenotype that includes an electrical driver. For simplicity, the rhythm disturbance in each case is shown as rotational, but could be focal or another pattern (e.g., repetitive, partially focal or partially rotating). In FIG. 10A, an intervention such as pacing (1005, 1010) can modify the critical driver by limiting its spatial location, blocking at electrical and structural sites to limit motion of fibrillatory cores while it continues to operate. This source may precess in limited spatial areas 1020, thus stabilizing it. Therapy can now be tailored to limit source precession so that it is fixed, converting a complex rhythm disorder into a simple rhythm disorder such as a focal atrial tachycardia that is easier to treat. In FIG. 10B, therapy is tailored to intentionally alter the spatial location of a source, pushing critical drivers to boundaries or regions where they can no longer sustain, e.g., inert regions of the heart, or even outside the heart, thus destabilizing the locus. Pacing 1025 passes regions of functional block (electrical) or anatomic block (structural) that were protecting the critical driver from surrounding colliding waves. The incoming pacing wave causes source migration 1035 to sites where it may be easier to treat, or encounter an obstacle and terminate. In FIG. 10C, pacing 1040 passes regions of functional block (electrical) or anatomic block (structural) that were protecting the critical driver from surrounding waves, and thus invade the source causing it to terminate. This termination may be permanent or transitory.

Figure 11:
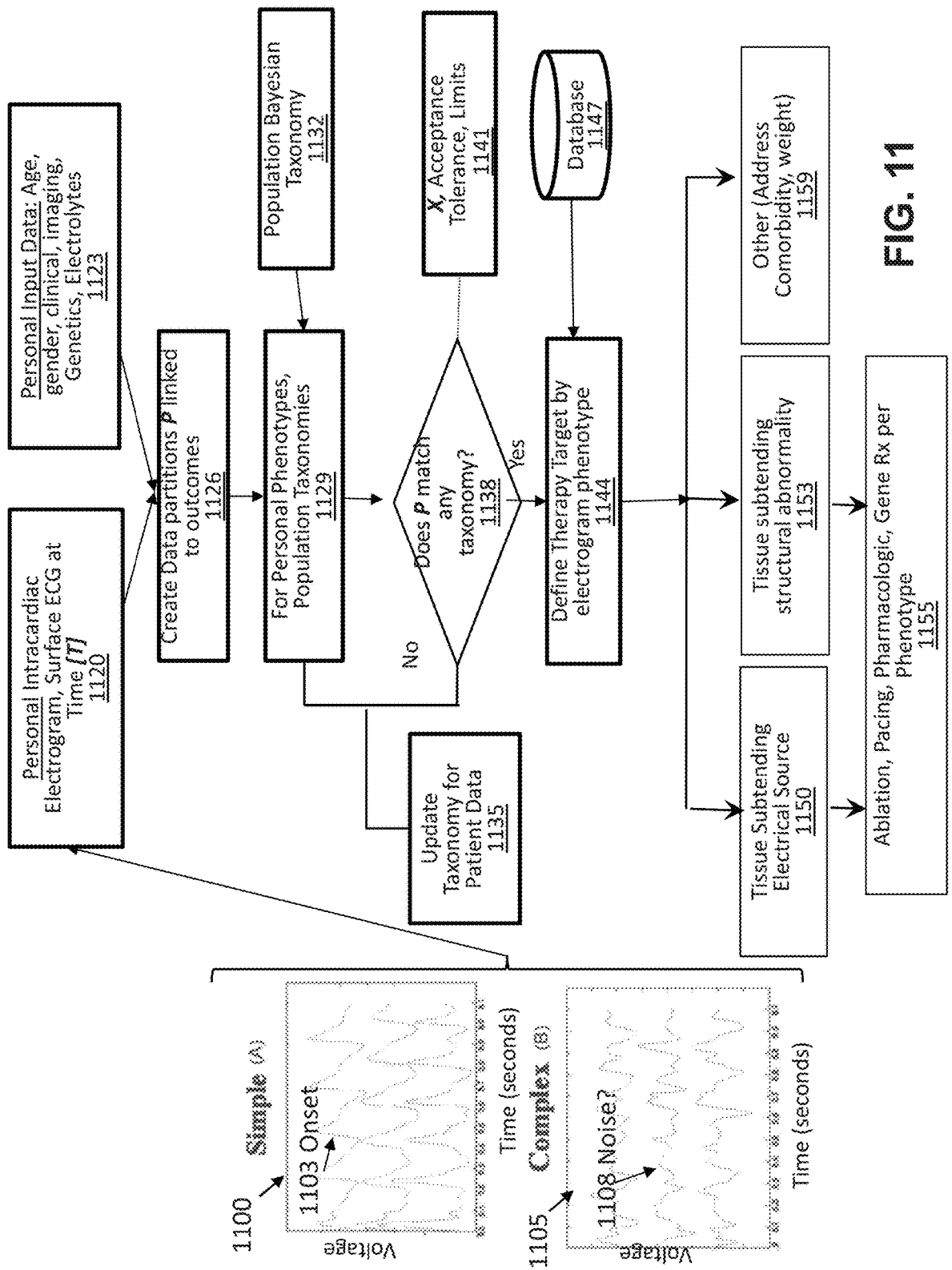
FIG. 11 illustrates a process flow for one embodiment of the inventive method for analysis and treatment of arrhythmias with electrograms (voltage-time signals) as input data.

FIG. 11 illustrates an example operation for arrhythmia. This preferred embodiment analyzes streams of raw voltage-time data from intracardiac electrograms or ECGs, detected by a wearable or implanted device, or during an electro-physiologic study, to guide therapy. Electrograms of a simple arrhythmia 1100 and a complex arrhythmia 1105 are shown. As an example, the heart rhythm disorder can be a complex rhythm disorder AF, VF and polymorphic VT, or another heart rhythm disorder.

In this example, the signals in 1100 and 1105 show deflections 1103 that represent activation onsets (e.g., for heart beats) as well as deflections that represent noise 1108. In AF, multiple colliding waves mean that any one electrode can detect local activity plus activity from other sites or noise. A major challenge is to identify deflections in AF that represent "local" cardiac activation at that site. This information is then used to generate maps of AF which may point to regions of organized rotational or focal activation, which may drive the surrounding disordered activity. However, maps may obscure these features if true activation is detected by different methods. Some signals do not show identifiable activation onsets (e.g., for heart beats) e.g., noise 1108. Such signals include multiple deflections of short duration caused by the heart rhythm disorder that makes the discernment of activation onsets (depolarization) potentially difficult, and with little clear ground truth. Traditional methods use features such as sharp inflection point and high slope of depolarization to indicate true sites of cardiac activation, versus gentle, low-deviation slopes of repolarization typically of duration 100 ms to 250 ms. This is addressed below by the inventive approach, which has been trained using ground-truth of activation times and repolarization times from monophasic action potential recordings.

Real-time data streams with their time stamps form inputs for the system at step 1120. Other non-streaming data for this individual are input in step 1123. Step 1126 creates the initial data partitions or data vectors given by the matrix P, including different data types, values (in this case for electrogram data). Partitions from step 1126 are linked to outcome from personal data or from the population data. Outcomes can be subjective (symptoms), or objective (acute termination by ablation, or chronic long-term freedom from AF). This differs from prior art.

Steps 1129-1147 correspond to the personal phenotype to population phenotypes (i.e., the digital taxonomy). Step 1129 scans all personal phenotypes and all population taxonomies (phenotypes), input from step 1132.

Step 1138 determines of the personal and population digital phenotypes match, within acceptance limits defined by the vector X which is tuned for the application (electrogram analysis) and phenotypes. Matching is performed using steps corresponding to steps 542 in FIG. 5. Several approaches can be employed, but a preferred implementation uses machine learning. If a match occurs, step 1144 defines a therapeutic target from the data referenced to the digital taxonomy and database 1147.

Phenotypes that may be candidates as AF ablation targets include learned mathematical combinations of electrogram features plus clinical comorbidities (e.g., high body mass index, diabetes, hypertension), demographics (e.g., age, gender, prior ablation or not) and, if available, genetic, metabolic and biomarker information.

Applications of this invention use machine learning to improve upon identification of local electrical activation to produce better AF maps, and use personal digital phenotypes to identify features other than rotational or focal activity that may be critical for AF in that person. A specific digital taxonomy for this application comprises electrograms at sites where ablation did and did not terminate AF. These data serve as input-output pairs, to compare maps created by various approaches. Approaches that creating map that explain sites of AF termination, for instance showing a focal or rotational source or low voltage, are weighted higher in competitive machine learning. These electrogram features and the optimal mapping may differ for patients of different atrial size, wall thickness (hence voltage) and extent of scar. This may help to distinguish between local and far-field activation in elements 1103 and 1108.

Potential electrogram targets include low voltage, rotational electrogram patterns (exemplified by pattern 1205 in FIG. 12), focal activation patterns (i.e., sites of consistent centrifugal emanation), partial rotational patterns, partial focal patterns, sites of high dominant frequency, sites of high signal complexity and each of these sites that may control large regions of the atrium in AF (supporting a causal role). Each site, if consistent, may indicate regions critical to the maintenance of rhythm disorder. The invention combines these electrogram features with clinical data into personal electrogram phenotypes.

Personal digital phenotypes may be used to identify novel electrogram targets by analyzing beyond 'traditional' targets. For instance, studies have suggested that targets such as repetitive patterns, or transient rotations or focal patterns, or interrupted rotational or focal patterns, may be critical to maintaining arrhythmia in some individuals. This preferred embodiment of the invention defines these electrogram features, by determining in individual patients which may be related to favorable outcomes. This then becomes a numerical classification within the digital taxonomy as data from more individuals is labeled and accumulated.

Still referring to FIG. 11, steps 1150-1159 provide some therapy options based on personalized electrogram-based phenotype. Therapy option 1150 identifies a tissue region subtending a clear electrical target. Depending on the patient, this may be a rotational or focal source/driver, or other electrical feature—regardless of structure. Option 1153 targets a region of tissue subtending a structural abnormality. Intermediate phenotypes may be present in phenotypes in specific individuals (electrical and structural, which may dynamically change with e.g. changes in health status). Again, multiple forms of electrical pattern may colocalize with this structural element, and the invention will store electrical signals associated with these sites to update the personal and population databases (1147). In both cases, option 1155 provides therapy including destruction of tissue by surgical or minimally invasive ablation, to modulate it via electrical pacing or mechanical pacing, or gene therapy or stem cell therapy, or drug therapy. Medications may include class I agents to decrease atrial conduction velocity, or class III agents to prolong refractoriness. AF ablation may not just eliminate tissue, but target areas bordering fibrosis or areas of electrical vulnerability. Therapy can also be directed to related tissue to these regions, their nerve supply, or other modulating biological systems.

Option 1159 provides other AF therapy options, including lifestyle changes (such as losing weight, controlling ventricular afterload or other factors). This personalized approach may improve outcomes, eliminate repeat interventions by selecting strategies with the highest predicted initial success for a given individual, and hence reduce cost and delays in treatment.

Figure 12A:
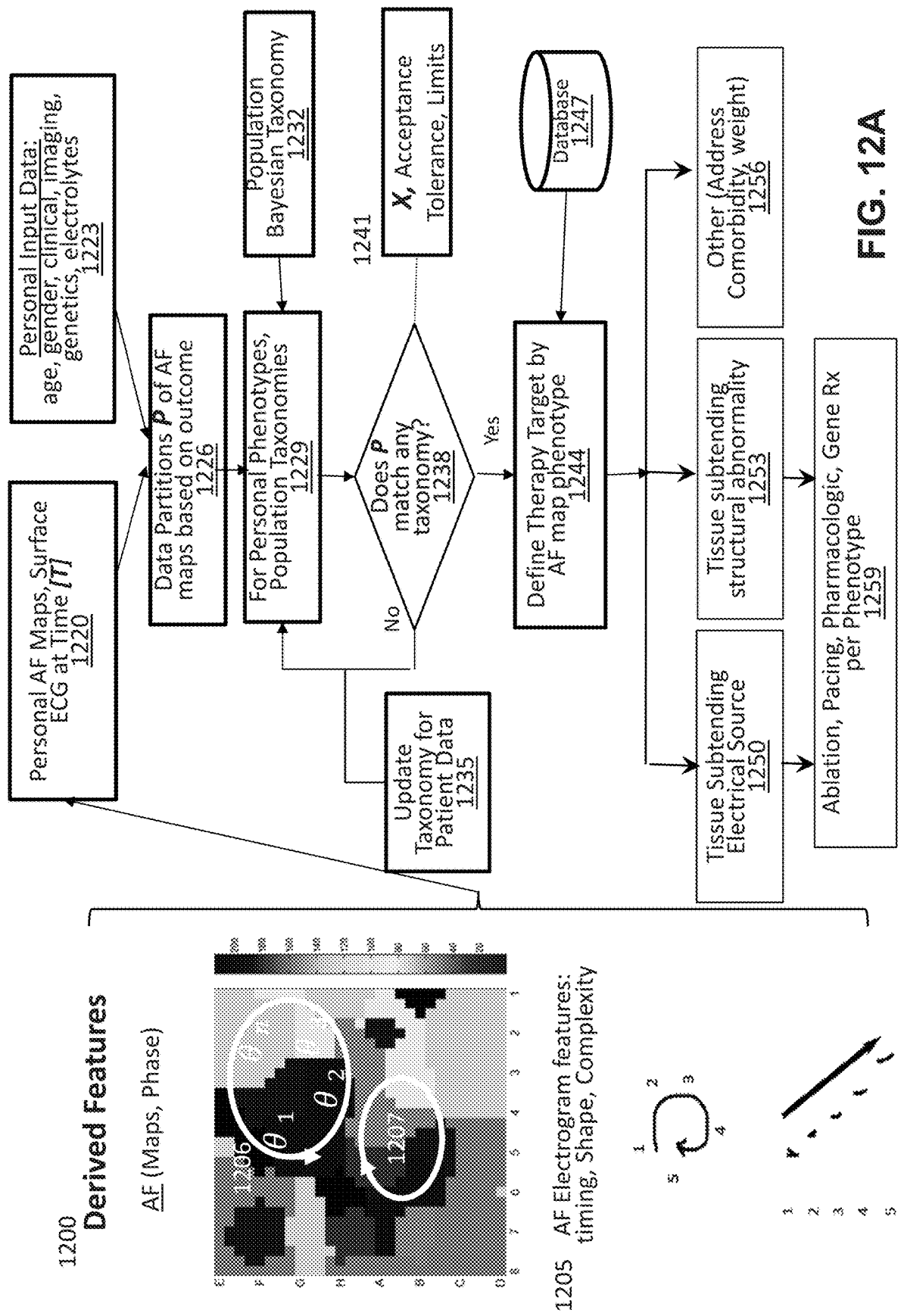
FIG. 12A illustrates a process flow for an embodiment of the inventive method for analysis and treatment of arrhythmias with maps of rotational activation from any mapping method as input data.

FIG. 12A shows another example for the preferred embodiment for arrhythmia, illustrated for maps of AF that are increasingly available from freely-available sources and proprietary systems. AF map 1200 is colored (shaded) and annotated to indicate features in regions 1206 and 1207. Several features may be critical drivers, include timing, shape and complexity. This includes rotational circuits (illustrated) that can be identified using a rotational activation time sequence 1205 for sites 1-5 in a putative circuit, but also using phase angle information denoted θ. Other novel features include machine learned partial rotations, partial focal, and repetitive spatial features. Maps can be generated using software available from commercial vendors, from freely available online mapping tools (Alhusseini, 2017), or other new systems and used as inputs. These maps can be generated by electrophysiological recorders, dedicated mapping equipment, online resources, smartphone apps (for example, see FIG. 14E), and streamed as an input 1220 to the system. As in FIG. 11, personalized input data, e.g., age, gender, clinical, imaging, genetics, can be input in step 1223.

Steps 1226 create data partitions based on AF maps. An advantage of the present invention is the ability to identify one or more sources of a complex rhythm disorder in an individual, using data that extends beyond just heart rhythm. Complex heart rhythm disorders may appear chaotic, but may be due to a small number (1-5) of sources from which activation emanates to cause the complex rhythm disorder. Sources may include rotational circuits (rotors), from which waves, typically spiral waves, emanate to cause disorganized activation. Sources may also include focal impulse regions (focal sources), from which activation emanates centrifugally to cause disorganized activation. The inventive scheme identifies those circuit types along with additional less well-studied targets such as repetitive patterns, or transient rotations or focal patterns, or interrupted rotational or focal patterns, which may have value in some individuals.

A key problem in the prior art is that AF in some patients may be strongly related to rotational sites or focal sites, AF in other individuals may show a less strong relationship, and AF in still other patients may have quite different mechanisms. There are also cases in whom AF is a "final common pathway" of multiple comorbidities or diseases, which may represent some of the different types of AF. Currently, these types of AF cannot be separated. The inventive approach extends the prior art by adding detailed clinical data to electrical data to create a personal digital phenotype, including data on mechanical and other functioning of the heart, structural abnormalities of the heart from imaging such as magnetic resonance, and clinical parameters including age, gender, demographics, family history, comorbidities such as obesity, presence of diabetes, indices of genetic and metabolomic profile. In a patient with extreme obesity, for instance, AF may not be driven by rotational or focal drivers but relies more upon structural factors. The taxonomy will take these clinical factors into account, create phenotypes and individualize therapy accordingly. In another patient with different and/or less advanced clinical factors, AF may be driven from specific regions (focal or rotational), and these sites may lie predominantly near the pulmonary veins.

Step 1229 compares phenotypes centered on AF maps to the population digital (Bayesian) taxonomy 1232. Step 1238 performs a comparison using methods such as machine learning as described in step 542 of FIG. 5 using acceptance tolerance limits defined by the vector X in step 1241. Step 1244 defines the therapy target by this AF phenotype based on comparison against the digital taxonomy and data from the database 1247.

Steps 1250-1259 represent options for therapy based on the personal AF map-focused phenotype. Option 1250 identifies a tissue region subtending a clear electrical target. Depending on the patient, this may be a clear rotational or focal source/driver, or other electrical feature—regardless of structure. Option 1253 targets a region of tissue subtending a structural abnormality. Any form of electrical fingerprint may be present at this structural element, and the invention will store electrical signals associated with these sites to update the personal and population databases 1247. In both cases, therapy option 1259 includes treatments such as destruction of tissue by surgical or minimally invasive ablation, modulation of tissue via electrical pacing or mechanical pacing, gene therapy or stem cell therapy, or drug therapy. Medications may include class I agents to decrease atrial conduction velocity, or class III agents to prolong refractoriness. AF ablation may be used not merely to eliminate tissue, but can also target areas bordering fibrosis or areas of electrical vulnerability. Therapy can also be directed to related tissue to these regions, their nerve supply, or other modulating biological systems.

Therapy option 1256 includes other AF therapy approaches such as lifestyle changes, e.g., losing weight, controlling ventricular afterload, and other factors. This option may be effective particularly in patients with advanced AF, such as patients with no clear AF drivers/sources on AF maps. This option could be achieved by determining maps from body surface ECG information (step 1220) non-invasively. Overall, this personalized approach provides a mechanism for improving outcomes and eliminating/minimizing repeat interventions by selecting strategies with the highest predicted initial success for a given individual, and thus reduce cost and delays in treatment.

At therapy option 1256, the inventive scheme can also be used to integrate anti-inflammatory agents and immune-suppression as novel therapy of arrhythmias for certain digital phenotypes. Anti-inflammatory therapies may include steroidal or non-steroidal agents, immunosuppression using agents used for transplantation, and cell therapy.

Figure 12B:
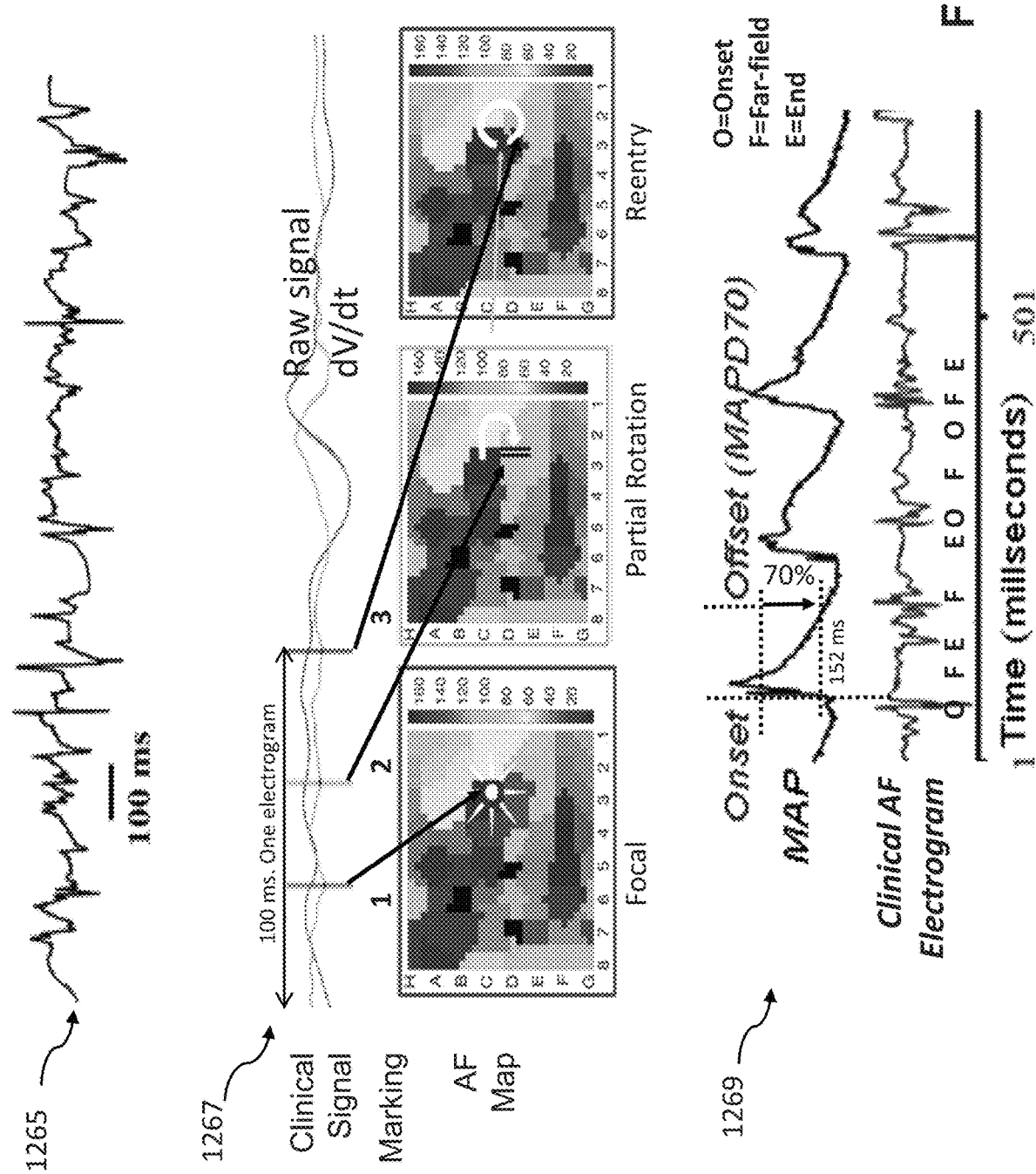
FIGS. 12B-E show details of using the inventive scheme of FIG. 12A to derive maps of arrhythmias for a given patient, where FIG. 12B provides examples of challenges in identifying deflections.
Figure 12C:
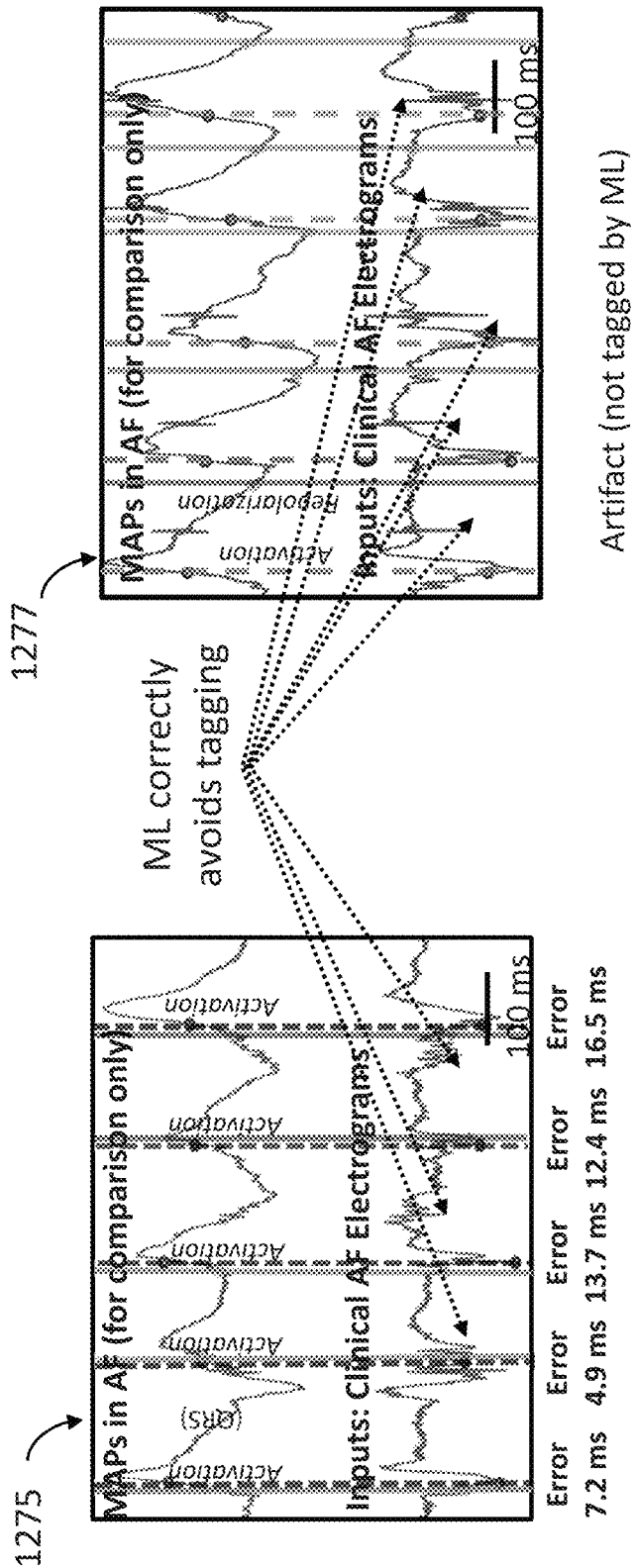
Figure 12C:
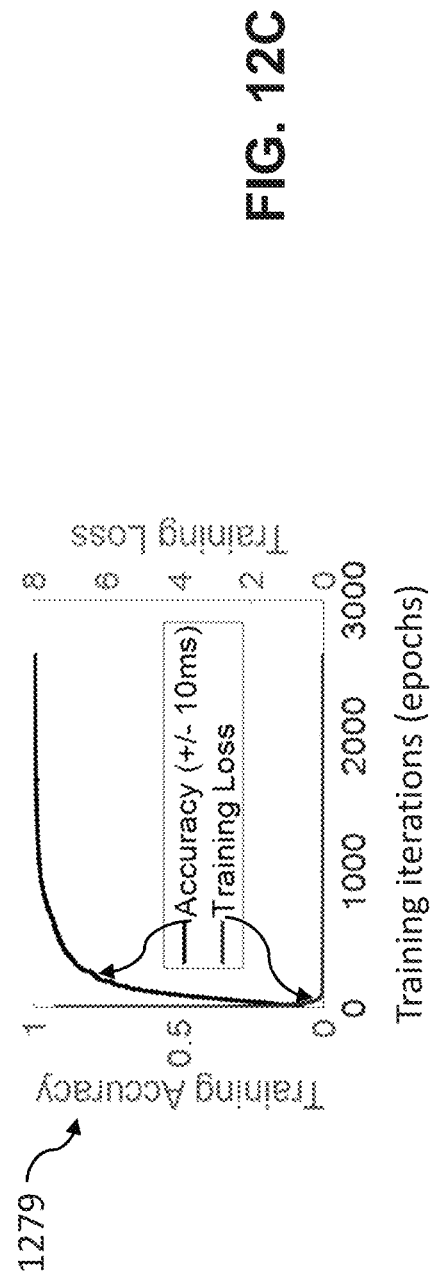
Figure 12D:
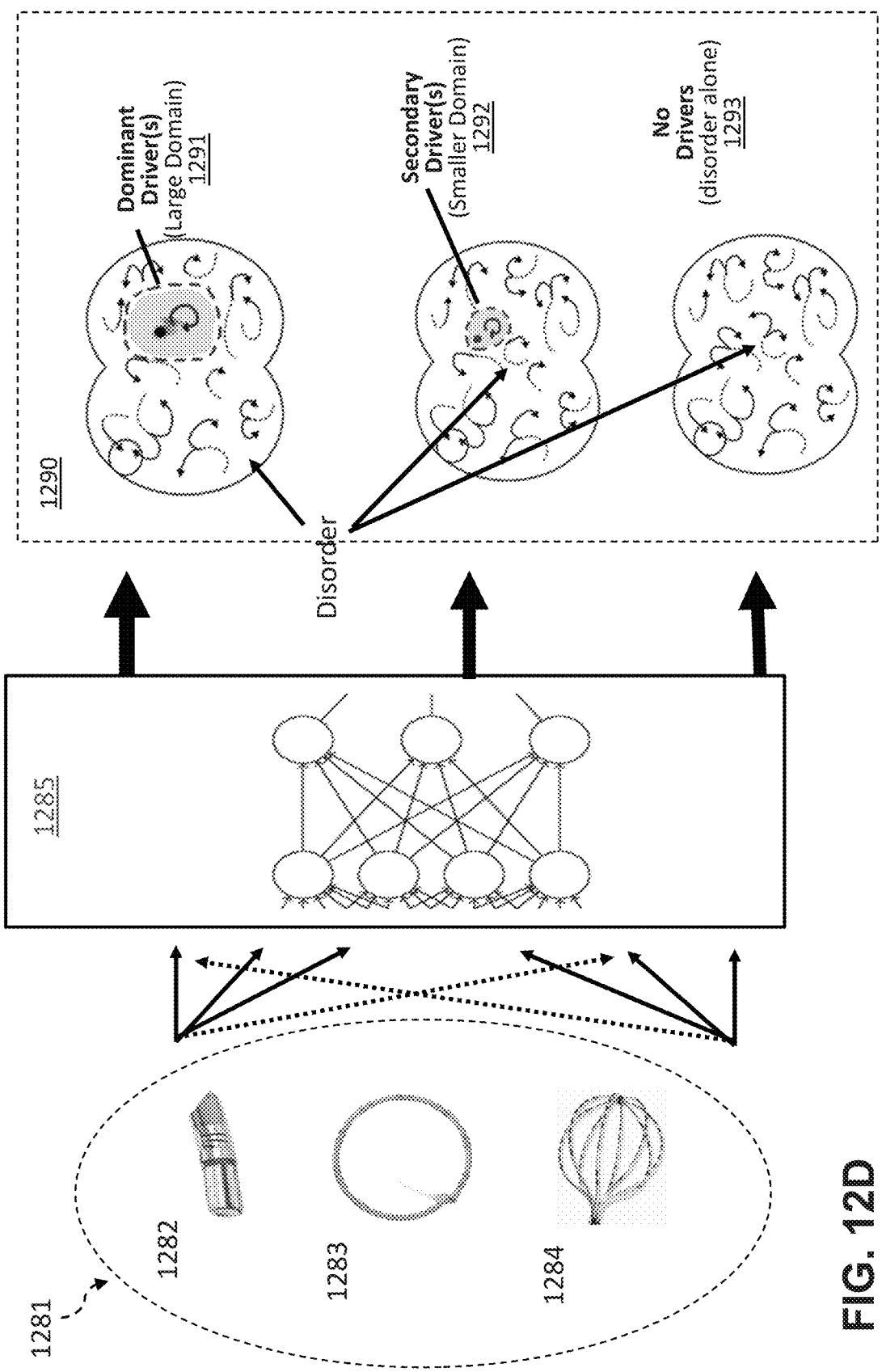

FIGS. 12B-D illustrate utility of the inventive scheme to identify (map) causes of a heart rhythm disorder personalized to an individual, such as for guiding ablation therapy. FIG. 12B illustrates an unmet need arising from the fact that clinical electrograms in complex rhythm disorders can be ambiguous and rarely provide the detailed information needed to establish causes (mechanisms) in experimental models (e.g., animals). FIG. 12C provides an example of how the inventive approach addresses this need by analyzing clinical electrograms to reconstruct signal types, previously seen only in experimental models, personalized to the individual. FIG. 12D shows how this can generate tailored maps of the arrhythmia, to personalize therapy for each individual.

FIGS. 12B-12D illustrate the inventive approach through the example of atrial fibrillation (AF), however this example is not intended to limit the scope of the invention, which can be applied to other rhythm disturbances of the atria or ventricle, or to electrical disorders in other organ systems, such as the brain.

Referring to FIG. 12B, sample clinical AF signal 1265 includes components, i.e., false deflections, that cannot possibly represent activation of nearby (local) tissue because they occur more quickly than cells are able to recover (repolarization is typically >120-200 ms (from Narayan et al., *J Am Coll Cardiol* 2008).) Note that this is the case even for very small (e.g., 0.3 mm) electrodes in direct contact with the human heart from surgical mapping (Allessie et al., *Circulation* 2010), and is likely to be more ambiguous with the larger electrodes (2-4 mm) used by experts in treating patients. Experts are unclear which deflection from each AF "beat" to select as activation (depolarization) because recovery (repolarization) is not known. Panel 1267 shows that choosing any of three acceptable deflections within the clinical signal (based on expert-based rules: minima of the first derivative (dV/dt), produces very different maps of AF from the same recording (Zaman et al., *Circulation Arrhythmia and Electrophysiology*, 2018). Panel 1269 illustrates that some or none of these clinically marked signals may actually coincide with a reference signal—the action potential in these patients from monophasic action potential (MAP) recordings, which have been shown to accurately represent depolarization (MAP onset, "0") and repolarization (MAP offset, "E"). Several deflections of the clinical AF electrogram do not coincide with either onset or offset of the reference and are labeled "far field" (i.e., not local, "F").

FIG. 12C provides an example of how the inventive method reconstructs the reference in AF (action potentials, MAP output) from ambiguous clinical input signals. Multiple deflections in the clinical signal are automatically tagged by the inventive approach for MAP onset 1275 (i.e., activation, depolarization), where the solid vertical line represents "prediction" and dashed vertical line indicates "true", and MAP offset 1277 (i.e., recovery, repolarization). Each panel shows real data in AF, i.e., reduction to practice, in blinded test sets after training this component of the inventive scheme on independent labeled training data, with inputs from clinical AF electrograms at the lower part and the MAPs at the upper part of each plot. Labeling of MAP onset 1275 and offset 1277 was deterministic from standard formulae. As can be seen along the lower border of onset panel 1275, errors in the reconstruction in marking depolarization and repolarization are very small (7.2-16.5 ms), falling well within the marking error of human experts. Plot 1279 shows training accuracy of the machine learning algorithm with 16,560 EGM/MAP samples, with the algorithm converging to nearly 100% accuracy. Machine learning allows tailoring not only to the clinical signal, but also allows personalization to the patient type (male/female, differing ages, body mass indices, comorbid conditions and so on), location of signal recording (right atrium, left atrium, near pulmonary veins, left atrial appendage, left atrial posterior wall and other regions), and other tissue characteristics (e.g., presence of fibrosis, which may alter signal characteristics relative to action potentials of tissue).

FIG. 12D diagrammatically illustrates implementation of the inventive personalized mapping scheme using input clinical signals in AF for a patient. The clinical signals 1281 may be generated using a single electrode such as an ablation or mapping catheter 1282, or multiple electrodes in mapping catheters of circular 1283, basket 1284 or other shapes. The mapping scheme applies machine learning algorithms 1285 (or other classifiers as are known in the art) to reconstruct signals of higher detail and interpretability (such as monophasic action potentials in FIG. 12C). This processing results in arrhythmia maps 1290 that may differ from what would be obtained through the use of the clinical signal alone, or analyzed by traditional expert-based rules. These maps are referred to as 'machine learned MAP maps' or 'virtual MAP maps' from clinical recording catheters. In particular, the resulting arrhythmia maps may reveal that some patients have one or more organized driver regions. These may be dominant, evidenced by their control of large regions of the heart (1291), or they may be secondary, evidenced by their control of smaller regions of the heart (1292). Some patients may not have driver regions evident at that time, and have very disorganized AF (1293). These arrhythmia maps can be used to guide therapy such as ablation personalized to that individual. This analysis can also be performed repeatedly to determine whether the complex arrhythmia map changes over time, or to identify secondary driver regions that may appear, disappear and reappear.

The ability of the inventive approach to reconstruct action potential mapping in human hearts is unique. This approach approximates in live patients the process of optical imaging of explanted human hearts, a gold standard that maps action potentials to avoid the ambiguity of clinical signals (Hansen, Fedorov et al., *JACC Clin. Electrophysiol.* 2018), yet which cannot be applied to live patients. The inventive approach allows identification of organized regions in disorganized rhythms. Organized regions that are of larger size may be more dominant than organized regions of smaller size, and may be better targets for therapy. The ability to identify such regions is not available in prior methods that do not reconstruct action potentials.

Figure 12E:
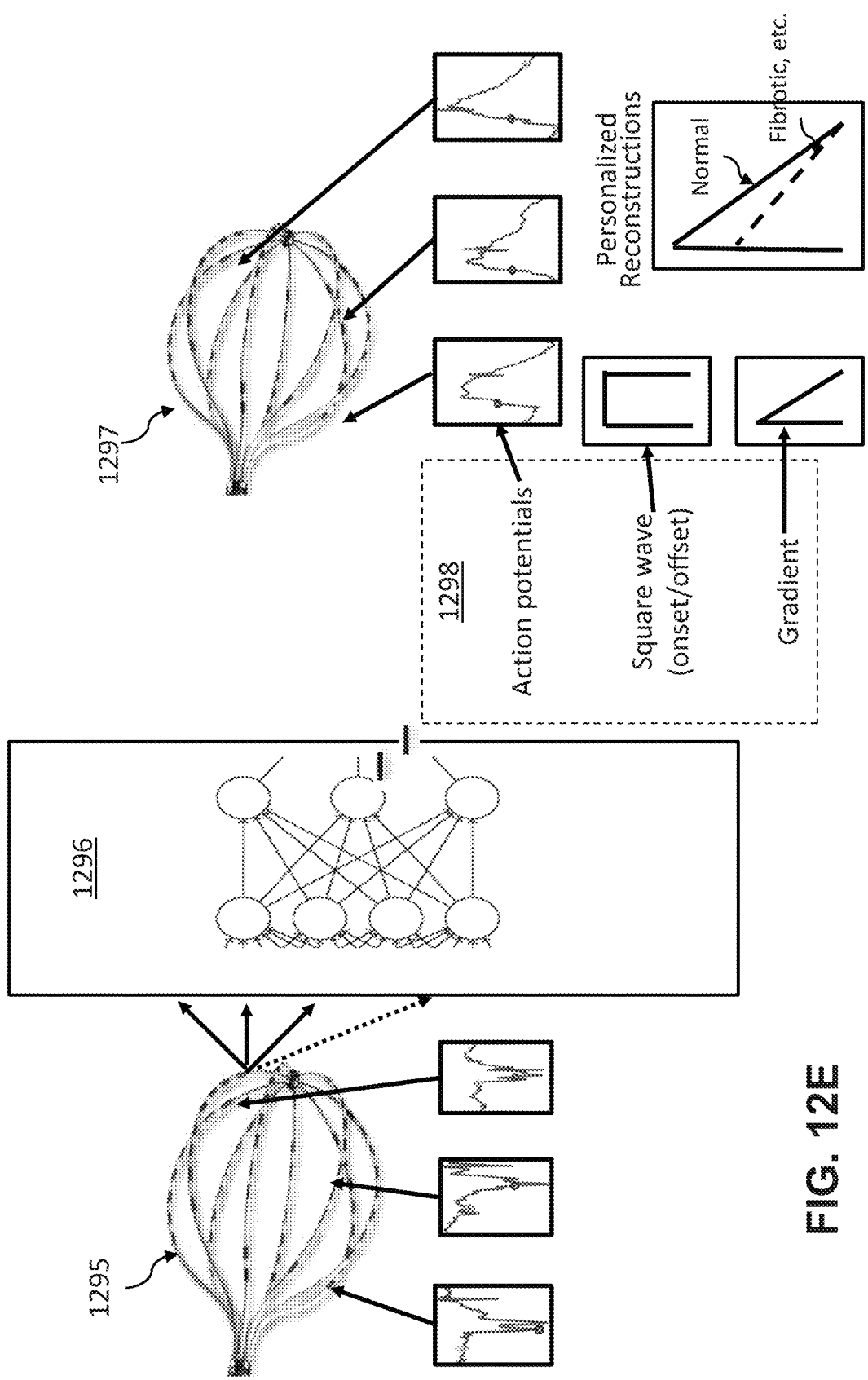

FIG. 12E diagrammatically illustrates how the inventive approach can generate a "virtual signal basket catheter" 1297 from ambiguous clinical input signals 1295. In this example, the input signals 1295 are unipolar electrograms from an input basket probe which are input into the machine learning algorithm 1296. In 1298, reconstructed waveforms are action potentials, as a familiar physiological signal for which the invention has already been trained on labeled reference training data for multiple rhythms (AF, VT, VF; e.g., FIG. 12C). However, other bioengineered signal types can be generated that are optimized for specific tasks. Square waves in 1298 show local depolarization blanked up until repolarization, which may be suited to activation mapping (minimizing spurious deflections). Gradient (triangular, saw-tooth) signals in 1298 show a gradual gradient in amplitude from onset to repolarization, and may be useful for phase mapping. Other shapes can be engineered, optimized to the mapping approach using known activation, recovery and rate information. Each signal type can be tailored by the invention to individual characteristics, such as lower amplitude for regions near scar or fibrosis (shown), or higher amplitude near thick tissue regions such as the mitral isthmus in the left atrium, and so on. Several other signal types can be reconstructed for various applications and should be apparent to someone skilled in the art.

The inventive scheme differs from all prior mapping approaches for complex arrhythmias, which do not portray repolarization as well as depolarization, and which therefore cannot identify which signals may be far-field (false-positives) because they fall within the recovery (repolarization) time (as explained by Narayan et al., *Heart Rhythm* 2016). While the embodiments described and illustrated herein employs machine learning and neural networks, it will be readily apparent to those in the art that other classifiers, including multiple parallel algorithms, can be applied as described.

Figure 13A:
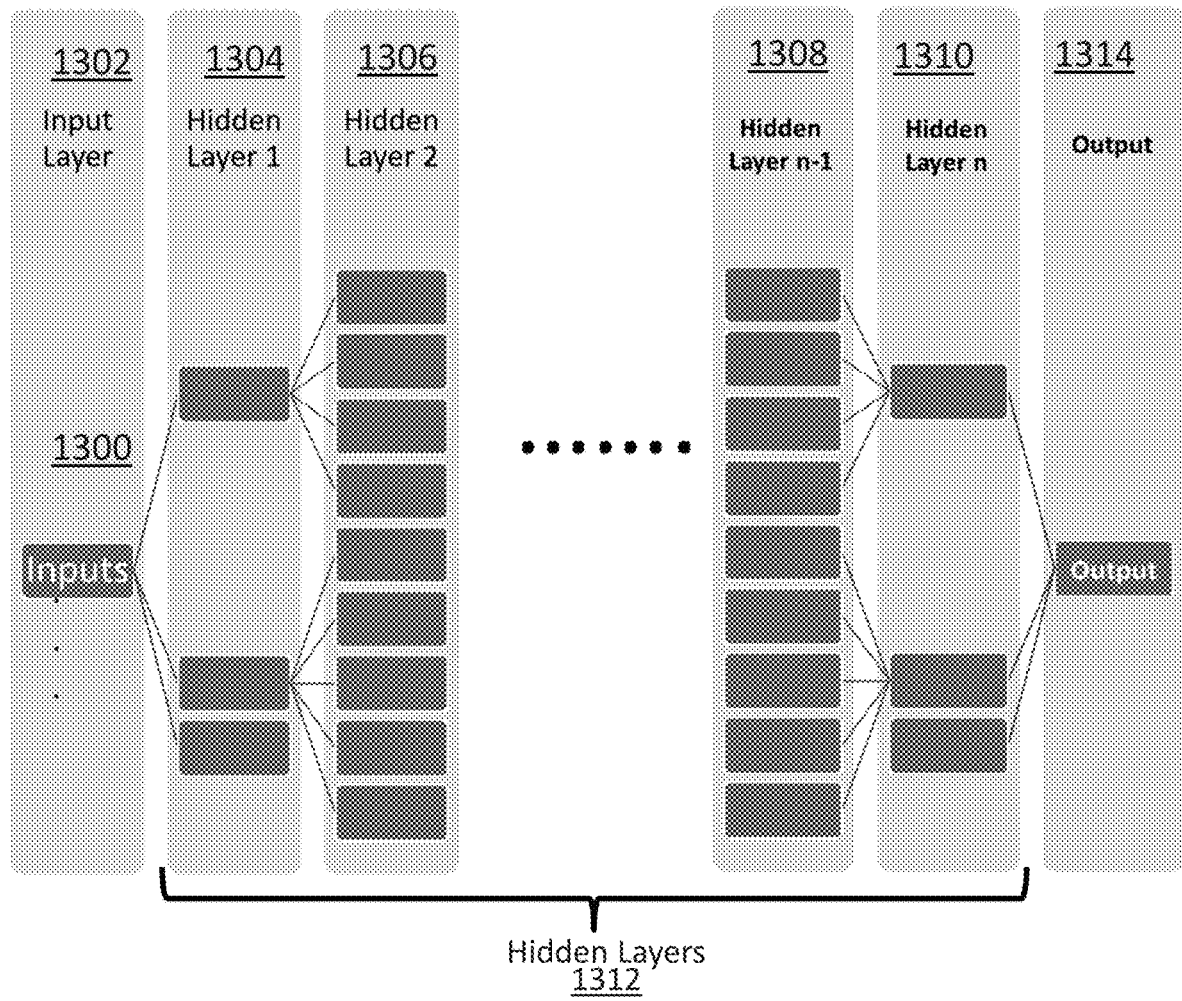
FIG. 13A shows an exemplary design of a machine learning approach using a CNN.

FIG. 13A shows a sample diagram for the machine learning algorithms. In this case, multiple inputs 1300 are provided in via the input layer 1302. Each input will differ with the data type. For example, electrogram streams may take the form of matrices of 1-dimensional arrays representing voltage-time for multiple channels. Imaging data may be represented as a matrix representing the intensity of a voxel (floating point integer) at each coordinate in 3-dimensional space or a pixel in 2-dimensional space. Ordinal values can be used to represent male/female gender, simple variables for age.

Connections link each input with one or more nodes (also termed 'neurons' or 'elements') in hidden layers 1 (1304), hidden layer 2 (1306), to hidden layer n−1 (1308) and hidden layer n (1310). In aggregate, hidden layers 1312, can comprise variable numbers which may vary with the complexity of the input data to this system. Hidden layers 1312 can be any serial combination of layers including, but not limited to, convolutional, pooling, locally-connected, recurrent, embedding, merge, activation, normalization, noise, dropout, dense, flatten, reshape, permute, repeat-vector, regularization, masking layers. The implementation of each layer or groups of layers within the network can differ from another layer or groups of layers. The output 1314 can comprise one or more nodes that code the classification task. For certain applications, this may be a binary (integer) value, such as "diagnosis of Atrial fibrillation," "Yes" or "No." In other cases, the output can be represented by a spectrum or range given by continuous variables, such as "Presence of a source/driver in atrial fibrillation" in which 0.0 would be absent, 1.0 would be present in that region continuously and 0.7 may be intermittent but present some proportion of the time.

Figure 13B:
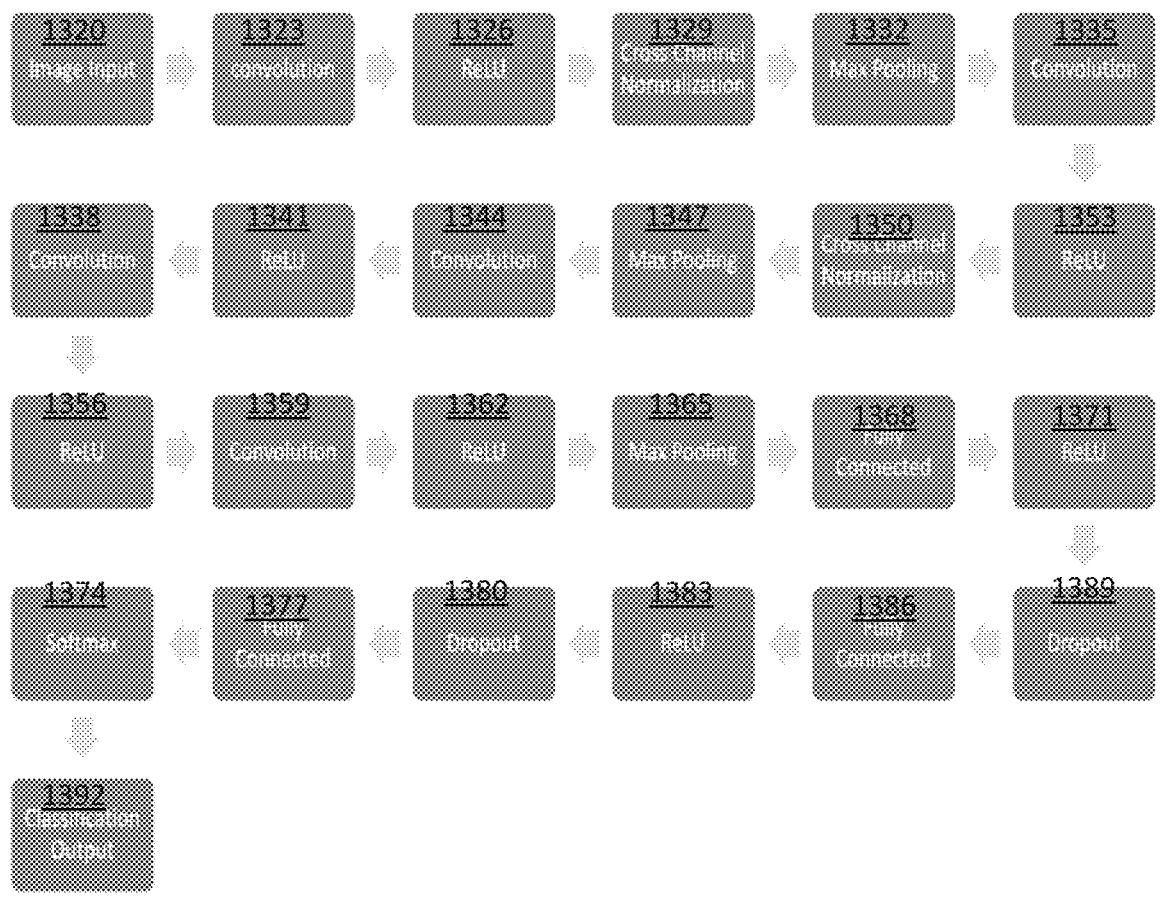
FIG. 13B shows an exemplary process flow for a supervised machine learning approach for personal digital phenotypes.

In FIG. 13B, steps 1320-1347 illustrate another sample embodiment modified from AlexNet (a convolutional neural network), which may input the steps of an image input (for the AF map analysis in FIG. 12, a preferred embodiment). Steps cycle from image input, convolution, rectified linear unit (ReLU), cross-channel normalization, maximum pooling, Max- and average-pooling layers (shown), fully connected layers and dropout layers which set the layers' input elements to zero with a given probability. For classification problems, a Softmax layer or a binary crossentropy layer must follow the final fully connected layer. Step 1320 represents the input (e.g., the image) to the network. Step 1323-1326 represents two consecutive blocks convolution (Conv), activation (ReLU), batch normalization (BN), and Max pooling (MP) CNN layers. Steps 1329-1335 represents three consecutive Conv and ReLU blocks. Steps 1338-1341 represent two consecutive blocks of Fully Connected (FC), ReLU and Dropout (DP) blocks. 1344 represent one FC block, 1347 represents binary cross-entropy output classification layer, The above Convolutional Neural Network (CNN) is an illustration of AlexNet implementation in Python. Other networks can be used, including, but not limited to, Inception-v3, ResNet-50, ResNet-101, GoogLeNet, VGG-16, VGG-19, and DenseNet, in different computing platforms. A specific network design can be implemented to incorporate all of the desired data. Other network architectures can be employed, selection of which will be readily apparent to one skilled in the art.

Figure 14A:
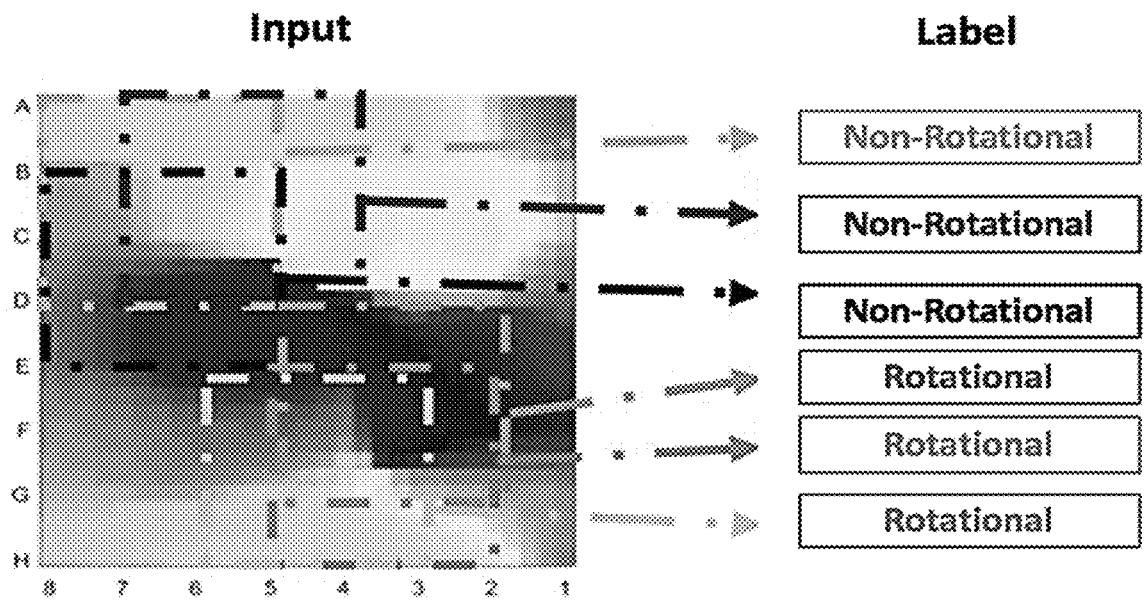
FIGS. 14A-14D provide exemplary output information generated in an embodiment of the inventive system for heart rhythm disorders showing.
Figure 14B:
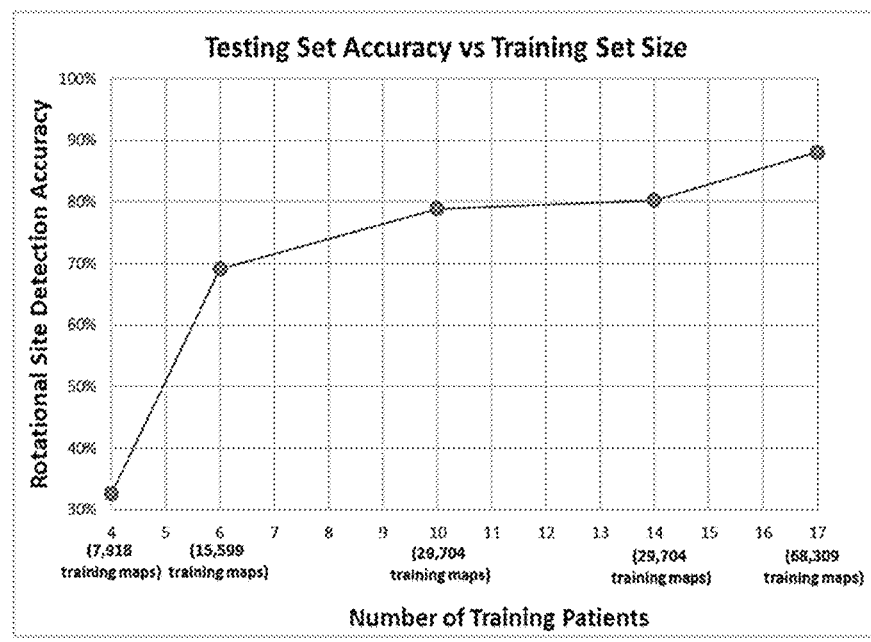

FIGS. 14A-14E provide sample results of processing with the inventive method as reduced to practice using the embodiments of FIGS. 13A and 13B. FIG. 14A shows an AF map created by phase analysis, segmented into sub-regions exhibiting rotation and sub-regions with no rotation. FIG. 14B is a plot of training behavior of the CNN with very high accuracy for detecting critical regions of AF, where localized ablation terminated persistent AF prior to pulmonary vein isolation. These data show results of >90% accuracy on test data, i.e., data that was not used for training of the convolutional neural network.

Figure 14C:
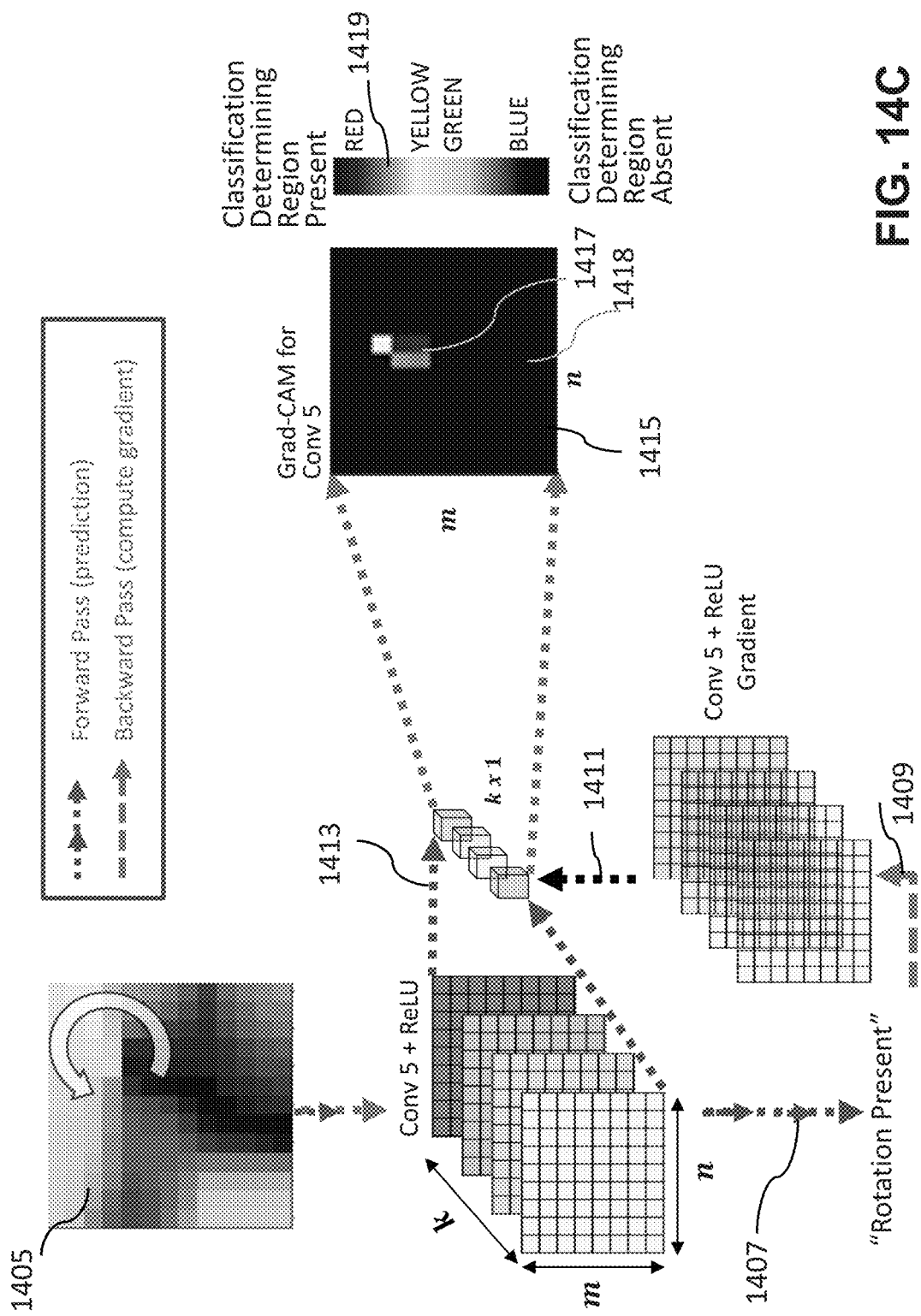

FIG. 14C illustrates a unique aspect of the inventive approach to interpret machine learning in arrhythmia diseases. Since lack of interpretability is considered a limitation of most prior machine learning applications, the inventive scheme has been designed to provide interpretability for its learned patterns. FIG. 14C diagrammatically explains how the trained networks achieved their classifications. Several approaches can be used and will be familiar to those skilled in the art. The process illustrated is Gradient-weighted Class Activation Mapping (Grad-CAM), designed by RR. Selvaraju, et al., which fuses the class-conditional property of CAM with existing pixel-space gradient visualization techniques to highlight fine details on the image. Grad-CAM can be applicable to a wide variety of CNN model-families, including CNNs with fully-connected layers (e.g., VGG19), CNNs used for structured outputs (e.g., captioning), CNNs used in tasks with multi-modal inputs (e.g., VQA), or reinforcement learning, without architectural changes or re-training.

In FIG. 14C, input map 1405 is an image showing rotational activation in AF, acquired using a standard mapping approach. Data from the input map 1405 is transformed for machine learning and, in step 1407, forward propagation of the input vector is performed through the trained CNN (Conv 5+ReLU) to generate a predicted label (I/O), e.g., "Rotation Present". In Step 1409, a backward propagation algorithm is executed to compute the gradients of output label (I/O) with respect to each convolutional layer, each of which represents neuron importance weights of dimensions equal to the convolutional layer (m, n, k). In step 1411, values are averaged along m and n, resulting in a vector of size (k). In step 1413, dot products between the average gradient vector and outputs of the convolutional layers along the third dimension (k dimension), result in an m×n matrix 1415, with higher values 1417 representing more important regions than lower values 1418. (For ease of illustration, only the convolutional layers are shown.) In the heat map 1415, warmer colors (at the upper end of the color spectrum, labeled "RED", "YELLOW", "GREEN", "BLUE" in color scale 1419) indicate regions of the trained network most responsible for classification. In other words, they indicate how the network makes its decisions.

Figure 14D:
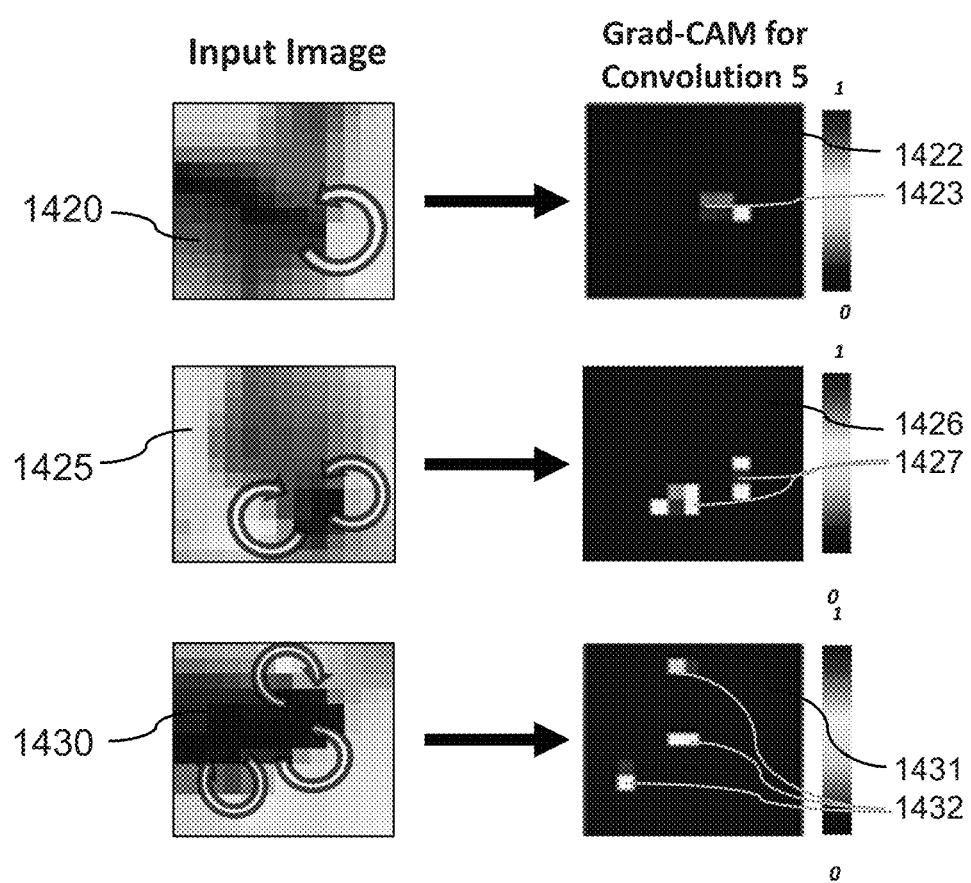

FIG. 14D provides examples of results of the process of FIG. 14C. Input map 1420 shows a single site of interest (rotational activity) in AF in a 64-year-old man. The trained network was able to detect this site, and the resulting heatmap 1422 shows precisely the location 1423 in the heart that would have been coded by experts as the site of rotational activity. From input map 1425, showing AF in a 74-year-old man, heatmap 1426 indicates two concurrent regions of interest 1427, which were identified automatically by Grad-CAM processing, demonstrating excellent agreement with sites that would have been selected by experts. Input map 1430, shows AF in a 65-year-old man: three regions of interest are shown and detected by Grad-CAM in which heatmap 1431 precisely indicates each region 1432 that would have been similarly flagged by experts.

The preceding "explainability" analysis of the network demonstrates that the trained network, without explicit training in the pathophysiology (causes) of AF, made its successful classification decisions by empirically identifying features that would have been selected visually by experts. Overall, in a series of 35 patients and 175,000 images, this approach identified the features that would have been selected by experts with a sensitivity of >90% and specificity >90%.

Different interpretability analyses can be used and would be apparent to one skilled in the art. Grad-CAM does not require modification of the trained CNN and it can be automated, however, other approaches can be used. One approach is to extract features from different layers, visualize them as images and analyze them visually for specific features. Sensitivity analysis has been proposed, in which portions of the input are omitted or grayed out systematically and their importance inferred by resulting changes in classification. Such methods may be limited as multiple concurrent regions are difficult to probe simultaneously, because omitting portions of the input may create artefactual features for classification, and altering the representation may fundamentally change confidence in network predictions. In different interpretability analyses, the network may identify features that differ from those identified by experts. This may be an advantage or a disadvantage for each embodiment of the invention.

Figure 14E:
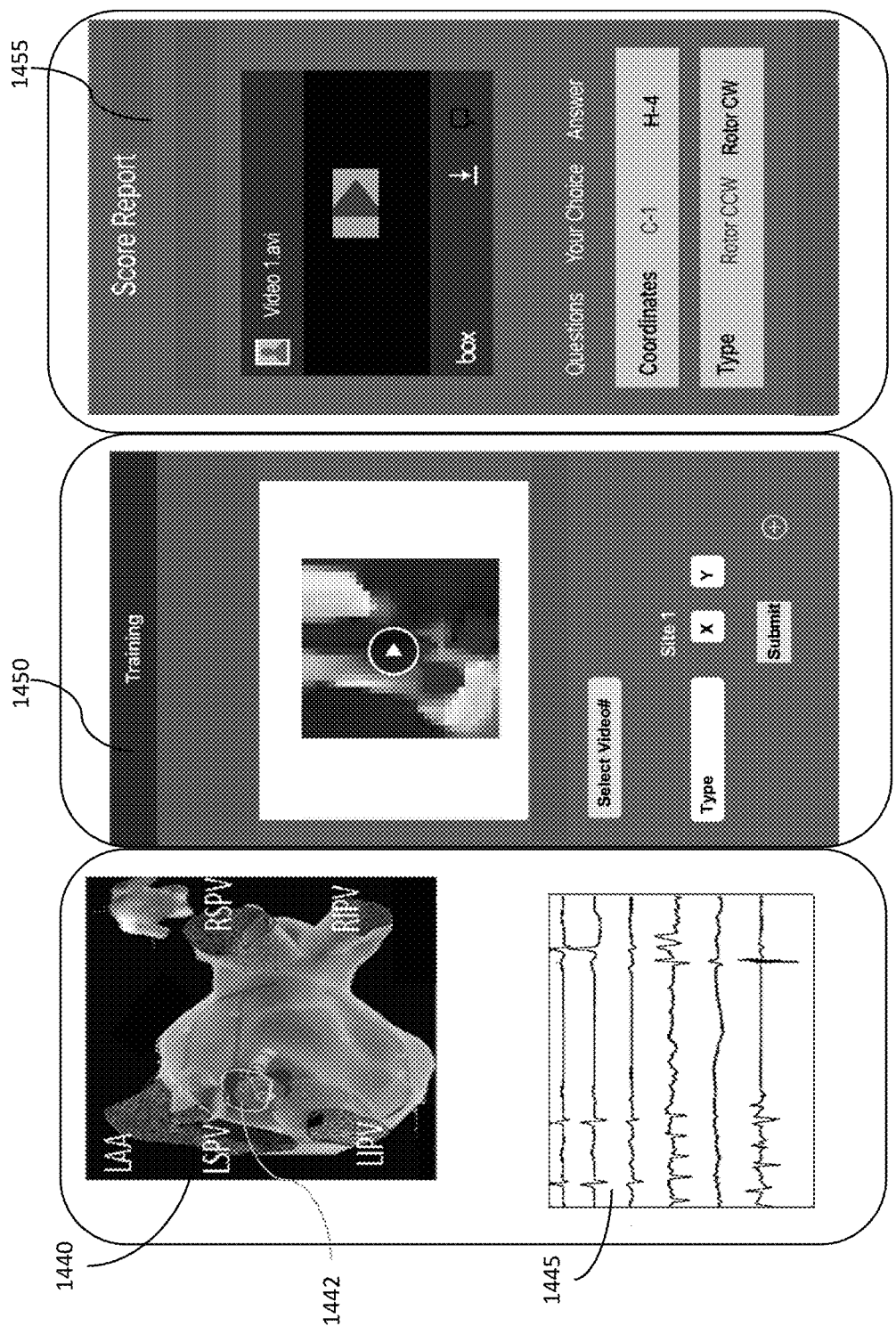

FIG. 14E illustrates sample user interface displays of the data on a custom-designed smartphone app. Display panel 1440 shows the site of termination from digitally acquired personal data from an imaging/mapping system. This example display shows the left atrium with the left superior pulmonary vein (LSPV), left inferior pulmonary vein (LIPV), right superior pulmonary vein (RSPV) and right inferior pulmonary vein (RIPV) labeled. The site of termination corresponds to the lesions within the circled area 1442 for this specific patient. Personal digital data 1445 shows electrograms at termination of AF to sinus rhythm. Display panel 1450 shows the personal streaming data of an AF map created by freely-available online methods playing in a smartphone app. Display panel 1455 show interactive input with the physician to identify the critical site for personalized therapy.

Figure 15:
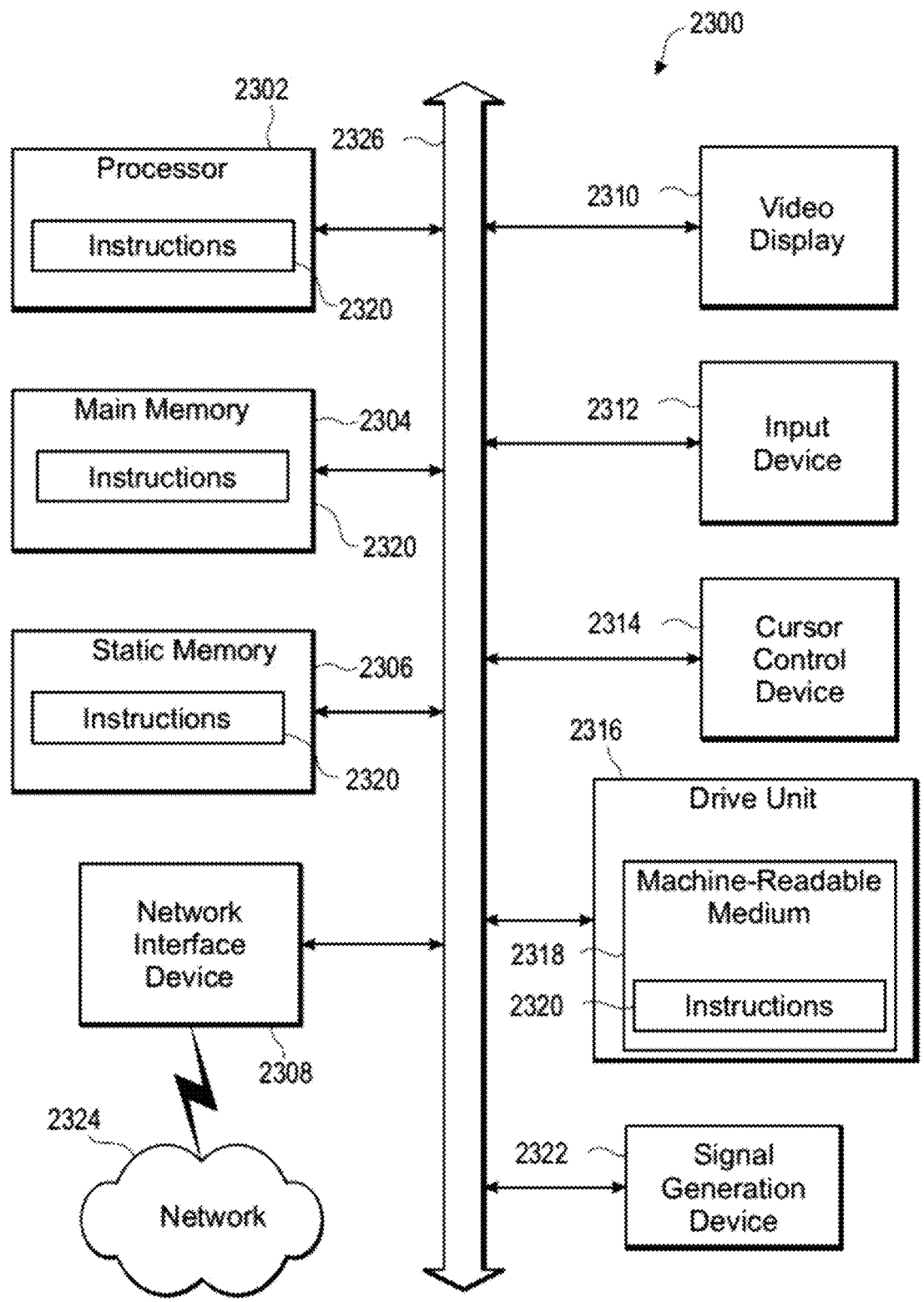
FIG. 15 is a block diagram of an exemplary embodiment of a general computer system for implementing the invention.

FIG. 15 diagrammatically illustrates a computer system that can be used to implement the inventive method, as may be incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 2300 is illustrated, the term "system" should also be taken to include any collection of systems or sub-systems that can individually or jointly execute a set, or multiple sets, of instructions to perform one or more computing functions.

As illustrated in FIG. 15, the computer system 2300 may include a processor 2302, e.g., a central processing unit (CPU), a graphics-processing unit (GPU), or both. The computer system may include a main memory 2304 and a static memory 2306 that can communicate with each other via a bus 2326. As shown, the computer system 2300 may further include a video display unit 2310, such as a liquid crystal display (LCD), an organic light emitting diode (OLED), a flat panel display, a solid state display, or a cathode ray tube (CRT). Additionally, the computer system 2300 may include an input device 2312, such as a keyboard, and a cursor control device 2314, such as a mouse. The computer system 2300 can also include a drive unit 2316, a signal generation device 2322, such as a speaker or remote control, and a network interface device 2308.

In a particular embodiment, as depicted in FIG. 15, the drive unit 2316 may include a computer-readable medium 2318 in which one or more sets of instructions 2320, e.g., software, are stored. The drive unit 2316 may be a disk drive, a thumb drive (USB flash drive), or other storage device. Further, the instructions 2320 may embody one or more of the methods or logic as described herein. In a particular embodiment, the instructions 2320 may reside completely, or at least partially, within the main memory 2304, the static memory 2306, and/or within the processor 2302 during execution by the computer system 2300. The main memory 2304 and the processor 2302 also may include computer-readable media.

In an alternative embodiment, dedicated hardware implementations, such as application specific integrated circuits (ASICs), programmable logic arrays (PLAs) and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments, the methods described herein may be implemented by software programs tangibly embodied in a processor-readable medium and may be executed by a processor. Further, in an exemplary, non-limited embodiment, implementations can include distributed processing, component/object distributed processing, and parallel processing. Alternatively, virtual computer system processing can be constructed to implement one or more of the methods or functionality as described herein.

It is also contemplated that a computer-readable medium includes instructions 2320 or receives and executes instructions 2320 responsive to a propagated signal, so that a device connected to a network 2324 can communicate voice, video or data over the network 2324. Further, the instructions 2320 may be transmitted or received over the network 2324 via the network interface device 2308.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

The foregoing describes embodiments of a system and method to create personalized digital phenotypes of disease, which are compared to digital taxonomies to personalize therapy. Although specific example embodiments have been described, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This detailed description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown.

REFERENCES (INCORPORATED HEREIN BY REFERENCE)

1. Barbato E, et al., Review and Updates in Regenerative and Personalized Medicine, Preclinical Animal Models, and Clinical Care in Cardiovascular Medicine. *Journal of Cardiovascular Translational Research,* 2015; 8:466-74.
2. Darbar D, Genetics of atrial fibrillation: rare mutations, common polymorphisms, and clinical relevance. *Heart Rhythm.* 2008; 5:483-6.
3. Van Driest S L, et al., Association of Arrhythmia-Related Genetic Variants With Phenotypes Documented in Electronic Medical Records. *JAMA,* 2016; 315:47-57.
4. Lahrouchi N, et al., Utility of Post-Mortem Genetic Testing in Cases of Sudden Arrhythmic Death Syndrome. *J Am Coll Cardiol.* 2017; 69:2134-2145.
5. Parvez B, et al., A common beta1-adrenergic receptor polymorphism predicts favorable response to rate-control therapy in atrial fibrillation. *J Am Coll Cardiol.* 2012; 59:49-56.
6. Ritchie M D, et al., Chromosome 4q25 variants are genetic modifiers of rare ion channel mutations associated with familial atrial fibrillation. *J Am Coll Cardiol.* 2012; 60:1173-81.
7. Kuck K H, et al., Cryoballoon or Radiofrequency Ablation for Paroxysmal Atrial Fibrillation. *N Engl J Med.* 2016; 74:2235-45.
8. Verma A, et al., Approaches to catheter ablation for persistent atrial fibrillation. *N Engl J Med.* 2015; 372:1812-22.
9. Narayan S M, et al., Panoramic Electrophysiological Mapping But Not Individual Electrogram Morphology Identifies Sustaining Sites for Human Atrial Fibrillation (AF Rotors and Focal Sources Relate Poorly to Fractionated Electrograms). *Circ Arrhythm Electrophysiol.* 2013; 6:58-67.
10. Sahli Costabal F, et al., Interpreting Activation Mapping of Atrial Fibrillation: A Hybrid Computational/Physiological Study. *Ann Biomed Eng.* 2018; 46(2):257-269.
11. Zaman J A B, et al., Identification and Characterization of Sites Where Persistent Atrial Fibrillation is Terminated by Localized Ablation. *Circulation Arrhyth/Electrophys.* 2018; 11:e005258; in press.
12. Sahadevan J, et al., Epicardial Mapping of Chronic Atrial Fibrillation in Patients: Preliminary Observations. *Circulation,* 2004; 110:3293-3299.
13. Sanders P, et al., Localization of maximal dominant frequency sources correlates with the termination of atrial fibrillation during catheter ablation (abstract). *Heart Rhythm.* 2004; 1:S12.
14. Nademanee K, et al., A new approach for catheter ablation of atrial fibrillation: mapping of the electrophysiologic substrate. *J Am Coll Cardiol.* 2004a; 43:2044-2053.
15. Cuculich P S, et al., Noninvasive Characterization of Epicardial Activation in Humans With Diverse Atrial Fibrillation Patterns. *Circulation,* 2010; 122:1364-72.
16. Wong K C, et al., No Benefit OF Complex Fractionated Atrial Electrogram (CFAE) Ablation in Addition to Circumferential Pulmonary Vein Ablation and Linear Ablation: BOCA Study. *Circ Arrhythm Electrophysiol,* 2015; 8:1316-24.
17. Narayan S M, et al., Treatment of Atrial Fibrillation by the Ablation of Localized Sources: The Conventional Ablation for Atrial Fibrillation With or Without Focal Impulse and Rotor Modulation: CONFIRM Trial. *J Am Coll Cardiol.* 2012; 60:628-636.
18. Haissaguerre M, et al., Driver Domains in Persistent Atrial Fibrillation. *Circulation,* 2014; 130:530-8.
19. Krummen D E, et al., Rotor Stability Separates Sustained Ventricular Fibrillation From Self-Terminating Episodes in Humans. *J Am Coll Cardiol.* 2014; 63:2712-21.
20. Alhusseini M, et al., Two Independent Mapping Techniques Identify Rotational Activity Patterns at Sites of Local Termination during Persistent Atrial Fibrillation. *J Cardiovasc Electrophys.* 2017; 28:615-622.
21. Zaman J A B, et al., Rotational Drivers in Atrial Fibrillation: Are Multiple Techniques Circling Similar Mechanisms? *Circ Arrhythm Electrophysiol,* 2017; 10.
22. Esteva A, et al., Dermatologist-level classification of skin cancer with deep neural networks. *Nature,* 2017; 542:115-118.
23. Rajpurkar P, et al., Cardiologist level arrhythmia detection with convolutional neural networks. 2017; arXiv:1707.01836 [cs.CV].
24. Abed H S, et al., Effect of weight reduction and cardiometabolic risk factor management on symptom burden and severity in patients with atrial fibrillation: a randomized clinical trial. *JAMA.* 2013; 310:2050-60.
25. Selvaraju, R. R., et al., Grad=CAM: Visal Explanation from Deep Networks via Gradient-based Localization, arXiv:1610.02391v3, 21 Mar. 2017.

The invention claimed is:

1. A method for identifying and treating a heart rhythm disorder in a patient, the method comprising:
   collecting electrical signals of a patient's heart generated by an electrical sensor in contact with a region of the patient's heart;
   acquiring patient data elements comprising one or more of demographic, clinical, laboratory, pathology, chemical, image, historical, genetic, and activity data for the patient;
   reconstructing action potentials of the patient's heart by filtering out noise from the electrical signals;
   generating a map of the electrical activity of the patient's heart with the reconstructed action potentials;

identifying one or more sources of a complex rhythm disorder based on the map of the electrical activity and the patient data elements;

comparing the PDP the identified one or more sources and patient data elements to a population digital taxonomy to classify the patient into one or more quantitative disease classifications, the population digital taxonomy comprising stored prior data on other patients having one or more quantitative disease qualifications; and personalizing treatment for the patient based on the one or more quantitative disease classifications for the patient.

2. The method of claim 1, wherein the electrical signals are transmitted from the electrical sensor by one of wired or wireless communication.

3. The method of claim 1, further comprising collecting an additional data stream of biological signals from a sensor, wherein the sensor is one or more of an electrode, an optical sensor, a piezoelectric sensor, an acoustic sensor, an electrical resistance sensor, a thermal sensor, an accelerometer, a pressure sensor, a flow sensor, and an electrochemical sensor.

4. The method of claim 3, wherein the biological signals comprise one or more of electrical heart signals, mechanical heart signals, heart rate, heart sounds, breathing sounds, breathing rate, breathing volume, nerve activity, and immunological signals.

5. The method of claim 1, wherein the patient data elements comprise one or more of electrical signals, hemodynamic data, cardiac structure from imaging, clinical factors associated with heart or lung conductions, nerve signals, genetic profile, biomarkers of metabolic status, and patient movement.

6. The method of claim 1, further comprising, prior to processing, applying a time stamp to each of the electrical signals and the patient data elements.

7. The method of claim 1, further comprising partitioning the electrical signals to generate a personalized digital phenotype (PDP), wherein the partitioning algorithm comprises one or more of supervised machine learning, neural networks, correlation analyses, logistic regression analyses, decision trees, time domain analyses, frequency domain analyses, trigonometric transformations, logarithmic transformations, cluster analysis, and unsupervised machine learning.

8. The method of claim 1, wherein the population digital taxonomy further includes prior data of the patient.

9. The method of claim 1, wherein the one or more quantitative disease classifications comprise one or more of rotational or focal activation patterns, intermittent rotational or focal activation patterns, incomplete activation patterns, and sites of specific heart structure or specific anatomical sites in said individual.

10. The method of claim 1, wherein the heart rhythm disorder comprises one or more of atrial fibrillation, ventricular fibrillation, atrial tachycardia, atrial flutter, polymorphic or monomorphic ventricular tachycardia, ventricular flutter, or other electrical disturbance within the heart.

11. The method of claim 10, wherein the map comprises an image representative of activations at locations within the heart, the method further comprising identifying locations of relatively higher activation in the map.

12. The method of claim 10, wherein reconstructing action potentials comprises using a machine learning algorithm trained on one or more reference signals associated with different heart rhythms.

13. The method of claim 1, wherein personalized treatment comprises modifying at least a portion of the patient's tissue by one or more of ablation by energy delivery via contact devices, energy delivery by noncontact devices, electrical therapy, thermal therapy, mechanical therapy, delivery of drug therapy, delivery of immunosuppression, delivery of stem cell therapy, and delivery of gene therapy.

14. The method of claim 1, further comprising generating updated personal historical data for the patient, the classified one or more quantitative disease classifications, the personalized treatment, and a personal treatment outcome.

15. A system for identifying and treating a heart rhythm disorder in a patient, the system comprising:

an electrode catheter comprising at least one electrical sensor configured to detect electrical activity of a patient's heart by recording electrical signals generated within a patient's heart over time, wherein the electrode catheter is configured for sensing from within a chamber of the patient's heart;

a computing device configured to:

collect electrical signals recorded by the electrical sensor over a region of the patient's heart;

collect patient data elements comprising one or more of demographic, clinical, laboratory, pathology, chemical, image, historical, genetic, and activity data for the patient;

reconstruct action potentials of the patient's heart by filtering out noise from the electrical signals;

generate a map of the electrical activity of the patient's heart with the reconstructed action potentials;

identify one or more sources of a complex rhythm disorder based on the map of the electrical activity and the patient data elements;

compare the identified one or more sources and patient data elements to a population digital taxonomy to classify the patient into one or more quantitative disease classifications, the population digital taxonomy comprising stored prior data on other patients having one or more quantitative disease classifications; and determine a personalized treatment for treating the patient based on the classified one or more quantitative disease classifications for the patient.

16. The system of claim 15, wherein the electrical signals are transmitted from the electrical sensor by one of wired or wireless communication.

17. The system of claim 15, wherein the computing device is further configured to collect an additional data stream of biological signals from a sensor, wherein the sensor is one or more of an electrode, an optical sensor, a piezoelectric sensor, an acoustic sensor, an electrical resistance sensor, a thermal sensor, an accelerometer, a pressure sensor, a flow sensor, and an electrochemical sensor.

18. The system of claim 17, wherein the biological signals comprise one or more of electrical heart signals, mechanical heart signals, heart rate, heart sounds, breathing sounds, breathing rate, breathing volume, nerve activity, and immunological signals.

19. The system of claim 15, wherein the patient data elements comprise one or more of electrical signals, hemodynamics, cardiac structure from imaging, clinical factors associated with heart or lung conductions, nerve signals, genetic profile, biomarkers of metabolic status, and patient movement.

20. The system of claim 15, wherein the computing device is further configured to apply a time stamp to each of the electrical signals and the patient data elements.

21. The system of claim 15, wherein the computing device is further configured to partition the electrical signals to generate a personalized digital phenotype (PDP), wherein the partitioning algorithm comprises one or more of supervised machine learning, neural networks, correlation analyses, logistic regression analyses, decision trees, time domain analyses, frequency domain analyses, trigonometric transformations, logarithmic transformations, cluster analysis, and unsupervised machine learning.

22. The system of claim 15, wherein the population digital taxonomy further includes prior data of the patient.

23. The system of claim 15, wherein the one or more quantitative disease classifications comprise one or more of rotational or focal activation patterns, intermittent rotational or focal activation patterns, incomplete activation patterns, and sites of specific heart structure or specific anatomical sites in said individual.

24. The system of claim 15, wherein the heart rhythm disorder comprising one or more of atrial fibrillation, ventricular fibrillation, atrial tachycardia, atrial flutter, polymorphic or monomorphic ventricular tachycardia, ventricular flutter, or other electrical disturbance within the heart.

25. The system of claim 24, wherein the map comprises an image representative of activations at locations within the heart, and wherein the computing device is further configured to identify locations of relatively higher activation in the map.

26. The system of claim 24, wherein the computing device is configured to reconstruct action potentials using a machine learning algorithm trained on one or more reference signals associated with different heart rhythms.

27. The system of claim 15, wherein personalized treatment comprises modifying at least a portion of the patient's tissue by one or more of ablation by energy delivery via contact devices, energy delivery by noncontact devices, electrical therapy, thermal therapy, mechanical therapy, delivery of drug therapy, delivery of immunosuppression, delivery of stem cell therapy, and delivery of gene therapy.

28. The system of claim 15, wherein the computing device is further configured to generate updated personal historical data for the PDP, the classified one or more quantitative disease classifications, the personalized treatment, and a personal treatment outcome.

29. The system of claim 15, further comprising a display device configured to display the classified one or more quantitative disease classifications.

30. The system of claim 15, wherein the computing device is further configured to iteratively collect electrical signals from the electrical sensor.

31. The system of claim 15, wherein the electrode catheter comprises a plurality of electrical sensors configured to detect electrical signals from the patient's heart.

* * * * *

UNITED STATES PATENT AND TRADEMARK OFFICE
CERTIFICATE OF CORRECTION

PATENT NO. : 11,786,174 B2  
APPLICATION NO. : 17/051749  
DATED : October 17, 2023  
INVENTOR(S) : Sanjiv M. Narayan and Mahmood Alhusseini Page 1 of 1

It is certified that error appears in the above-identified patent and that said Letters Patent is hereby corrected as shown below:

In the Specification

Column 1, Line 16, Under GOVERNMENT RIGHTS:
Delete entire paragraph and replace with the following:
-- This invention was made with Government support under contracts HL083359 and HL103800 awarded by the National Institutes of Health. The Government has certain rights in the invention. --

Signed and Sealed this  
Twenty-eighth Day of October, 2025

John A. Squires  
*Director of the United States Patent and Trademark Office*